(12) United States Patent
Gallop

(10) Patent No.: US 7,935,686 B2
(45) Date of Patent: May 3, 2011

(54) ACYLOXYALKYL CARBAMATE PRODRUGS, METHODS OF SYNTHESIS, AND USE

(75) Inventor: Mark A. Gallop, Los Altos, CA (US)

(73) Assignee: XenoPort, Inc., Santa Clara, CA (US)

(*) Notice: Subject to any disclaimer, the term of this patent is extended or adjusted under 35 U.S.C. 154(b) by 207 days.

(21) Appl. No.: 12/353,703

(22) Filed: Jan. 14, 2009

(65) Prior Publication Data

US 2009/0124582 A1 May 14, 2009

Related U.S. Application Data

(62) Division of application No. 11/265,203, filed on Nov. 3, 2005, now Pat. No. 7,494,985.

(60) Provisional application No. 60/624,873, filed on Nov. 3, 2004.

(51) Int. Cl.
*A61K 31/66* (2006.01)
*C07F 9/02* (2006.01)

(52) U.S. Cl. .................. 514/120; 558/177; 558/178

(58) Field of Classification Search .................. 514/120; 558/177, 178
See application file for complete search history.

(56) References Cited

U.S. PATENT DOCUMENTS

| | | | |
|---|---|---|---|
| 2,996,431 A | 12/1953 | Barry | |
| 3,139,383 A | 6/1964 | Neville | |
| 3,402,240 A | 9/1968 | Cain et al | |
| 3,803,112 A | 4/1974 | Engelhardt et al. | |
| 3,811,444 A | 5/1974 | Heller et al. | |
| 3,845,770 A | 11/1974 | Theeuwes et al. | |
| 3,916,899 A | 11/1975 | Theeuwes et al. | |
| 3,962,414 A | 6/1976 | Michales | |
| 3,992,518 A | 11/1976 | Chien et al. | |
| 4,063,064 A | 12/1977 | Saunders et al. | |
| 4,066,747 A | 1/1978 | Capozza | |
| 4,070,347 A | 1/1978 | Schmitt | |
| 4,079,038 A | 3/1978 | Choi et al. | |
| 4,083,949 A | 4/1978 | Benedikt | |
| 4,088,864 A | 5/1978 | Theeuwes et al. | |
| 4,093,709 A | 6/1978 | Choi et al. | |
| 4,126,684 A | 11/1978 | Robson et al. | |
| 4,200,098 A | 4/1980 | Ayer et al. | |
| 4,285,987 A | 8/1981 | Ayer et al. | |
| 4,421,736 A | 12/1983 | Walters | |
| 4,434,153 A | 2/1984 | Urguhart et al. | |
| 4,656,298 A | 4/1987 | Dingwall et al. | |
| 4,721,613 A | 1/1988 | Urguhart et al. | |
| 4,752,470 A | 6/1988 | Mehta | |
| 4,816,263 A | 3/1989 | Ayer et al. | |
| 4,820,523 A | 4/1989 | Shtohryn et al. | |
| 4,853,229 A | 8/1989 | Theeuwes | |
| 4,996,058 A | 2/1991 | Sinnreich | |
| 5,006,560 A | 4/1991 | Kreutner et al. | |
| 5,013,863 A | 5/1991 | Baylis et al. | |
| 5,051,524 A | 9/1991 | Baylis et al. | |
| 5,091,184 A | 2/1992 | Khanna | |
| 5,229,135 A | 7/1993 | Philippon et al. | |
| 5,229,379 A | 7/1993 | Marescaux et al. | |
| 5,281,747 A | 1/1994 | Hall et al. | |
| 5,300,679 A | 4/1994 | Baylis et al. | |
| 5,332,729 A | 7/1994 | Mickel et al. | |
| 5,376,684 A | 12/1994 | Mickel | |
| 5,407,922 A | 4/1995 | Marescaux et al. | |
| 5,424,441 A | 6/1995 | Mickel et al. | |
| 5,461,040 A | 10/1995 | Hall et al. | |
| 5,545,631 A | 8/1996 | Marescaux et al. | |
| 5,567,840 A | 10/1996 | Hall et al. | |
| 5,698,155 A | 12/1997 | Grosswald et al. | |
| 5,719,185 A | 2/1998 | Bountra et al. | |
| 6,117,908 A | 9/2000 | Andrews et al. | |
| 6,171,615 B1 | 1/2001 | Roussin et al. | |
| 6,375,987 B1 | 4/2002 | Farah et al. | |
| 6,379,700 B2 | 4/2002 | Joachim et al. | |
| 6,627,223 B2 | 9/2003 | Percel et al. | |
| 6,664,069 B1 | 12/2003 | Andrews et al. | |
| 7,319,110 B2 | 1/2008 | Lange et al. | |
| 7,585,996 B2 * | 9/2009 | Gallop et al. ................. | 560/115 |
| 7,749,985 B2 * | 7/2010 | Gallop et al. ................. | 514/120 |
| 2002/0187977 A1 | 12/2002 | Pearlman et al. | |
| 2003/0162754 A1 | 8/2003 | Ligon | |
| 2006/0111325 A1 | 5/2006 | Gallop | |
| 2006/0111439 A1 | 5/2006 | Gallop | |
| 2008/0146526 A1 | 6/2008 | Gallop et al. | |

FOREIGN PATENT DOCUMENTS

| | | |
|---|---|---|
| WO | WO 00/57862 A2 | 10/2000 |
| WO | WO 01/08675 | 2/2001 |
| WO | WO 01/26638 | 4/2001 |
| WO | WO 01/42252 | 6/2001 |
| WO | WO 01/54481 A2 | 8/2001 |
| WO | WO 02/096404 | 12/2002 |
| WO | WO 02/100347 A2 | 12/2002 |
| WO | WO 02/100392 | 12/2002 |
| WO | WO 02/100823 | 12/2002 |
| WO | WO 02/100869 | 12/2002 |

(Continued)

OTHER PUBLICATIONS

Alderman, A review of cellulose ethers in hydrophilic matrices for oral controlled-release dosage forms. Int. J. Pharm. Tech. & Prod. Mfr. 1984, 5(3), 1-9.

(Continued)

*Primary Examiner* — Rei-tsang Shiao
(74) *Attorney, Agent, or Firm* — D. Byron Miller; Lucy S. Chang

(57) ABSTRACT

Acyloxyalkyl carbamate prodrugs of 3-aminopropylphosphonous acid, 3-aminopropylphosphinic acid, and analogs thereof, pharmaceutical compositions comprising acyloxyalkyl carbamate prodrugs of 3-aminopropylphosphonous acid, 3-aminopropylphosphinic acid, and analogs thereof, methods of making prodrugs of 3-aminopropylphosphonous acid, 3-aminopropylphosphinic acid, and analogs thereof, methods of using prodrugs of 3-aminopropylphosphonous acid, 3-aminopropylphosphinic acid, and analogs thereof and pharmaceutical compositions thereof for treating or preventing diseases or disorders such as spasticity or gastroesophageal reflux disease are disclosed. Acyloxyalkyl carbamate prodrugs of 3-aminopropylphosphonous acid, 3-aminopropylphosphinic acid, and analogs thereof and sustained release oral dosage forms thereof, which are suitable for oral administration, are also disclosed.

20 Claims, No Drawings

FOREIGN PATENT DOCUMENTS

| | | |
|---|---|---|
| WO | WO 02/100870 | 12/2002 |
| WO | WO 02/100871 | 12/2002 |
| WO | WO 03/011255 | 2/2003 |
| WO | WO 04/000855 A1 | 12/2003 |
| WO | WO 04/000856 A1 | 12/2003 |
| WO | WO 2005/010011 | 2/2005 |
| WO | WO 2005/066122 A2 | 7/2005 |
| WO | WO 2006/050471 A2 | 5/2006 |
| WO | WO 2008/033572 | 3/2008 |

OTHER PUBLICATIONS

Bamba et al., Release mechanisms in gelforming sustained release preparations. Int. J. Pharm. 1979, 2, 307-315.

Bardgett et al., NMDA receptor blockade and hippocampal neuronal loss impair fear conditioning and position habit reversal in C57Bl/6 mice. Brain Res Bull 2003, 60(1-2), 131-142.

Bowery, GABAB receptors and their significance in mammalian pharmacology. Trends Pharmacol. Sci. 1989, 10, 401-407.

Brown et al., Conditioned fear as revealed by magnitude of startle response to an auditory stimulus. J Expt'l Psychol 1951, 41(5), 317-28.

Cange et al., Baclofen-mediated gastro-oesphageal acid reflux control in patients with established reflux disease. Aliment. Pharmacol. Ther. 2002,16, 869-873.

Cercos-Fortea et al., Influence of leucine on intestinal baclofen absorption as a model compound of neutral α-aminoacids. Biopharm. Drug. Disp. 1995, 16, 563-577.

Ciccaglione et al., Effect of acute and chronic administration of the GABAB agonist baclofen on 24 hour pH metry and symptoms in control subjects and in patients with gastro-oesphageal reflux disease. Gut 2003, 52, 464-470.

Coleman et al., A practical guide to polymer miscibility. Polymers 1990, 31, 1187-1231.

Conn (ed.), Handbook of models for human ageing. Amsterdam; Boston, Elsevier Academic Press, 2006.

Cryan and Momereau, In search of a depressed mouse: utility of models for studying depression-related behavior in genetically modified mice. Mol Psychiatry 2004, 9(4), 326-57.

Cryan et al., Assessing antidepressant activity in rodents: recent developments and future needs. Trends Pharmacol Sci 2202, 23(5), 238-45.

Datamonitor, Commercial and Pipeline Perspectives: Upper GI Disorders (No. DMHC2005, Sep. 2004, p. 147): Datamonitor.

Deguchi et al., Study on brain interstitial fluid distribution and blood-brain barrier transport of baclofen in rats by microdialysis. Pharm. Res. 1995, 12(12), 1838-1844.

Deprele and Montchamp, Triethylborane-initiated room temperature radical addition of hypophosphites to olefins: synthesis of monosubstituted phosphinic acids and esters. J Org Chem 2001, 66(20), 6745-55.

Dingwall et al., Diethoxymethylphosphonites and phosphinates. Intermediates for the synthesis of alpha, beta- and gamma-aminoalkylphosphonous acids. Tetrahedron 1989, 45(12), 3787-3808.

During et al., Controlled release of dopamine from a polymeric brain implant: in vivo characterization. Ann. Neurol. 1989, 25(4), 351-6.

Fincher, Particle size of drugs and its relationship to absorption and activity. J. Pharm. Sci. 1968, 57(11), 1825-1835.

Froestl et al., Phosphinic acid analogues of GABA. 1. New potent and selective GABAB agonists. J. Med. Chem. 1995, 38(17), 3297-3312.

Froestl et al., SGS742: the first GABAB receptor antagonist in clinical trials. Biochem Pharmacol 2004, 68(8), 1479-87.

Getova et al., Effects of GABAB receptor antagonists on learning and memory retention in a rat model of absence epilepsy. Eur J Pharmacol 1997, 320(1), 9-13.

Gijsman et al., Antidepressants for bipolar depression: a systematic review of randomized, controlled trials. Am J Psychiatry 2004, 161(9), 1537-47.

Gleiter et al., Pharmacokinetics of CGP 36,742, and orally active GABAB antagonist, in humans. J Clin Pharmacol 1996, 36(5), 428-38.

Goodson, in "Medical Applications of Controlled Release," vol. 2, ed. Langer and Wise, CRC Press, Inc., Boca Raton, FL, 1964, pp. 115-138 (1984).

Greene and Wuts, "Protective Groups in Organic Chemistry," 2nd ed., John Wiley & Sons, Inc., New York, 1991.

Harrison and Harrison, "Compendium of Synthetic Organic Methods," vols. 1-8 Wiley-Interscience, New York, 1971-1996.

Helm et al., GABAB receptor antagonist SG742 improves spatial memory and reduces protein binding to the cAMP response element (CRE) in the hippocampus. Neuropharmacology 2005, 48(7), 956-64.

Higgins and Jacobsen, Transgenic mouse models of Alzheimer's disease: phenotype and application. Behavioral Pharmacology 2003, 14(5-6), 419-38.

Howard et al., Intracerebral drug delivery in rats with lesion-induced memory deficits. J. Neurosurg. 1989, 71,105-112.

Janus and Westaway, Transgenic mouse models of Alzheimer's disease. Physiology & Behav 2001, 73(5), 873-886.

Koek et al., Effect of the GABAB agonist baclofen in patients with symptoms and duodeno-gastro-oespphageal reflux refractory to proton pump inhibitors. Gut 2003, 52, 1397-1402.

Langer and Wise eds.), Medical Applications of Controlled Release, vol. 1 "Classes of Systems," CRC Press., Boca Raton, Fl, 1984.

Langer et al., Chemical and physical structure of polymers as carriers for controlled release of bioactive agents: a review. J Macromol. Sci. Rev. Macromol Chem. 1983, C23(1), 61-126.

Langer, New methods of drug delivery. Science 1990, 249, 1527-1533.

Larock, "Comprehensive Organic Transformations," VCH Publishers, 1989.

Leong et al., Polymeric controlled drug delivery. Adv. Drug Delivery Rev. 1987, 1, 199-233.

Levy et al., Inhibition of calcification of bioprosthetic heart valves by local controlled-release diphosphonate. Science 1985, 228, 190-192.

Li et al., Synthesis of (alkoxycarbonyloxy)methyl, (acyloxy)methyl and (oxodioxolenyl)methyl carbamates as bioreversible prodrug moieties for amines. Bioorganic & Medicinal Chemistry Letters 1997, 7, 2909-2912.

Lidums et al., Control of transient lower esophageal sphincter relaxations and reflux by the GABAB agonist baclofen in normal subjects. Gastroenterology 2000, 118, 7-13.

Lu, Int. Dimensionless presentation for drug release from a coated pure drug bead: 2. Experiment. J. Pharm. 1994, 112, 117-124.

Marescaux et al., GABAB receptor antagonists: potential new anti-absence drugs. J Neural Transm Suppl 1992, 35, 179-188.

Merino et al., Evidence of a specialized transport mechanism for the intestinal absorption of baclofen. Biopharm. Drug. Disp. 1989, 10, 279-297.

Misgeld et al., A physiological role for GABAB receptors and the effects of baclofen in the mammalian central nervous system. Prog. Neurobiol. 1995, 46, 423-462.

Mittal et al., Transient lower esophageal sphincter relaxation. Gastroenterology 1995, 109, 601-610.

Moll-Navarro et al., Interaction of taurine on baclofen intestinal absorption: a nonlinear mathematical treatment using differential equations to describe kinetic inhibition models. J. Pharm. Sci. 1996, 85(11), 1248-1254.

Mondadori et al., CGP 36,742, an orally active GABAB receptor antagonist, facilitates memory in a social recognition test in rats. Behav Brain Res 1996, 77(1-2), 227-29.

Mondadori et al., CGP 36742: the first orally active GABAB blocker improves the cognitive performance of mice, rats, and rhesus monkeys. Behav & Neural Biol 1993, 60(1), 62-68.

Nakagawa and Takashima, The GABAB receptor antagonist CGP 36742 attenuates the baclofen- and scopolamine-induced deficit in Morris water maze task in rats. Brain Res 1997, 766(1-2), 101-106.

Nakagawa et al., The GABAB receptor antagonist CGP36742 improves learned helplessness in rats. Eur J Pharmacol 1999, 381(1), 1-7.

Paquette, "Encyclopedia of Reagents for Organic Synthesis," John Wiley & Sons, New York, 1995.

Porsolt et al., Behavioral despair in mice: a primary screening test for antidepressants. Arch Int Pharmacodyn Ther 1977, 229(2), 327-336.

Porsolt et al., Depression: a new animal model sensitive to antidepressant treatments. Nature 1977, 266, 730-732.

Porsolt, Animal models of depression: utility for transgenic research. Rev Neurosci 2000, 11(1), 53-58.

Post et al., Preliminary observations on the effectiveness of levetiracetam in the open adjunctive treatment of refractory bipolar disorder. J Clin Psychiatry 2005, 66(3), 37-74.

Remington's Pharmaceutical Sciences, Lippincott Williams & Wilkins, 21st Ed, 2005.

Roff et al., "Handbook of Common Polymers," CRC Press, 1971.

Saudek et al., A preliminary trial of the programmable implantable medication system for insulin delivery. N. Engl. J Med. 1989, 321(9), 574-79.

Sefton, Implantable pumps, CRC Crit Ref Biomed Eng. 1987, 14(3), 201-40.

Simpkins et al., Role of nonfeminizing estrogens in brain protection from cerebral ischemia: an animal model of Alzheimer's disease neuropathology. Ann N Y Acad Sci 2005, 1052, 233-242.

Slattery et al., GABAB receptor antagonist-mediated antidepressant-like behavior is serotonin-dependent. J Pharmacol Exp Ther 2005, 312(1), 290-296.

Smolen and Ball (eds.), "Controlled Drug Bioavailability," vol. 1: Drug Product Design and Performance, John Wiley & Sons, New York, 1984.

Tonini et al., Progress with novel pharmacological strategies for gastro-oesophageal reflux disease, Drugs. 2004, 64(4), 347-61.

Van Bree et al., Carrier-mediated transport of baclofen across monolayers of bovine brain endothelial cells in primary culture. Pharm. Res. 1988, 5(6), 369-371.

Van Dam and De Deyn, Drug discovery in dementia: the role of rodent models. Nat Rev Drug Discov 2006, 5(11), 956-970.

Van Herwaarden et al., The effect of baclofen on gastro-oesophageal reflux, lower oesophageal sphincter function and reflux symptoms in patients with reflux disease. Aliment. Pharmacol. Ther. 2002, 16, 1655-1662.

Vela et al., Baclofen decreases acid and non-acid post-prandial gastro-oesophageal reflux measured by combined multichannel intraluminal impedance and pH. Aliment. Pharmacol. Ther. 2003, 17, 243-251.

Vergnes et al., Opposite effects of GABAB receptor antagonists on absences and convulsive seizures. Eur J Pharmacol 1997, 332(3), 245-55.

Verma et al., Osmotically controlled oral drug delivery. Drug Dev. Industrial. Pharm. 2000, 26(7), 695-708.

Zhang et al., Control of transient lower oesophageal sphincter relaxations and reflux by the GABAB agonist baclofen in patients with gastro-oesophageal reflux disease. Gut 2002, 50, 19-24.

International Search Report and Written Opinion of the International Searching Authority, issued May 17, 2006 for International Application No. PCT/US2005/039871.

Office Action mailed Jun. 6, 2007 in U.S. Appl. No. 11/265,204, filed Nov. 3, 2005.

Office Action mailed Aug. 13, 2007 in U.S. Appl. No. 11/265,204, filed Nov. 3, 2005.

Notice of Allowance mailed Feb. 7, 2008 in U.S. Appl. No. 11/265,204, filed Nov. 3, 2005.

Examiner Interview Summary mailed Jul. 9, 2008 in U.S. Appl. No. 11/265,204, filed Nov. 3, 2005.

International Search Report and Written Opinion of the International Searching Authority, or the Declaration, mailed Feb. 19, 2008, for Application No. PCT/US2007/020210, filed Sep. 13, 2007.

International Search Report and Written Opinion of the International Searching Authority, issued Jun. 6, 2006 for International Application No. PCT/US2005/039872.

Office Action mailed Apr. 9, 2008 in U.S. Appl. No. 11/265,203, filed Nov. 3, 2005.

Notice of Allowance mailed Oct. 14, 2008 in U.S. Appl. No. 11/265,203, filed Nov. 3, 2005.

\* cited by examiner

ACYLOXYALKYL CARBAMATE PRODRUGS, METHODS OF SYNTHESIS, AND USE

This application is a divisional application of U.S. application Ser. No. 11/265,203 filed Nov. 3, 2005 now issued as U.S. Pat. No. 7,494,985 on Feb. 24, 2009, which claims the benefit under 35 U.S.C. §119(e) from U.S. Provisional Application Ser. No. 60/624,873 filed Nov. 3, 2004, each of which is incorporated herein by reference in its entirety.

The disclosure relates to acyloxyalkyl carbamate prodrugs of 3-aminopropylphosphonous acid, 3-aminopropylphosphinic acid, and analogs thereof, pharmaceutical compositions comprising acyloxyalkyl carbamate prodrugs of 3-aminopropylphosphonous acid, 3-aminopropylphosphinic acid, and analogs thereof, methods of making prodrugs of 3-aminopropylphosphonous acid, 3-aminopropylphosphinic acid, and analogs thereof, and methods of using prodrugs of 3-aminopropylphosphonous acid, 3-aminopropylphosphinic acid, and analogs thereof and pharmaceutical compositions thereof to treat various diseases or disorders. The disclosure also relates to such prodrugs of 3-aminopropylphosphonous acid, 3-aminopropylphosphinic acid, and analogs thereof suitable for oral administration and for oral administration using sustained release dosage forms.

(±)-4-Amino-3-(4-chlorophenyl)butanoic acid (baclofen), (1)

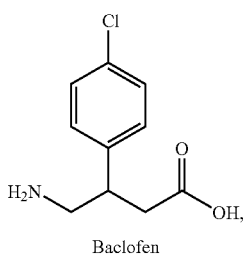

Baclofen is an analog of gamma-aminobutyric acid (i.e., GABA) that selectively activates $GABA_B$ receptors, resulting in neuronal hyperpolarization. $GABA_B$ receptors are located in laminae I-IV of the spinal cord, where primary sensory fibers end. These G-protein coupled receptors activate conductance by $K^+$-selective ion channels and can reduce currents mediated by $Ca^{2+}$ channels in certain neurons. Baclofen has a presynaptic inhibitory effect on the release of excitatory neurotransmitters and also acts postsynaptically to decrease motor neuron firing (see Bowery, *Trends Pharmacol. Sci.* 1989, 10, 401-407; Misgeld et al., *Prog. Neurobiol.* 1995, 46, 423-462, each of which is incorporated herein by reference in its entirety).

Many examples of compounds having agonistic or partially agonistic affinity to $GABA_B$ receptors exist and include certain amino acids, aminophosphonic acids, aminophosphinic acids, aminophosphonous acids, and aminosulfinic acids. Examples of 4-aminobutanoic acid $GABA_B$ receptor ligands include:
4-amino-3-(2-chlorophenyl)butanoic acid;
4-amino-3-(4-fluorophenyl)butanoic acid;
4-amino-3-hydroxybutanoic acid;
4-amino-3-(4-chlorophenyl)-3-hydroxyphenylbutanoic acid;
4-amino-3-(thien-2-yl)butanoic acid;
4-amino-3-(5-chlorothien-2-yl)butanoic acid;
4-amino-3-(5-bromothien-2-yl)butanoic acid;
4-amino-3-(5-methylthien-2-yl)butanoic acid;
4-amino-3-(2-imidazolyl)butanoic acid; and
4-guanidino-3-(4-chlorophenyl)butanoic acid.

Examples of 3-aminopropylsulfinic acid analog $GABA_B$ receptor ligands include:
3-aminopropylsulfinic acid;
(3-amino-2-(4-chlorophenyl)propyl)sulfinic acid;
(3-amino-2-hydroxypropyl)sulfinic acid;
(2S)-(3-amino-2-hydroxypropyl)sulfinic acid;
(2R)-(3-amino-2-hydroxypropyl)sulfinic acid;
(3-amino-2-fluoropropyl)sulfinic acid;
(2S)-(3-amino-2-fluoropropyl)sulfinic acid;
(2R)-(3-amino-2-fluoropropyl)sulfinic acid; and
(3-amino-2-oxopropyl)sulfinic acid.

Certain 3-aminopropylphosphonous and 3-aminopropylphosphinic acid analog $GABA_B$ receptor agonists are described in Froestl et al., *J. Med. Chem.* 1995, 38, 3297-3312; Hall et al., U.S. Pat. No. 5,281,747; Hall et al., U.S. Pat. No. 5,461,040; Hall et al., U.S. Pat. No. 5,567,840; Elebring et al., International Publication No. WO 01/42252; Taylor, International Publication No. WO 02/100869; Taylor, International Publication No. WO 02/100870; Amin et al., International Publication No. WO 02/100871, each of which is incorporated herein by reference in its entirety. Examples of aminopropylphosphonous acid and aminopropylphosphinic analog $GABA_B$ receptor ligands include:
(3-aminopropyl)phosphonous acid;
(4-aminobut-2-yl)phosphonous acid;
(3-amino-2-methylpropyl)phosphonous acid;
(3-aminobutyl)phosphonous acid;
(3-amino-2-(4-chlorophenyl)propyl)phosphonous acid;
(3-amino-2-(4-chlorophenyl)-2-hydroxypropyl)phosphonous acid;
(3-amino-2-(4-fluorophenyl)propyl)phosphonous acid;
(3-amino-2-phenylpropyl)phosphonous acid;
(3-amino-2-hydroxypropyl)phosphonous acid;
(E)-(3-aminopropen-1-yl)phosphonous acid;
(3-amino-2-cyclohexylpropyl)phosphonous acid;
(3-amino-2-benzylpropyl)phosphonous acid;
[3-amino-2-(4-methylphenyl)propyl]phosphonous acid;
[3-amino-2-(4-trifluoromethylphenyl)propyl]phosphonous acid;
[3-amino-2-(4-methoxyphenyl)propyl]phosphonous acid;
[3-amino-2-(4-chlorophenyl)-2-hydroxypropyl]phosphonous acid;
(3-aminopropyl)methylphosphinic acid;
(3-amino-2-hydroxypropyl)methylphosphinic acid;
(3-aminopropyl)(difluoromethyl)phosphinic acid;
(4-aminobut-2-yl)methylphosphinic acid;
(3-amino-1-hydroxypropyl)methylphosphinic acid;
(3-amino-2-hydroxypropyl)(difluoromethyl)phosphinic acid;
(E)-(3-aminopropen-1-yl)methylphosphinic acid;
(3-amino-2-oxo-propyl)methyl phosphinic acid;
(3-aminopropyl)hydroxymethylphosphinic acid;
(5-aminopent-3-yl)methylphosphinic acid; and
(4-amino-1,1,1-trifluorobut-2-yl)methylphosphinic acid.

A principal pharmacological effect of $GABA_B$ receptor agonists in mammals is reduction of muscle tone, and baclofen is frequently used in the treatment of spasticity. Spasticity is associated with damage to the corticospinal tract and is a common complication of neurological disease. Diseases and conditions in which spasticity may be a prominent symptom include cerebral palsy, multiple sclerosis, stroke, head and spinal cord injuries, traumatic brain injury, anoxia and neurodegenerative diseases. Patients with spasticity complain of stiffness, involuntary spasm and pain. These painful spasms may be spontaneous or triggered by a minor sensory stimulus, such as touching the patient.

GABA$_B$ receptor agonists are also useful in controlling gastroesophageal reflux disease (Lidums et al., *Gastroenterology* 2000, 118, 7-13; Cange et al., *Aliment. Pharmacol. Ther.* 2002, 16, 869-873; van Herwaarden et al., *Aliment. Pharmacol. Ther.* 2002, 16, 1655-1662; Zhang et al., *Gut* 2002, 50, 19-24; Vela et al., *Aliment. Pharmacol. Ther.* 2003, 17, 243-251; Koek et al., *Gut* 2003, 52, 1397-1402; Ciccaglione et al., *Gut* 2003, 52, 464-470; Andrews et al., U.S. Pat. No. 6,117,908; Andrews et al., U.S. Pat. No. 6,664,069; Fara et al., International Publication No. WO 02/096404; Fitzpatrick et al., International Publication No. WO 02/100823; Amin et al., and International Publication No. WO 02/100871, each of which is incorporated herein by reference in its entirety). The physiologic process by which most reflux episodes occur is transient lower esophageal sphincter relaxation (TLESR). The lower esophageal sphincter (LES) and crural diaphragm each contribute to the sphincteric mechanism that partitions the stomach from the esophagus and guards against pathological gastroesophageal reflux (GER) (Mittal et al., *Gastroenterology* 1995, 109, 601-610, which is incorporated herein by reference in its entirety). TLESRs are rapid and prolonged relaxations of the LES and inhibitions of the crural diaphragm that are not initiated by swallowing. Gastric distension and elevation of serum cholecystokinin (CCK) after eating increases the frequency of TLESRs, and these transient relaxations are important pathophysiologically as they occur more frequently in patients with gastroesophageal reflux disease (GERD). TLESRs are believed to account for virtually all reflux episodes in healthy individuals and most (up to 80%) episodes in patients with GERD (Tonini et al., *Drugs.* 2004, 64, 347-361, which is incorporated herein by reference in its entirety).

GABA$_B$ receptor agonists are also useful in promoting alcohol abstinence in alcoholics (Gessa et al., International Publication No. WO01/26638, which is incorporated herein by reference in its entirety); in promoting smoking cessation (Gessa et al., International Publication No. WO01/08675, which is incorporated herein by reference in its entirety); in reducing addiction liability of narcotic agents (Robson et al., U.S. Pat. No. 4,126,684, which is incorporated herein by reference in its entirety); in the treatment of emesis (Bountra et al., U.S. Pat. No. 5,719,185, which is incorporated herein by reference in its entirety) and as an anti-tussive for the treatment of cough (Kreutner et al., U.S. Pat. No. 5,006,560, which is incorporated herein by reference in its entirety).

Typical GABA$_B$ receptor agonists such as the zwitterionic 4-aminobutanoic, 3-aminopropylphosphinic, 3-aminopropylphosphonous, and 3-aminopropylsulfinic acids noted above are polar molecules that lack the requisite physicochemical characteristics for effective passive permeability across cellular membranes. For baclofen, passage of the drug across the gastrointestinal tract and the blood-brain barrier (BBB) is mediated primarily by active transport processes, rather than by passive diffusion. Accordingly, baclofen is a substrate for active transport mechanisms shared by neutral α-amino acids such as leucine, and β-amino acids such as β-alanine and taurine (van Bree et al., *Pharm. Res.* 1988, 5, 369-371; Cercos-Fortea et al., *Biopharm. Drug. Disp.* 1995, 16, 563-577; Deguchi et al., *Pharm. Res.* 1995, 12, 1838-1844; Moll-Navarro et al., *J. Pharm. Sci.* 1996, 85, 1248-1254, each of which is incorporated herein by reference in its entirety). 3-Aminopropylphosphonous and 3-aminopropylphosphinic acids are also likely to exploit related active transport mechanisms to permeate the gastrointestinal (GI) mucosa following oral administration.

Another common feature shared by baclofen and other zwitterionic GABA$_B$ receptor agonists is their rapid clearance from the systemic circulation, which leads to the necessity for frequent dosing in humans (e.g. three or four times daily) (see Bowery, supra; "Commercial and Pipeline Perspectives: Upper GI Disorders", Data Monitor Report, September 2004, p. 147). Sustained released oral dosage formulations are a conventional solution to the problem of rapid systemic drug clearance, as is well known in the art (see, e.g., "Remington's Pharmaceutical Sciences," Lippincott Williams & Wilkins, 21 st Edition, 2005). Osmotic delivery systems are also recognized methods for sustained drug delivery (See, e.g., Verma et al., *Drug Dev. Ind. Pharm.* 2000, 26, 695-708). Successful application of these technologies depends on the drug of interest having an effective level of absorption from the large intestine (also referred to herein as the colon), where the dosage form spends a majority of its time during its passage down the gastrointestinal tract. Baclofen is poorly absorbed following administration into the colon in animal models (Merino et al., *Biopharm. Drug. Disp.* 1989, 10, 279-297) presumably because the transporter proteins mediating baclofen absorption in the upper region of the small intestine are not expressed in the large intestine. Development of an oral controlled release formulation for baclofen and other zwitterionic GABA$_B$ receptor agonists should considerably improve the convenience, efficacy and side effect profile of GABA$_B$ agonist therapy. However, the rapid passage of conventional dosage forms through the proximal absorptive region of the small intestine has thus far prevented the successful application of sustained release technologies to this drug. A number of exploratory delivery technologies, which rely on either mucoadhesion or gastric retention have been suggested to achieve sustained delivery of baclofen (Sinnreich, U.S. Pat. No. 4,996,058; Khanna, U.S. Pat. No. 5,091,184; Fara et al., supra; Dudhara et al., International Publication No. WO 03/011255) though to date none of these appear to be able to achieve sustained blood levels of baclofen in human subjects.

Thus, there is a significant need for new prodrugs of 3-aminopropylphosphonous and 3-aminopropylphosphinic acid GABA$_B$ receptor agonists which are well absorbed in the large intestine and/or colon and hence suitable for oral sustained release formulations, thus improving the convenience, efficacy, and side effect profile of GABA$_B$ agonist therapy, particularly for the treatment of spasticity, gastroesophageal reflux disease, drug addiction or abuse, alcohol addiction or abuse, cough, and emesis.

These and other needs may be satisfied by the disclosure herein of acyloxyalkyl carbamate prodrugs of 3-aminopropylphosphonous acid, 3-aminopropylphosphinic acid, and analogs thereof, pharmaceutical compositions comprising acyloxyalkyl carbamate prodrugs of 3-aminopropylphosphonous acid, 3-aminopropylphosphinic acid, and analogs thereof, methods of making acyloxyalkyl carbamate prodrugs of 3-aminopropylphosphonous acid, 3-aminopropylphosphinic acid, and analogs thereof, and methods of using acyloxyalkyl carbamate prodrugs of 3-aminopropylphosphonous acid, 3-aminopropylphosphinic acid, and analogs thereof or pharmaceutical compositions thereof to treat various medical disorders.

In a first aspect, a compound of Formula (I) is provided:

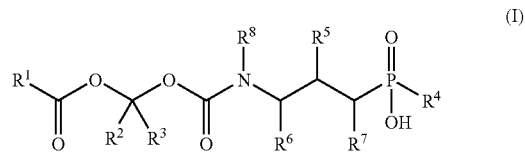

stereoisomers thereof, pharmaceutically acceptable salts of any of the foregoing, pharmaceutically acceptable solvates of any of the foregoing, and combinations of any of the foregoing, wherein:

$R^1$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^2$ and $R^3$ are independently selected from hydrogen, alkyl, substituted alkyl, alkoxycarbonyl, substituted alkoxycarbonyl, aryl, substituted aryl, arylalkyl, substituted arylalkyl, cycloalkyl, substituted cycloalkyl, heteroaryl, substituted heteroaryl, heteroarylalkyl, and substituted heteroarylalkyl, or $R^2$ and $R^3$ together with the carbon atom to which they are bonded form a cycloalkyl, substituted cycloalkyl, cycloheteroalkyl, or substituted cycloheteroalkyl ring;

$R^4$ is selected from hydrogen, methyl, fluoromethyl, difluoromethyl, and trifluoromethyl;

$R^5$ is selected from hydrogen, hydroxy, mercapto, fluoro, oxo, $C_{1-4}$ alkyl, substituted $C_{1-4}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl;

$R^6$ and $R^7$ are independently selected from hydrogen, $C_{1-6}$ alkyl, substituted $C_{1-6}$ alkyl, $C_{1-6}$ alkoxy, substituted $C_{1-6}$ alkoxy, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl; and $R^8$ is selected from hydrogen, $C_{1-6}$ alkyl, substituted $C_{1-6}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl.

In a second aspect, methods of synthesizing a compound of Formula (I) are provided, comprising:

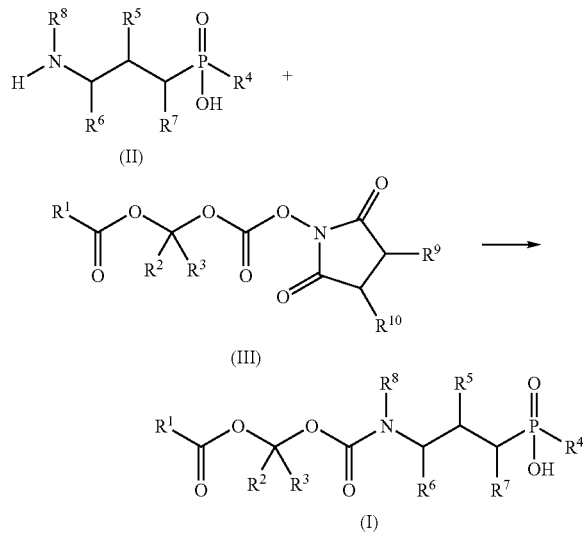

contacting a compound of Formula (II) and a compound of Formula (III), optionally in the presence of a base, wherein:

$R^9$ and $R^{10}$ are independently selected from hydrogen, acylamino, acyloxy, alkoxycarbonylamino, alkoxycarbonyloxy, alkyl, substituted alkyl, alkoxy, substituted alkoxy, aryl, substituted aryl, arylalkyl, carbamoyloxy, dialkylamino, heteroaryl, hydroxy, and sulfonamido, or $R^9$ and $R^{10}$ together with the atoms to which they are bonded form a substituted cycloalkyl, substituted cycloheteroalkyl, or substituted aryl ring; and $R^1$, $R^2$, $R^3$, $R^4$, $R^5$, $R^6$, $R^7$ and $R^8$ are as defined, supra.

In a third aspect, pharmaceutical compositions comprising at least one compound of Formula (I), or pharmaceutically acceptable salts thereof, a solvate of any of the foregoing, and mixtures of any of the foregoing, and a pharmaceutically acceptable vehicle chosen from a diluent, a carrier, an excipient, an adjuvant and mixtures thereof, are provided. The choice of diluent, carrier, excipient and adjuvant will depend upon, among other factors, the desired mode of administration.

In a fourth aspect, methods are provided for treating or preventing gastroesophageal reflux disease. Methods are also provided for treating or preventing spasticity, alcohol abuse or addiction, nicotine abuse or addiction, narcotics abuse or addiction, emesis, and cough. The methods generally involve administering to a patient in need of such treatment or prevention a therapeutically effective amount of a compound of Formula (I) or a pharmaceutical composition thereof.

DEFINITIONS

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the properties sought to be obtained. At the very least, each numerical parameter should at least be construed in light of the number of reported significant digits and by applying ordinary rounding techniques.

Notwithstanding that the numerical ranges and parameters setting forth the broad scope of the embodiments are approximations, the numerical values set forth in the specific examples are reported as precisely as possible. Any numerical values, however, inherently contain certain errors necessarily resulting form the standard deviation found in their respective testing measurements.

The section headings used herein are for organizational purposes only, and are not to be construed as limiting the subject matter disclosed.

To the extent the definitions of terms in the publications, patents, and patent applications incorporated herein by reference are not the same as the definitions set forth in this specification, the definitions in this specification control for the entire specification, including the claims. Any other definitions in the publications, patents, and patent applications incorporated herein by reference that are not explicitly provided in this specification apply only to the embodiments discussed in the publications, patents, and patent applications incorporated herein by reference.

"1-Acyloxy-alkyl carbamate" refers to an N-1-acyloxyalkoxycarbonyl derivative of 3-aminopropylphosphonous acid, 3-aminopropylphosphinic acid, or an analog thereof as encompassed by compounds of Formula (I).

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, and ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In certain embodiments, an alkyl group comprises from 1 to 20 carbon atoms, in certain embodiments, from 1 to 10 carbon atoms, and in certain embodiments, from 1 to 6 carbon atoms.

"Alkanyl" by itself or as part of another substituent refers to a saturated branched, straight-chain or cyclic alkyl radical derived by the removal of one hydrogen atom from a single carbon atom of a parent alkane. Examples of alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Examples of alkenyl groups include, but are not limited to, ethenyl; propenyls such as prop-1-en-1-yl, prop-1-en-2-yl, prop-2-en-1-yl (allyl), prop-2-en-2-yl, and cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Examples of alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl, or heteroarylalkyl as defined herein. Examples include, but are not limited to formyl, acetyl, cyclohexylcarbonyl, cyclohexylmethylcarbonyl, benzoyl, benzylcarbonyl, and the like.

"Alkoxy" by itself or as part of another substituent refers to a radical —OR$^{31}$ where R$^{31}$ represents an alkyl or cycloalkyl group as defined herein. Examples include, but are not limited to, methoxy, ethoxy, propoxy, butoxy, cyclohexyloxy, and the like.

"Alkoxycarbonyl" by itself or as part of another substituent refers to a radical —C(O)OR$^{31}$ where R$^{31}$ represents an alkyl or cycloalkyl group as defined herein. Examples include, but are not limited to, methoxycarbonyl, ethoxycarbonyl, propoxycarbonyl, butoxycarbonyl, cyclohexyloxycarbonyl, and the like.

"3-Aminopropylphosphonous acid analog" refers to a compound of Formula (II):

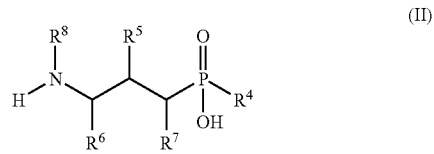

wherein:
R$^4$ is hydrogen;
R$^5$ is selected from hydrogen, hydroxy, mercapto, fluoro, oxo, C$_{1-4}$ alkyl, substituted C$_{1-4}$ alkyl, aryl, substituted aryl, C$_{3-6}$ cycloalkyl, substituted C$_{3-6}$ cycloalkyl, heteroaryl, substituted heteroaryl, C$_{7-9}$ phenylalkyl, and substituted C$_{7-9}$ phenylalkyl;
R$^6$ and R$^7$ are independently selected from hydrogen, C$_{1-6}$ alkyl, substituted C$_{1-6}$ alkyl, C$_{1-6}$ alkoxy, substituted C$_{1-6}$ alkoxy, aryl, substituted aryl, C$_{3-6}$ cycloalkyl, substituted C$_{3-6}$ cycloalkyl, heteroaryl, substituted heteroaryl, C$_{7-9}$ phenylalkyl and substituted C$_{7-9}$ phenylalkyl; and
R$^8$ is selected from hydrogen, C$_{1-6}$ alkyl, substituted C$_{1-6}$ alkyl, aryl, substituted aryl, C$_{3-6}$ cycloalkyl, substituted C$_{3-6}$ cycloalkyl, heteroaryl, substituted heteroaryl, C$_{7-9}$ phenylalkyl, and substituted C$_{7-9}$ phenylalkyl.

Within the scope of this disclosure, it is to be understood that when R$^5$ is an oxo group the bond between R$^5$ and the carbon to which it is bonded is a double bond.

"3-Aminopropylphosphinic acid analog" refers to a compound of Formula (II):

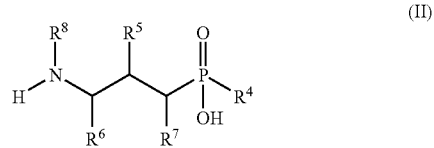

wherein:
R$^4$ is selected from methyl, fluoromethyl, difluoromethyl, and trifluoromethyl;
R$^5$ is selected from hydrogen, hydroxy, mercapto, fluoro, oxo, C$_{1-4}$ alkyl, substituted C$_{1-4}$ alkyl, aryl, substituted aryl, C$_{3-6}$ cycloalkyl, substituted C$_{3-6}$ cycloalkyl, heteroaryl, substituted heteroaryl, C$_{7-9}$ phenylalkyl, and substituted C$_{7-9}$ phenylalkyl;
R$^6$ and R$^7$ are independently selected from hydrogen, C$_{1-6}$ alkyl, substituted C$_{1-4}$ alkyl, C$_{1-6}$ alkoxy, substituted C$_{1-6}$ alkoxy, aryl, substituted aryl, C$_{3-6}$ cycloalkyl, substituted C$_{3-6}$ cycloalkyl, heteroaryl, substituted heteroaryl, C$_{7-9}$ phenylalkyl, and substituted C$_{7-9}$ phenylalkyl; and
R$^8$ is selected from hydrogen, C$_{1-6}$ alkyl, substituted C$_{1-4}$ alkyl, aryl, substituted aryl, C$_{3-6}$ cycloalkyl, substituted C$_{3-6}$ cycloalkyl, heteroaryl, substituted heteroaryl, C$_{7-9}$ phenylalkyl, and substituted C$_{7-9}$ phenylalkyl.

Within the scope of this disclosure, it is to be understood that when R$^5$ is an oxo group the bond between R$^5$ and the carbon to which it is bonded is a double bond.

"Aryl" by itself or as part of another substituent refers to a monovalent aromatic hydrocarbon radical derived by the removal of one hydrogen atom from a single carbon atom of a parent aromatic ring system. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group comprises from 6 to 20 carbon atoms, and in certain embodiments, from 6 to 12 carbon atoms.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl and/or arylalkynyl is used. In certain embodiments, an arylalkyl group is $C_{7-30}$ arylalkyl, e.g., the alkanyl, alkenyl or alkynyl moiety of the arylalkyl group is $C_{1-10}$ and the aryl moiety is $C_{6-20}$, and in certain embodiments, an arylalkyl group is $C_{7-20}$ arylalkyl, e.g., the alkanyl, alkenyl, or alkynyl moiety of the arylalkyl group is $C_{1-8}$ and the aryl moiety is $C_{6-12}$.

"AUC" is the area under a curve representing the concentration of a compound or metabolite thereof in a biological fluid in a patient as a function of time following administration of the compound to the patient. In certain embodiments, the compound can be a prodrug and the metabolite can be a drug. Examples of biological fluids include plasma and blood. The AUC can be determined by measuring the concentration of a compound or metabolite thereof in a biological fluid such as the plasma or blood using methods such as liquid chromatography-tandem mass spectrometry (LC/MS/MS), at various time intervals, and calculating the area under the plasma concentration-versus-time curve. Suitable methods for calculating the AUC from a drug concentration-versus-time curve are well known in the art. As relevant to the disclosure here, an AUC for 3-aminopropylphosphonous acid, 3-aminopropylphosphinic acid, or an analog thereof can be determined by measuring the concentration of 3-aminopropylphosphonous acid, 3-aminopropylphosphinic acid, or an analog thereof in the plasma or blood of a patient following oral administration of a compound of Formula (I) to the patient.

"Bioavailability" refers to the rate and amount of a drug that reaches the systemic circulation of a patient following administration of the drug or prodrug thereof to the patient and can be determined by evaluating, for example, the plasma or blood concentration-versus-time profile for the drug. Parameters useful in characterizing a plasma or blood concentration-versus-time curve include the area under the curve (AUC), the time to peak concentration ($T_{max}$), and the maximum drug concentration ($C_{max}$).

"Bioequivalence" refers to equivalence of the rate and extent of absorption of a drug after administration of equal doses of the drug or prodrug to a patient. As used herein, two plasma or blood concentration profiles are bioequivalent if the 90% confidence interval for the ratio of the mean response of the two profiles is within the limits of 0.8 and 1.25. The mean response includes at least one of the characteristic parameters of a profile such as $C_{max}$, $T_{max}$, and AUC.

"$C_{max}$" is the maximum concentration of a drug in the plasma or blood of a patient following administration of a dose of the drug or prodrug to the patient.

"$T_{max}$" is the time to the maximum concentration ($C_{max}$) of a drug in the plasma or blood of a patient following administration of a dose of the drug or prodrug to the patient.

"Compounds of the present disclosure" refers to compounds encompassed by structural Formula (I) disclosed herein and includes specific compounds disclosed herein encompassed by Formula (I). Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers, or diastereomers. Accordingly, the chemical structures disclosed herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form, and mixtures thereof. Accordingly, the chemical structures depicted herein encompass all possible tautomeric forms of the illustrated compounds. The disclosed compounds described also include isotopically labeled compounds where one or more atoms have an atomic mass different from the atomic mass conventionally found in nature. Examples of isotopes that may be incorporated into the compounds of the present include, but are not limited to, $^2H$, $^3H$, $^{11}C$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated, or N-oxides. Certain compounds may exist in multiple crystalline or amorphous forms. In general, all physical forms are equivalent for the uses contemplated herein and are intended to be within the scope of the present disclosure. Further, when partial structures of the compounds are illustrated, brackets indicate the point of attachment of the partial structure to the rest of the molecule.

"Corresponding prodrug of 3-aminopropylphosphonous acid, 3-aminopropylphosphinic acid, or analog thereof" refers to a compound of Formula (I) having the same $R^4$, $R^5$, $R^6$, $R^7$, and $R^8$ substituents as the 3-aminopropylphosphonous acid, 3-aminopropylphosphinic acid, or analog thereof of Formula (II). Likewise, the "corresponding 3-aminopropylphosphonous acid, 3-aminopropylphosphinic acid, or analog thereof" refers to a compound of Formula (II) having the same $R^4$, $R^5$, $R^6$, $R^7$, and $R^8$ substituents as the prodrug of 3-aminopropylphosphonous acid, 3-aminopropylphosphinic acid, or analog thereof of Formula (I). A compound of Formula (II) can have one or more corresponding prodrugs of Formula (I). A prodrug of Formula (I) will have a single corresponding 3-aminopropylphosphonous acid, 3-aminopropylphosphinic acid, or analog thereof of Formula (II).

"Cycloalkoxycarbonyl" by itself or as part of another substituent refers to a radical —C(O)OR$^{36}$ where R$^{36}$ represents an cycloalkyl group as defined herein. Examples include, but are not limited to, cyclobutyloxycarbonyl, cyclohexyloxycarbonyl, and the like.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, the cycloalkyl group is $C_{3-10}$ cycloalkyl, and in certain embodiments, $C_{3-7}$ cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Examples of heteroatoms to replace a carbon atom(s) include, but are not limited to, N, P, O, S, Si, etc. Where a specific level of saturation is intended, the nomenclature "cycloheteroalkanyl" or "cycloheteroalkenyl" is used. Cycloheteroalkyl groups include, but are not limited to, groups derived from epoxides, azirines, thiiranes, imidazolidine, morpholine, piperazine, piperidine, pyrazolidine, pyrrolidine, quinuclidine, and the like.

"Heteroalkyl, heteroalkanyl, heteroalkenyl, and heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Examples of heteroatomic groups which can be included in these groups include, but are not limited to, —O—, —S—, —O—O—, —S—S—, —O—S—, —NR$^{37}$R$^{38}$—, =N—N—, —N=N—, —N=N—NR$^{39}$R$^{40}$, —PR$^{41}$—, —P(O)$_2$—, —POR$^{42}$—, —O—P(O)$_2$—, —SO—, —SO$_2$—, —SnR$^{43}$R$^{44}$—, and the like, where R$^{37}$, R$^{38}$, R$^{39}$, R$^{40}$, R$^{41}$, R$^{42}$, R$^{43}$, and R$^{44}$ are independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl.

"Heteroaryl" by itself or as part of another substituent, refers to a monovalent heteroaromatic radical derived by the removal of one hydrogen atom from a single atom of a parent heteroaromatic ring system. Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5-20 membered heteroaryl, and in certain embodiments, from 5-10 membered heteroaryl. In certain embodiments, heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In certain embodiments, a heteroarylalkyl group is a 6-30 membered heteroarylalkyl, e.g., the alkanyl, alkenyl, or alkynyl moiety of the heteroarylalkyl is 1-10 membered and the heteroaryl moiety is a 5-20-membered heteroaryl, and in certain embodiments, 6-20 membered heteroarylalkyl, e.g., the alkanyl, alkenyl, or alkynyl moiety of the heteroarylalkyl is 1-8 membered and the heteroaryl moiety is a 5-12-membered heteroaryl.

"Immediately preceding embodiments" refers to the embodiments disclosed in the paragraph.

"Parent aromatic ring system" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Patient" refers to a mammal, for example, a human.

"Pharmaceutically acceptable" refers to approved or approvable by a regulatory agency of the Federal or state government or listed in the U.S. Pharmacopoeia or other generally recognized pharmacopoeia for use in animals and more particularly in humans.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like.

"Pharmaceutically acceptable vehicle" refers to a diluent, adjuvant, excipient, or carrier with which a compound is administered.

"Pharmaceutical composition" refers to at least one compound and a at least one pharmaceutically acceptable vehicle, with which the at least one compound is administered to a patient.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Compounds of Formula (I) are prodrugs that can be metabolized within a patient's body to form the parent drug, e.g., 3-aminopropylphosphonous acid, 3-aminopropylphosphinic acid, or an analog thereof having Formula (II), and hence compounds of Formula (I) are prodrugs of 3-aminopropylphosphonous acid, 3-aminopropylphosphinic acid, or an analog thereof having Formula (II). Compounds of Formula (I) include pharmaceutically acceptable salts thereof, or pharmaceutically acceptable solvates of the free acid form of any of the foregoing, as well as crystalline forms of any of the foregoing. Prodrugs are frequently, although not necessarily, pharmacologically inactive until converted to the parent drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms, which when bonded to a reactive functional group in a molecule masks, reduces or prevents reactivity of the functional group. Examples of protecting groups can be found in Green et al., "Protective Groups in Organic Chemistry," (Wiley, $2^{nd}$ ed. 1991) and Harrison et al., "Compendium of Synthetic Organic Methods," Vols. 1-8 (John Wiley and Sons, 1971-1996). Examples of amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl ("FMOC"), nitro-veratryloxycarbonyl (NVOC), and the like. Examples of hydroxy protecting groups include, but are not limited to, those where the hydroxy group is either acylated or alkylated such as benzyl, and trityl ethers as well as alkyl ethers, tetrahydropyranyl ethers, trialkylsilyl ethers, and allyl ethers.

"Solvate" refers to a molecular complex of a compound with one or more solvent molecules in a stoichiometric or non-stoichiometric amount. Such solvent molecules are those commonly used in the pharmaceutical art, which are known to be innocuous to a recipient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a complex where the one or more solvent molecules are water.

"Stereoisomers" refers to isomers that differ in the arrangement of the constituent atoms in space, and includes enantiomers and diastereomers. Stereoisomers that are mirror images of each other and optically active are termed "enantiomers," and stereoisomers that are not mirror images of one another are termed "diastereoisomers."

"Sustained release" refers to release of a compound of Formula (I) from a dosage form at a rate effective to achieve a therapeutic or prophylactic concentration of the compound of Formula (I), or active metabolite thereof, in the systemic blood circulation over a prolonged period of time relative to that achieved by oral administration of an immediate release formulation of the compound of Formula (I). In some embodiments, release of a compound of Formula (I) occurs over a time period of at least about 4 hours, such as at least about 8 hours, in some embodiments, at least about 12 hours, at least about 16 hours, at least bout 20 hours, and in some embodiments, at least about 24 hours.

"Substantially one diastereomer" refers to a compound containing two or more stereogenic centers such that the diastereomeric excess (d.e.) of the compound is at least about 90%. The diastereomeric excess is the ratio of the percentage of one diastereomer in a mixture to that of another diastereomer. In some embodiments, the diastereomeric excess is, for example, at least about 91%, at least about 92%, at least about 93%, at least about 94%, at least about 95%, at least about 96%, at least about 97%, at least about 98%, or at least about 99%.

"Substituted" refers to a group in which one or more hydrogen atoms are independently replaced with the same or different substituent(s). Typical substituents include, but are not limited to, -M, $-R^{60}$, $-O^-$, =O, $-OR^{60}$, $-SR^{60}$, $-S^-$, =S, $-NR^{60}R^{61}$, =$NR^{60}$, $-CF_3$, $-CN$, $-OCN$, $-SCN$, $-NO$, $-NO_2$, =$N_2$, $-N_3$, $-S(O)_2O^-$, $-S(O)_2OH$, $-S(O)_2R^{60}$, $-OS(O_2)O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-C(S)OR^{60}$, $-NR^{62}C(O)NR^{60}R^{61}$, $-NR^{62}C(S)NR^{60}R^{61}$, $-NR^{62}C(NR^{63})NR^{60}R^{61}$, and $-C(NR^{62})NR^{60}R^{61}$ where M is independently a halogen; $R^{60}$, $R^{61}$, $R^{62}$, and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl, or substituted heteroaryl, or $R^{60}$ and $R^{61}$ together with the nitrogen atom to which they are bonded form a cycloheteroalkyl or substituted cycloheteroalkyl ring. In certain embodiments, substituents include -M, $-R^{60}$, =O, $-OR^{60}$, $-SR^{60}$, $-S^-$, =S, $-NR^{60}R^{61}$, =$NR^{60}$, $-CF_3$, $-CN$, $-OCN$, $-SCN$, $-NO$, $-NO_2$, =$N_2$, $-N_3$, $-S(O)_2R^{60}$, $-OS(O_2)O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, and $-NR^{62}C(O)NR^{60}R^{61}$, in certain embodiments, -M, $-R^{60}$, =O, $-OR^{60}$, $-SR^{60}$, $-NR^{60}R^{61}$, $-CF_3$, $-CN$, $-NO_2$, $-S(O)_2R^{60}$, $-P(O)(OR^{60})(O^-)$, $-OP(O)(OR^{60})(OR^{61})$, $-C(O)R^{60}$, $-C(O)OR^{60}$, $-C(O)NR^{60}R^{61}$, and $-C(O)O^-$, and in certain embodiments, -M, $-R^{60}$, =O, $-OR^{60}$, $-SR^{60}$, $-NR^{60}R^{61}$, $-CF_3$, $-CN$, $-NO_2$, $-S(O)_2R^{60}$, $-OP(O)(OR^{60})(OR^{61})$, $-C(O)R^{60}$, $-(O)OR^{60}$, and $-C(O)O^-$, where $R^{60}$, $R^{61}$, and $R^{62}$ are as defined above.

"Treating" or "treatment" of any disease or disorder refers, in some embodiments, to ameliorating at least one disease or disorder (i.e., arresting or reducing the development of the disease or at least one of the clinical symptoms thereof). In certain embodiments "treating" or "treatment" refers to ameliorating at least one physical parameter, which may or may not be discernible by the patient. In certain embodiments, "treating" or "treatment" refers to inhibiting the disease or disorder, either physically, (e.g., stabilization of a discernible symptom), physiologically, (e.g., stabilization of a physical parameter), or both. In certain embodiments, "treating" or "treatment" refers to delaying the onset of the disease or disorder.

"Therapeutically effective amount" means the amount of a compound that, when administered to a patient for treating or preventing a disease, is sufficient to effect such treatment or prevention of the disease. The "therapeutically effective amount" will vary depending on the compound, the disease and its severity and the age, weight, etc., of the patient having the disease to be treated or prevented.

Reference will now be made in detail to particular embodiments of compounds and methods. The disclosed embodiments are not intended to be limiting of the claims. To the contrary, the claims are intended to cover all alternatives, modifications, and equivalents.

Compounds

Certain embodiments provide a compound of Formula (I):

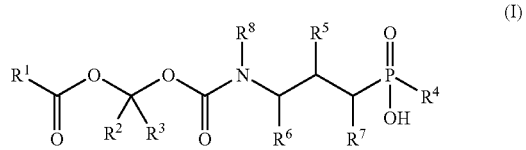

stereoisomers thereof, pharmaceutically acceptable salts of any of the foregoing, pharmaceutically acceptable solvates of any of the foregoing, and combinations of any of the foregoing, wherein:

$R^1$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^2$ and $R^3$ are independently selected from hydrogen, alkyl, substituted alkyl, alkoxycarbonyl, substituted alkoxycarbonyl, aryl, substituted aryl, arylalkyl, substituted arylalkyl, cycloalkyl, substituted cycloalkyl, heteroaryl, substituted heteroaryl, heteroarylalkyl, and substituted heteroarylalkyl, or $R^2$ and $R^3$ together with the carbon atom to which they are bonded form a cycloalkyl, substituted cycloalkyl, cycloheteroalkyl, or substituted cycloheteroalkyl ring;

$R^4$ is selected from hydrogen, methyl, fluoromethyl, difluoromethyl, and trifluoromethyl;

$R^5$ is selected from hydrogen, hydroxy, mercapto, fluoro, oxo, $C_{1-4}$ alkyl, substituted $C_{1-4}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl;

$R^6$ and $R^7$ are independently selected from hydrogen, $C_{1-6}$ alkyl, substituted $C_{1-6}$ alkyl, $C_{1-6}$ alkoxy, substituted $C_{1-6}$ alkoxy, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl; and $R^8$ is selected from hydrogen, $C_{1-6}$ alkyl, substituted $C_{1-6}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl.

Within the scope of this disclosure, it is to be understood that when $R^5$ is an oxo group the bond between $R^5$ and the carbon to which it is bonded is a double bond.

In certain embodiments, each of $R^6$, $R^7$ and $R^8$ is hydrogen.

In certain embodiments, $R^4$ is selected from hydrogen and methyl. In certain embodiments, $R^4$ is hydrogen.

In certain embodiments, $R^4$ is methyl.

In certain embodiments, $R^5$ is selected from hydrogen, hydroxy, fluoro, oxo, phenyl, 4-chlorophenyl, 4-fluorophenyl, 4-trifluoromethylphenyl, cyclohexyl, and benzyl.

In certain embodiments, and each of $R^6$, $R^7$, and $R^8$ is hydrogen.

In certain embodiments, $R^4$ is selected from hydrogen and methyl, $R^5$ is selected from hydrogen, hydroxy, fluoro, oxo, and 4-chlorophenyl, and each of $R^6$, $R^7$, and $R^1$ is hydrogen. In certain embodiments, $R^4$ is hydrogen, $R^5$ is selected from hydrogen, hydroxy, fluoro, oxo, and 4-chlorophenyl, and each of $R^6$, $R^7$, and $R^8$ is hydrogen. In certain embodiments, $R^4$ is methyl, $R^5$ is selected from hydrogen, hydroxy, fluoro, oxo, and 4-chlorophenyl, and each of $R^6$, $R^7$, and $R^8$ is hydrogen.

In certain embodiments of compounds of Formula (I) in which $R^4$ is hydrogen, and each of $R^6$, $R^7$, and $R^8$ is hydrogen, $R^5$ is hydrogen, in certain embodiments, $R^5$ is oxo, in certain embodiments, $R^5$ is hydroxy, in certain embodiments, $R^5$ is fluoro, and in certain embodiments. $R^5$ is 4-chlorophenyl. In certain embodiments of compounds of Formula (I) in which $R^4$ is methyl, and each of $R^6$, $R^7$, and $R^8$ is hydrogen, $R^5$ is hydrogen, in certain embodiments, $R^5$ is oxo, in certain embodiments, $R^5$ is hydroxy, in certain embodiments, $R^5$ is fluoro, and in certain embodiments. $R^5$ is 4-chlorophenyl. In certain embodiments of compounds of Formula (I), the carbon to which $R^5$ is bonded is of the R configuration. In certain embodiments of compounds of Formula (I), the carbon to which $R^5$ is bonded is of the S configuration.

In certain embodiments of compounds of Formula (I), $R^1$ is selected from $C_{1-6}$ alkyl, substituted $C_{1-6}$ alkyl, $C_{3-6}$ cycloalkyl, substituted $C_{3-6}$ cycloalkyl, phenyl, substituted phenyl, $C_{7-9}$ phenylalkyl, and pyridyl. In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl. In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl.

In certain embodiments of compounds of Formula (I), $R^2$ and $R^3$ are independently selected from hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl, and substituted heteroarylalkyl. In certain embodiments of compounds of Formula (I), $R^2$ and $R^3$ are independently selected from hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl, and pyridyl. In certain embodiments of compounds of Formula (I), $R^2$ and $R^3$ are independently selected from hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl, and 4-pyridyl. In certain embodiments of compounds of Formula (I), $R^2$ is selected from hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl, and 4-pyridyl, and $R^3$ is hydrogen. In certain embodiments of compounds of Formula (I), $R^2$ is selected from hydrogen, methyl, ethyl, n-propyl, isopropyl, n-butyl, isobutyl, sec-butyl, phenyl, and cyclohexyl, and $R^3$ is hydrogen. In certain embodiments of compounds of Formula (I), $R^2$ is selected from methyl, methoxycarbonyl, ethoxycarbonyl, isopropoxycarbonyl, and cyclohexyloxycarbonyl, and $R^3$ is methyl.

In certain embodiments of compounds of Formula (I), $R^2$ and $R^3$ together with the carbon atom to which they are bonded form a cycloalkyl, substituted cycloalkyl, cycloheteroalkyl, or substituted cycloheteroalkyl ring. In certain embodiments of compounds of Formula (I), $R^2$ and $R^3$ together with the carbon atom to which they are bonded form a cyclobutyl, cyclopentyl, or cyclohexyl ring.

In certain embodiments of compounds of Formula (I), $R^1$ is selected from $C_{1-6}$ alkyl, substituted $C_{1-6}$ alkyl, $C_{3-6}$ cycloalkyl, phenyl, substituted phenyl, $C_{7-9}$ phenylalkyl, and pyridyl, and $R^2$ and $R^3$ are independently selected from hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl, and pyridyl. In certain embodiments of compounds of Formula (I) in which $R^2$ and $R^3$ are independently selected from hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl, and pyridyl, $R^1$ is selected from methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl, and in certain embodiments, $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl. In certain of the immediately preceding embodiments of compounds of Formula (I), $R^4$ is selected from hydrogen and methyl, and $R^5$ is selected from hydrogen, hydroxy, fluoro, oxo, and 4-chlorophenyl.

In certain embodiments of compounds of Formula (I), $R^1$ is selected from $C_{1-6}$ alkyl, substituted $C_{1-6}$ alkyl, $C_{3-6}$ cycloalkyl, phenyl, substituted phenyl, $C_{7-9}$ phenylalkyl, and pyridyl, and $R^2$ and $R^3$ are independently selected from hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl, and 4-pyridyl. In certain embodiments of compounds of Formula (I) in which $R^2$ and $R^3$ are independently selected from hydrogen, methyl, ethyl, n-propyl, isopropyl, n-butyl, isobutyl, sec-butyl, tert-butyl, cyclopentyl, cyclohexyl, methoxycarbonyl, ethoxycarbonyl, isopropoxycarbonyl, cyclohexyloxycarbonyl, phenyl, benzyl, phenethyl, 2-pyridyl, 3-pyridyl, and 4-pyridyl, $R^1$ is selected from methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl, and in certain embodiments, $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl. In certain of the immediately preceding embodiments of compounds of Formula (I), $R^4$ is selected from hydrogen and methyl, $R^5$ is selected from hydrogen, hydroxy, fluoro, oxo, and 4-chlorophenyl, and each of $R^6$, $R^7$, and $R^8$ is hydrogen.

In certain embodiments of compounds of Formula (I), $R^1$ is selected from $C_{1-6}$ alkyl, substituted $C_{1-6}$ alkyl, $C_{3-6}$ cycloalkyl, phenyl, substituted phenyl, $C_{7-9}$ phenylalkyl, and pyridyl, $R^2$ is selected from hydrogen, methyl, ethyl, n-propyl, isopropyl, n-butyl, isobutyl, sec-butyl, phenyl, and cyclohexyl, and $R^3$ is hydrogen. In certain embodiments of compounds of Formula (I) in which $R^2$ is selected from hydrogen, methyl, ethyl, n-propyl, isopropyl, n-butyl, isobutyl, sec-butyl, phenyl, and cyclohexyl, and $R^3$ is hydrogen, $R^1$ is selected from methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl, and in certain embodiments, $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl. In certain of the immediately preceding embodiments of compounds of Formula (I), $R^4$ is selected from hydrogen and methyl, $R^5$ is selected from hydrogen, hydroxy, fluoro, oxo, and 4-chlorophenyl, and each of $R^6$, $R^7$, and $R^8$ is hydrogen. In certain of the immediately preceding embodiments of compounds of Formula (I), $R^4$ is methyl, $R^5$ is selected from hydrogen, hydroxy, fluoro, oxo, and 4-chlorophenyl, and each of $R^6$, $R^7$, and $R^8$ is hydrogen.

In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, $R^2$ is selected from methyl, n-propyl, and isopropyl, $R^3$ is hydrogen, $R^4$ is selected from hydrogen and methyl, $R^5$ is selected from hydrogen, hydroxy, fluoro, oxo, and 4-chlorophenyl, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, $R^2$ is selected from methyl, n-propyl, and isopropyl, $R^3$ is hydrogen, $R^4$ is hydrogen, $R^5$ is selected from hydrogen, hydroxy, fluoro, oxo, and 4-chlorophenyl, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl, $R^2$ is selected from methyl, n-propyl, and isopropyl, $R^3$ is hydrogen, $R^4$ is methyl, $R^5$ is selected from hydrogen, hydroxy, fluoro, oxo, and 4-chlorophenyl, and each of $R^6$, $R^7$, and $R^8$ is hydrogen. In certain of the immediately preceding embodiments, a compound of Formula (I) is substantially one diastereomer. In certain of the immediately preceding embodiments of compounds of Formula (I), the carbon to which $R^2$ and $R^3$ are bonded is of the R configuration. In certain of the immediately preceding embodiments of compounds of Formula (I), the carbon to which $R^2$ and $R^3$ are bonded is of the S configuration.

In certain embodiments of compounds of Formula (I), $R^1$ is selected from $C_{1-6}$ alkyl, substituted $C_{1-6}$ alkyl, $C_{3-6}$ cycloalkyl, phenyl, substituted phenyl, $C_{7-9}$ phenylalkyl, and pyridyl, $R^2$ is selected from methyl, methoxycarbonyl, ethoxycarbonyl, isopropoxy carbonyl, and cyclohexyloxycarbonyl, and $R^3$ is methyl. In certain embodiments of compounds of Formula (I) in which $R^2$ is selected from methyl, methoxycarbonyl, ethoxycarbonyl, isopropoxycarbonyl, and cyclohexyloxycarbonyl, and $R^3$ is methyl, $R^1$ is selected from methyl, ethyl, n-propyl, isopropyl, n-butyl, isobutyl, sec-butyl, tert-butyl, n-pentyl, isopentyl, sec-pentyl, neopentyl, 1,1-dimethoxyethyl, 1,1-diethoxyethyl, phenyl, 4-methoxyphenyl, benzyl, phenethyl, styryl, cyclopropyl, cyclobutyl, cyclopentyl, cyclohexyl, 2-pyridyl, 3-pyridyl, and 4-pyridyl, and in certain embodiments, $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, and 3-pyridyl. In certain of the immediately preceding embodiments of compounds of Formula (I), $R^4$ is selected from hydrogen and methyl, $R^5$ is selected from hydrogen, hydroxy, fluoro, oxo, and 4-chlorophenyl, and each of $R^6$, $R^7$, and $R^8$ is hydrogen.

In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, and 4-pyridyl, $R^2$ is selected from hydrogen, methyl, ethyl, n-propyl, isopropyl, n-butyl, isobutyl, sec-butyl, phenyl, and cyclohexyl, $R^3$ is hydrogen, $R^4$ is selected from hydrogen and methyl, $R^5$ is hydrogen, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, and 4-pyridyl, $R^2$ is selected from hydrogen, methyl, n-propyl, and isopropyl, $R^3$ is hydrogen, $R^4$ is selected from hydrogen and methyl, $R^5$ is hydrogen, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is selected from hydrogen, methyl, n-propyl, and isopropyl, $R^3$ is hydrogen, $R^4$ is selected from hydrogen and methyl, $R^5$ is hydrogen, and each of $R^6$, $R^7$, and $R^8$ is hydrogen.

In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, and 4-pyridyl, $R^2$ is selected from methyl, methoxycarbonyl, ethoxycarbonyl, isopropoxycarbonyl, and cyclohexyloxycarbonyl, $R^3$ is methyl, $R^4$ is selected from hydrogen and methyl, $R^5$ is hydrogen, and each of $R^6$, $R^7$, and $R^8$ is hydrogen.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is hydrogen, $R^3$ is hydrogen, $R^4$ is selected from hydrogen and methyl, $R^5$ is selected from hydrogen, hydroxy, fluoro, oxo, and 4-chlorophenyl, and each of $R^6$, $R^7$, and $R^8$ is hydrogen.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is hydrogen, $R^3$ is hydrogen, $R^4$ is hydrogen, $R^5$ is selected from hydrogen, hydroxy, fluoro, oxo, and 4-chlorophenyl, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is hydrogen, $R^3$ is hydrogen, $R^4$ is methyl, $R^5$ is selected from hydrogen, hydroxy, fluoro, oxo, and 4-chlorophenyl, and each of $R^6$, $R^7$, and $R^8$ is hydrogen.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is hydrogen, $R^3$ is hydrogen, $R^4$ is hydrogen, $R^5$ is hydrogen, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is hydrogen, $R^3$ is hydrogen, $R^4$ is methyl, $R^5$ is hydrogen, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is hydrogen, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is hydrogen, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is hydrogen, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is hydrogen, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is hydrogen, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is hydrogen, and each of $R^6$, $R^7$, and $R^8$ is hydrogen.

In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl or 4-pyridyl, $R^2$ is selected from hydrogen, methyl, ethyl, n-propyl, isopropyl, n-butyl, isobutyl, sec-butyl, phenyl, and cyclohexyl, $R^3$ is hydrogen, $R^4$ is selected from hydrogen and methyl, $R^5$ is hydroxy, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, and 4-pyridyl, $R^2$ is selected from hydrogen, methyl, n-propyl, and isopropyl, $R^3$ is hydrogen, $R^4$ is selected from hydrogen and methyl, $R^5$ is hydroxy, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is selected from hydrogen, methyl, n-propyl, and isopropyl, $R^3$ is hydrogen, $R^4$ is selected from hydrogen and methyl, $R^5$ is hydroxy, and each of $R^6$, $R^7$, and $R^8$ is hydrogen. In certain of the immediately preceding embodiments of compounds of Formula (I), the carbon to which $R^5$ is bonded is of the R configuration. In certain of the immediately preceding embodiments of compounds of Formula (I), the carbon to which $R^5$ is bonded is of the S configuration.

In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, and 4-pyridyl, $R^2$ is selected from methyl, methoxycarbonyl, ethoxycarbonyl, isopropoxycarbonyl, and cyclohexyloxycarbonyl, $R^3$ is methyl, $R^4$ is selected from hydrogen and methyl, $R^5$ is hydroxy, and each of $R^6$, $R^7$, and $R^8$ is hydrogen. In certain of the immediately preceding embodiments of compounds of Formula (I), the carbon to which $R^5$ is bonded is of the R configuration. In certain of the immediately preceding embodiments of compounds of Formula (I), the carbon to which $R^5$ is bonded is of the S configuration.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is hydrogen, $R^3$ is hydrogen, $R^4$ is hydrogen, $R^5$ is hydroxy, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is hydrogen, $R^3$ is hydrogen, $R^4$ is methyl, $R^5$ is hydroxy, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is hydroxy, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is hydroxy, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is hydroxy, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is hydroxy, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is hydroxy, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is hydroxy, and each of $R^6$, $R^7$, and $R^8$ is hydrogen. In certain of the immediately preceding embodiments of compounds of Formula (I), the carbon to which $R^5$ is bonded is of the R configuration. In certain of the immediately preceding embodiments of compounds of Formula (I), the carbon to which $R^5$ is bonded is of the S configuration.

In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, and 4-pyridyl, $R^2$ is selected from hydrogen, methyl, ethyl, n-propyl, isopropyl, n-butyl, isobutyl, sec-butyl, phenyl, and cyclohexyl, $R^3$ is hydrogen, $R^4$ is selected from hydrogen and methyl, $R^5$ is fluoro, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, and 4-pyridyl, $R^2$ is selected from hydrogen, methyl, n-propyl, and isopropyl, $R^3$ is hydrogen, $R^4$ is selected from hydrogen and methyl, $R^5$ is fluoro, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is selected from hydrogen, methyl, n-propyl, and isopropyl, $R^3$ is hydrogen, $R^4$ is selected from hydrogen and methyl, $R^5$ is fluoro, and each of $R^6$, $R^7$, and $R^1$ is hydrogen. In certain of the immediately preceding embodiments of compounds of Formula (I), the carbon to which $R^5$ is bonded is of the R configuration. In certain of the immediately preceding embodiments of compounds of Formula (I), the carbon to which $R^5$ is bonded is of the S configuration.

In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, and 4-pyridyl, $R^2$ is selected from methyl, methoxycarbonyl, ethoxycarbonyl, isopropoxycarbonyl, and cyclohexyloxycarbonyl, $R^3$ is methyl, $R^4$ is selected from hydrogen and methyl, $R^5$ is fluoro, and each of $R^6$, $R^7$, and $R^B$ is hydrogen. In certain of the immediately preceding embodiments of compounds of Formula (I), the carbon to which $R^5$ is bonded is of the R configuration. In certain of the immediately preceding embodiments of compounds of Formula (I), the carbon to which $R^5$ is bonded is of the S configuration.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is hydrogen, $R^3$ is hydrogen, $R^4$ is hydrogen, $R^5$ is fluoro, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is hydrogen, $R^3$ is hydrogen, $R^4$ is methyl, $R^5$ is fluoro, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is fluoro, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is fluoro, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is fluoro, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is fluoro, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is fluoro, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is fluoro, and each of $R^6$, $R^7$, and $R^8$ is hydrogen. In certain of the immediately preceding embodiments of compounds of Formula (I), the carbon to which $R^5$ is bonded is of the R configuration. In certain of the immediately preceding embodiments of compounds of Formula (I), the carbon to which $R^5$ is bonded is of the S configuration.

In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, and 4-pyridyl, $R^2$ is selected from hydrogen, methyl, ethyl, n-propyl, isopropyl, n-butyl, isobutyl, sec-butyl, phenyl, and cyclohexyl, $R^3$ is hydrogen, $R^4$ is selected from hydrogen and methyl, $R^5$ is oxo, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, and 4-pyridyl, $R^2$ is selected from hydrogen, methyl, n-propyl, and isopropyl, $R^3$ is hydrogen, $R^4$ is selected from hydrogen and methyl, $R^5$ is oxo, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is selected from hydrogen, methyl, n-propyl, and isopropyl, $R^3$ is hydrogen, $R^4$ is selected from hydrogen and methyl, $R^5$ is oxo, and each of $R^6$, $R^7$, and $R^8$ is hydrogen.

In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, and 4-pyridyl, $R^2$ is selected from methyl, methoxycarbonyl, ethoxycarbonyl, isopropoxycarbonyl, and cyclohexyloxycarbonyl, $R^3$ is methyl, $R^4$ is selected from hydrogen and methyl, $R^5$ is oxo, and each of $R^6$, $R^7$, and $R^8$ is hydrogen.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is hydrogen, $R^3$ is hydrogen, $R^4$ is hydrogen, $R^5$ is oxo, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is hydrogen, $R^3$ is hydrogen, $R^4$ is methyl, $R^5$ is oxo, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is oxo, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is oxo, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is oxo, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is oxo, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is oxo, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is oxo, and each of $R^6$, $R^7$, and $R^8$ is hydrogen.

In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, and 4-pyridyl, $R^2$ is selected from hydrogen, methyl, ethyl, n-propyl, isopropyl, n-butyl, isobutyl, sec-butyl, phenyl, and cyclohexyl, $R^3$ is hydrogen, $R^4$ is selected from hydrogen and methyl, $R^5$ is 4-chlorophenyl, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, and 4-pyridyl, $R^2$ is selected from hydrogen, methyl, n-propyl, and isopropyl, $R^3$ is hydrogen, $R^4$ is selected from hydrogen and methyl, $R^5$ is 4-chlorophenyl, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is selected from hydrogen, methyl, n-propyl, and isopropyl, $R^3$ is hydrogen, $R^4$ is selected from hydrogen and methyl, $R^5$ is 4-chlorophenyl, and each of $R^6$, $R^7$, and $R^8$ is hydrogen. In certain of the immediately preceding embodiments of compounds of Formula (I), the carbon to which $R^5$ is bonded is of the R configuration. In certain of the immediately preceding embodiments of compounds of Formula (I), the carbon to which $R^5$ is bonded is of the S configuration.

In certain embodiments of compounds of Formula (I), $R^1$ is selected from methyl, ethyl, n-propyl, isopropyl, n-butyl, isobutyl, sec-butyl, tert-butyl, n-pentyl, isopentyl, sec-pentyl, neopentyl, 1,1-diethoxyethyl, phenyl, cyclohexyl, 2-pyridyl, 3-pyridyl, and 4-pyridyl, $R^2$ is selected from methyl, methoxycarbonyl, ethoxycarbonyl, isopropoxycarbonyl, and cyclohexyloxycarbonyl, $R^3$ is methyl, $R^4$ is selected from hydrogen and methyl, $R^5$ is 4-chlorophenyl, and each of $R^6$, $R^7$, and $R^8$ is hydrogen. In certain of the immediately preceding embodiments of compounds of Formula (I), the carbon to which $R^5$ is bonded is of the R configuration. In certain of the immediately preceding embodiments of compounds of Formula (I), the carbon to which $R^5$ is bonded is of the S configuration.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is hydrogen, $R^3$ is hydrogen, $R^4$ is hydrogen, $R^5$ is 4-chlorophenyl, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is hydrogen, $R^3$ is hydrogen, $R^4$ is methyl, $R^5$ is 4-chlorophenyl, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is 4-chlorophenyl, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is 4-chlorophenyl, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is 4-chlorophenyl, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is 4-chlorophenyl, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is 4-chlorophenyl, and each of $R^6$, $R^7$, and $R^8$ is hydrogen. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is 4-chlorophenyl, and each of $R^6$, $R^7$, and $R^8$ is hydrogen. In certain of the immediately preceding embodiments of compounds of Formula (I), the carbon to which $R^5$ is bonded is of the R configuration. In certain of the immediately preceding embodiments of compounds of Formula (I), the carbon to which $R^5$ is bonded is of the S configuration.

In certain embodiments of compounds of Formula (I), $R^2$ and $R^3$ are different and the compound of Formula (I) is substantially one diastereomer. In certain embodiments of compounds of Formula (I), the stereochemistry at the carbon to which $R^2$ and $R^3$ are bonded is of the S-configuration and the compound of Formula (I) is substantially one diastereomer. In certain embodiments of compounds of Formula (I), the stereochemistry at the carbon to which $R^2$ and $R^3$ are bonded is of the R-configuration, and the compound of Formula (I) is substantially one diastereomer. In certain embodiments of compounds of Formula (I), $R^2$ is $C_{1-4}$ alkyl, $R^3$ is hydrogen, and the compound of Formula (I) is substantially one diastereomer. In certain embodiments of compounds of Formula (I), $R^2$ is $C_{1-4}$ alkyl, $R^3$ is hydrogen, the stereochemistry at the carbon to which $R^2$ and $R^3$ are bonded is of the S-configuration, and the compound of Formula (I) is substantially one diastereomer. In certain embodiments of compounds of Formula (I), $R^2$ is $C_{1-4}$ alkyl, $R^3$ is hydrogen, the stereochemistry at the carbon to which $R^2$ and $R^3$ are bonded is of the R-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is isopropyl, $R^2$ is isopropyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is hydrogen, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is isopropyl, $R^2$ is isopropyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is methyl, $R^5$ is hydroxy, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is isopropyl, $R^2$ is isopropyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is hydrogen, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is isopropyl, $R^2$ is isopropyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is methyl, $R^5$ is fluoro, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is 4-chlorophenyl, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is 4-chlorophenyl, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is hydrogen, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is methyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is 4-chlorophenyl, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^{23}$ is n-propyl, $R^3$ is hydrogen, $R^4$ is hydrogen, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is 4-chlorophenyl, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is hydrogen, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is n-propyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is 4-chlorophenyl, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is hydrogen, $R^5$ is 4-chlorophenyl, each of $R^6$, $R^7$, and $R^9$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is isopropyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is isopropyl, $R^2$ is isopropyl, $R^3$ is hydrogen, $R^4$ is hydrogen, $R^5$ is 4-chlorophenyl, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is hydrogen, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is hydrogen, $R^5$ is 4-chlorophenyl, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is hydrogen, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is isopropyl, $R^2$ is isopropyl, $R^3$ is hydrogen, $R^4$ is methyl, $R^5$ is 4-chlorophenyl, each of $R^6$, $R^7$, and $R^9$ is hydrogen, the stereochemistry at the carbon to which $R^2$ and $R^3$ are bonded is of the S-configuration, the stereochemistry at the carbon to which $R^5$ is bonded is of the R-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the R-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the S-configuration, the stereochemistry at the carbon to which $R^5$ is bonded is of the S-configuration, and the compound of Formula (I) is substantially one diastereomer. In certain embodiments of compounds of Formula (I), $R^1$ is isopropyl, $R^2$ is isopropyl, $R^3$ is hydrogen, $R^4$ is methyl, $R^5$ is 4-chlorophenyl, each of $R^6$, $R^7$, and $R^8$ is hydrogen, the stereochemistry at the carbon to which $R^2$ and $R^3$ are bonded is of the R-configuration, the stereochemistry at the carbon to which $R^5$ is bonded is of the S-configuration, and the compound of Formula (I) is substantially one diastereomer.

In certain embodiments of compounds of Formula (I), $R^1$ is selected from methyl, ethyl, n-propyl, isopropyl, n-butyl, isobutyl, sec-butyl, tert-butyl, phenyl, cyclohexyl, and 3-pyridyl, $R^2$ is selected from hydrogen, methyl, n-propyl, and isopropyl, $R^3$ is hydrogen, $R^4$ is methyl, $R^5$ is selected from hydrogen, hydroxy, fluoro, oxo, and 4-chlorophenyl, and each of $R^6$, $R^7$, and $R^8$ is hydrogen.

In certain embodiments of compounds of Formula (I), $R^1$ is isopropyl, $R^2$ is isopropyl, $R^3$ is hydrogen, $R^4$ is methyl, $R^5$ is selected from hydrogen, hydroxy, fluoro, oxo, and 4-chlorophenyl, and each of $R^6$, $R^7$, and $R^8$ is hydrogen.

In certain embodiments of compounds of Formula (I), the compound is selected from:
(1R)-1-[((3S,4S)-2,5-dioxo-3,4-dibenzoyloxypyrrolidinyl)-oxycarbonyloxy]-2-methylpropyl 2-methylpropanoate;
(1S)-1-[((3R,4R)-2,5-dioxo-3,4-dibenzoyloxypyrrolidinyl)-oxycarbonyloxy]-2-methylpropyl 2-methylpropanoate;
3-{[1-isobutanoyloxyethoxy]carbonylamino}propyl methylphosphinic acid;
3-{[1-cyclohexanoyloxyethoxy]carbonylamino}propyl methylphosphinic acid;
3-{[isobutanoyloxymethoxy]carbonylamino}propyl methylphosphinic acid;
3-{[1-isobutanoyloxyethoxy]carbonylamino}-(2S)-hydroxypropyl methylphosphinic acid;
3-{[1-isobutanoyloxyisobutoxy]carbonylamino}propyl methylphosphinic acid;
3-{[benzoyloxymethoxy]carbonylamino}propyl methylphosphinic acid; and
3-{[1-isobutanoyloxyisobutoxy]carbonylamino}-(2S)-hydroxypropyl methylphosphinic acid;

and pharmaceutically acceptable salts thereof, and pharmaceutically acceptable solvates of any of the foregoing.

Synthesis

The compounds disclosed herein may be obtained via the synthetic method illustrated in Scheme 1. Those of ordinary skill in the art will appreciate that a preferred synthetic route to the disclosed compounds consists of attaching promoieties to 3-aminopropylphosphonous acid, 3-aminopropylphosphinic acid, and analogs thereof. Numerous methods have been described in the art for the synthesis of 3-aminopropylphosphonous acid, 3-aminopropylphosphinic acid, and analogs thereof (e.g., Froestl et al., *J. Med. Chem.* 1995, 38, 3297-3312; Hall et al., U.S. Pat. No. 5,281,747; Hall et al., U.S. Pat. No. 5,461,040; Hall et al., U.S. Pat. No. 5,567,840; Elebring et al., International Publication No. WO 01/42252; Taylor, International Publication No. WO 02/100869; Taylor, International Publication No. WO 02/100870; Amin et al., International Publication No. WO 02/100871, each of which is incorporated herein by reference in its entirety). General synthetic methods useful in the synthesis of the compounds described herein are available in the art (e.g., Green et al., "Protective Groups in Organic Chemistry," (Wiley, 2$^{nd}$ ed. 1991); Harrison et al., "Compendium of Synthetic Organic Methods," Vols. 1-8 (John Wiley and Sons, 1971-1996; Larock "Comprehensive Organic Transformations," VCH Publishers, 1989; and Paquette, "Encyclopedia of Reagents for Organic Synthesis," John Wiley & Sons, 1995).

Accordingly, starting materials useful for preparing compounds and intermediates thereof, and/or practicing methods described herein are commercially available or can be prepared by well-known synthetic methods. Other methods for synthesis of the prodrugs described herein are either described in the art or will be readily apparent to the skilled artisan in view of the references provided herein and may be used to synthesize the compounds described herein. Accordingly, the methods presented in the Schemes of the present disclosure are illustrative rather than comprehensive.

A method for synthesizing compounds of Formula (I), illustrated in Scheme 1, employs the reaction of a 3-aminopropylphosphonous acid, 3-aminopropylphosphinic acid, or analog thereof having Formula (II) with a 1-(acyloxy)-alkyl N-hydroxysuccinimidyl carbonate compound of Formula (III), optionally in the presence of a base, as described in the co-pending application Gallop et al., International Publication No. WO 05/010011, which is incorporated herein by reference in its entirety.

Scheme 1

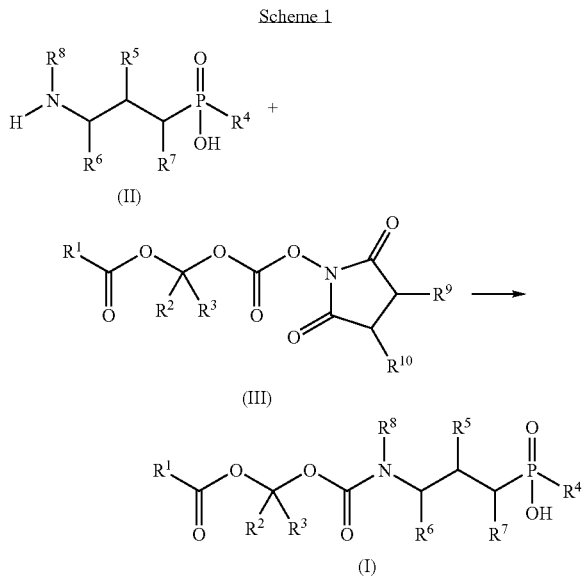

wherein:

$R^9$ and $R^{10}$ are independently selected from hydrogen, acylamino, acyloxy, alkoxycarbonylamino, alkoxycarbonyloxy, alkyl, substituted alkyl, alkoxy, substituted alkoxy, aryl, substituted aryl, arylalkyl, carbamoyloxy, dialkylamino, heteroaryl, hydroxy, and sulfonamido, or $R^9$ and $R^{10}$ together with the atoms to which they are bonded form a substituted cycloalkyl, substituted cycloheteroalkyl, or substituted aryl ring; and $R^1$, $R^2$, $R^3$, $R^4$, $R^5$, $R^6$, $R^7$, and $R^8$ are as defined herein.

In certain embodiments of the method of Scheme 1 for synthesizing a compound of Formula (I), $R^2$ and $R^3$ in the compound of Formula (III) are different, such that the carbon atom to which these substituents are bonded is a stereogenic center.

In certain embodiments of the method described of Scheme 1 for synthesizing a compound of Formula (I), each of $R^9$ and $R^{10}$ in the compound of Formula (III) are benzoyloxy, the stereochemistry at the carbon to which $R^9$ is bonded is of the R-configuration, and the stereochemistry at the carbon to which $R^{10}$ is bonded is of the R-configuration. In certain embodiments of the method described of Scheme 1 for synthesizing a compound of Formula (I), $R^9$ and $R^{10}$ in the compound of Formula (III) are each benzoyloxy, the stereochemistry at the carbon to which $R^9$ is bonded is of the S-configuration and the stereochemistry at the carbon to which $R^{10}$ is bonded is of the S-configuration.

In certain embodiments of the methods f of Scheme 1 or synthesizing a compound of Formula (I), $R^2$ and $R^3$ in the compound of Formula (I) are different and the compound of Formula (I) is substantially one diastereomer. In certain embodiments of the method of Scheme 1 for synthesizing a compound of Formula (I), $R^1$ is isopropyl, $R^2$ is isopropyl, $R^3$ is hydrogen, the stereochemistry at the carbon to which $R^2$ and $R^3$ are bonded is of the S-configuration and the compound of Formula (I) is substantially one diastereomer. In certain embodiments of the method of Scheme 1 for synthesizing a compound of Formula (I), $R^1$ is isopropyl, $R^2$ is isopropyl, $R^3$ is hydrogen, the stereochemistry at the carbon to which $R^2$ and $R^3$ are bonded is of the R-configuration, and the compound of Formula (I) is substantially one diastereomer.

In certain embodiments of the method of Scheme 1 for synthesizing a compound of Formula (I), $R^1$ is $C_{1-6}$ alkyl, $R^2$ is hydrogen or $C_{1-4}$ alkyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ are benzoyloxy, and the stereochemistry at the carbon to which $R^5$ is bonded is of the R-configuration. In certain embodiments of the method of Scheme 1 for synthesizing a compound of Formula (I), $R^1$ is $C_{1-6}$ alkyl, $R^2$ is selected from hydrogen and $C_{1-4}$ alkyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, and the stereochemistry at the carbon to which $R^5$ is bonded is of the S-configuration. In certain embodiments of the method of Scheme 1 for synthesizing a compound of Formula (I), $R^1$ is $C_{1-6}$ alkyl, $R^2$ is methyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, and the stereochemistry at the carbon to which $R^5$ is bonded is of the R-configuration. In certain embodiments of the method of Scheme 1 for synthesizing a compound of Formula (I), $R^1$ is $C_{1-6}$ alkyl, $R^2$ is methyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, and the stereochemistry at the carbon to which $R^5$ is bonded is of the S-configuration. In certain embodiments of the method of Scheme 1 for synthesizing a compound of Formula (I), $R^1$ is $C_{1-6}$ alkyl, $R^2$ is propyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, and the stereochemistry at the carbon to which $R^5$ is bonded is of the R-configuration. In certain embodiments of the method of Scheme 1 for synthesizing a compound of Formula (I), $R^1$ is $C_{1-6}$ alkyl, $R^2$ is propyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ are hydrogen, each of $R^9$ and $R^{10}$ is benzoyloxy, and the stereochemistry at the carbon to which $R^5$ is bonded is of the S-configuration. In certain embodiments of the method of Scheme 1 for synthesizing a compound of Formula (I), $R^1$ is $C_{1-6}$ alkyl, $R^2$ is isopropyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, and the stereochemistry at the carbon to which $R^5$ is bonded is of the R-configuration. In certain embodiments of the method of Scheme 1 for synthesizing a compound of Formula (I), $R^1$ is $C_{1-6}$ alkyl, $R^2$ is isopropyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, and the stereochemistry at the carbon to which $R^5$ is bonded is of the S-configuration.

In certain embodiments of the method of Scheme 1 for synthesizing a compound of Formula (I), $R^1$ is $C_{1-6}$ alkyl, $R^2$ is methyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, the stereochemistry at the carbon to which $R^2$ and $R^3$ are bonded is of the S-configuration, the stereochemistry at the carbon to which $R^a$ is bonded is of the R-configuration, the stereochemistry at the carbon to which $R^9$ is bonded is of the R-configuration, and the stereochemistry at the carbon to which $R^{10}$ is bonded is of the R-configuration.

In certain embodiments of the method of Scheme 1 for synthesizing a compound of Formula (I), $R^1$ is $C_{1-6}$ alkyl, $R^2$ is methyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, the stereochemistry at the carbon to which $R^2$ and $R^3$ are bonded is of the S-configuration, the stereochemistry at the carbon to which $R^5$ is bonded is of the S-configuration, the stereochemistry at the carbon to which $R^9$ is bonded is of the R-configuration, and the stereochemistry at the carbon to which $R^{10}$ is bonded is of the R-configuration.

In certain embodiments of the method of Scheme 1 for synthesizing a compound of Formula (I), $R^1$ is $C_{1-6}$ alkyl, $R^2$ is methyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, the stereochemistry at the carbon to which $R^2$ and $R^3$ are bonded is of the R-configuration, the stereochemistry at the carbon to which $R^5$ is bonded is of the R-configuration, the stereochemistry at the carbon to which $R^9$ is bonded is of the S-configuration and the stereochemistry at the carbon to which $R^{10}$ is bonded is of the S-configuration.

In certain embodiments of the method of Scheme 1 for synthesizing a compound of Formula (I), $R^1$ is $C_{1-6}$ alkyl, $R^2$ is methyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is e benzoyloxy, the stereochemistry at the carbon to which $R^2$ and $R^3$ are bonded is of the R-configuration, the stereochemistry at the carbon to which $R^5$ is bonded is of the S-configuration, the stereochemistry at the carbon to which $R^9$ is bonded is of the S-configuration and the stereochemistry at the carbon to which $R^{10}$ is bonded is of the S-configuration.

In certain embodiments of the method of Scheme 1 for synthesizing a compound of Formula (I), $R^1$ is $C_{1-6}$ alkyl, $R^2$ is propyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, the stereochemistry at the carbon to which $R^2$ and $R^3$ are bonded is of the S-configuration, the stereochemistry at the carbon to which $R^5$ is bonded is of the R-configuration, the stereochemistry at the carbon to which $R^9$ is bonded is of the R-configuration, and the stereochemistry at the carbon to which $R^{10}$ is bonded is of the R-configuration.

In certain embodiments of the method of Scheme 1 for synthesizing a compound of Formula (I), $R^1$ is $C_{1-6}$ alkyl, $R^2$ is propyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, $R^9$ and $R^{10}$ is each benzoyloxy, the stereochemistry at the carbon to which $R^2$ and $R^3$ are bonded is of the S-configuration, the stereochemistry at the carbon to which $R^5$ is bonded is of the S-configuration, the stereochemistry at the carbon to which $R^9$ is bonded is of the R-configuration, and the stereochemistry at the carbon to which $R^{10}$ is bonded is of the R-configuration.

In certain embodiments of the method of Scheme 1 for synthesizing a compound of Formula (I), $R^1$ is $C_{1-6}$ alkyl, $R^2$ is propyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, the stereochemistry at the carbon to which $R^2$ and $R^3$ are bonded is of the R-configuration, the stereochemistry at the carbon to which $R^5$ is bonded is of the R-configuration, the stereochemistry at the carbon to which $R^9$ is bonded is of the S-configuration and the stereochemistry at the carbon to which $R^{10}$ is bonded is of the S-configuration.

In certain embodiments of the method of Scheme 1 for synthesizing a compound of Formula (I), $R^1$ is $C_{1-6}$ alkyl, $R^2$ is propyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, the stereochemistry at the carbon to which $R^2$ and $R^3$ are bonded is of the R-configuration, the stereochemistry at the carbon to which $R^5$ is bonded is of the S-configuration, the stereochemistry at the carbon to which $R^9$ is bonded is of the S-configuration and the stereochemistry at the carbon to which $R^{10}$ is bonded is of the S-configuration.

In certain embodiments of the method of Scheme 1 for synthesizing a compound of Formula (I), $R^1$ is $C_{1-6}$ alkyl, $R^2$ is isopropyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, the stereochemistry at the carbon to which $R^2$ and $R^3$ are bonded is of the S-configuration, the stereochemistry at the carbon to which $R^5$ is bonded is of the R-configuration, the stereochemistry at the carbon to which $R^9$ is bonded is of the R-configuration, and the stereochemistry at the carbon to which $R^{10}$ is bonded is of the R-configuration.

In certain embodiments of the method of Scheme 1 for synthesizing a compound of Formula (I), $R^1$ is $C_{1-6}$ alkyl, $R^2$ is isopropyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, the stereochemistry at the carbon to which $R^2$ and $R^3$ are bonded is of the S-configuration, the stereochemistry at the carbon to which $R^5$ is bonded is of the S-configuration, the stereochemistry at the carbon to which $R^9$ is bonded is of the R-configuration, and the stereochemistry at the carbon to which $R^{10}$ is bonded is of the R-configuration.

In certain embodiments of the method of Scheme 1 for synthesizing a compound of Formula (I), $R^1$ is $C_{1-6}$ alkyl, $R^2$ is isopropyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, the stereochemistry at the carbon to which $R^2$ and $R^3$ are bonded is of the R-configuration, the stereochemistry at the carbon to which $R^5$ is bonded is of the R-configuration, the stereochemistry at the carbon to which $R^9$ is bonded is of the S-configuration and the stereochemistry at the carbon to which $R^{10}$ is bonded is of the S-configuration.

In certain embodiments of the method of Scheme 1 for synthesizing a compound of Formula (I), $R^1$ is $C_{1-6}$ alkyl, $R^2$ is isopropyl, $R^3$ is hydrogen, $R^4$ is selected from hydrogen and methyl, $R^5$ is selected from hydroxy, fluoro, and 4-chlorophenyl, each of $R^6$, $R^7$, and $R^8$ is hydrogen, each of $R^9$ and $R^{10}$ is benzoyloxy, the stereochemistry at the carbon to which $R^2$ and $R^3$ are bonded is of the R-configuration, the stereochemistry at the carbon to which $R^5$ is bonded is of the S-configuration, the stereochemistry at the carbon to which $R^9$ is bonded is of the S-configuration and the stereochemistry at the carbon to which $R^{10}$ is bonded is of the S-configuration.

In certain embodiments, the method of Scheme 1 is carried out in a solvent. Useful solvents include, but are not limited to, acetone, acetonitrile, dichloromethane, dichloroethane, chloroform, toluene, tetrahydrofuran, dioxane, dimethylformamide, dimethylacetamide, N-methylpyrrolidinone, dimethyl sulfoxide, pyridine, ethyl acetate, methyl tert-butyl ether, methanol, ethanol, isopropanol, tert-butanol, water, or combinations thereof. In certain embodiments, the solvent is acetone, acetonitrile, dichloromethane, toluene, tetrahydrofuran, pyridine, methyl tert-butyl ether, methanol, ethanol, isopropanol, water, or combinations thereof. In certain embodiments, the solvent is a mixture of acetonitrile and water. In certain embodiments, the solvent is a mixture of acetonitrile and water, with a volume ratio of acetonitrile to water from about 1:5 to about 5:1. In certain embodiments, the solvent is a mixture of tetrahydrofuran and water, with a volume ratio of tetrahydrofuran to water from about 20:1 to about 2:1. In certain embodiments, the solvent is a mixture of methyl tert-butyl ether and water. In certain embodiments, the solvent is a mixture of methyl tert-butyl ether and water, with a volume ratio of methyl tert-butyl ether to water from about 20:1 to about 2:1. In certain embodiments, the solvent is a mixture of methyl tert-butyl ether and water, wherein the methyl tert-butyl ether contains from about 10% to about 50% acetone by volume. In still other embodiments, the solvent is dichloromethane, water or a combination thereof. In certain embodiments, the solvent is a biphasic mixture of dichloromethane and water. In certain embodiments, the solvent is a biphasic mixture of dichloromethane and water containing from about 0.001 equivalents to about 0.1 equivalents of a phase transfer catalyst. In certain embodiments, the phase transfer catalyst is a tetraalkylammonium salt, and in certain embodiments, the phase transfer catalyst is a tetrabutylammonium salt.

The method of Scheme 1 can be carried out a temperature from about −20° C. to about 40° C. In certain embodiments, the temperature can be from about −20° C. to about 25° C. In other embodiments, the temperature can be from about 0° C. to about 25° C. In certain embodiments, the temperature can be from about 25° C. to about 40° C.

In certain embodiments of the method of Scheme 1, the reaction can be performed in the absence of a base.

In certain embodiments of the method of Scheme 1, the reaction can be performed in the presence of an inorganic base. In certain embodiments, the reaction can be performed in the presence of an alkali metal bicarbonate or alkali metal carbonate salt. In certain embodiments, the reaction can be performed in the presence of sodium bicarbonate.

In certain embodiments of the method of Scheme 1, the reaction can be performed in the presence of an organic base. In certain embodiments, the reaction can be performed in the presence of an organic base such as triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene, 1,5-diazabicyclo[4.3.0]undec-7-ene, or a combination of any of the foregoing, and in certain embodiments, the reaction can be performed in the presence of an organic base such as triethylamine, diisopropylethylamine, N-methylmorpholine, pyridine, or a combination of any of the foregoing.

Pharmaceutical Compositions

Pharmaceutical compositions comprising a therapeutically effective amount of one or more acyloxyalkyl carbamate prodrugs of 3-aminopropylphosphonous acid, 3-aminopropylphosphinic acid, or analogs thereof of Formula (I), such as in purified form, together with a suitable amount of a pharmaceutically acceptable vehicle, so as to provide a form for proper administration to a patient are provided herein. Suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents. In addition, auxiliary, stabilizing, thickening, lubricating, and coloring agents may be used.

Pharmaceutical compositions may be manufactured by means of conventional mixing, dissolving, granulating, dragee-making, levigating, emulsifying, encapsulating, entrapping, or lyophilizing processes. Pharmaceutical compositions may be formulated in conventional manner using one or more physiologically acceptable carriers, diluents, excipients, or auxiliaries, which facilitate processing of compounds disclosed herein into preparations, which can be used pharmaceutically. Proper formulation can depend upon the route of administration chosen.

The present pharmaceutical compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see "Remington's Pharmaceutical Sciences," Lippincott Williams & Wilkins, 21st Edition, 2005). In some embodiments, compositions are formulated for oral delivery, particularly for sustained release oral administration.

Pharmaceutical compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, when in tablet or pill form, a composition may be coated to delay disintegration and absorption in the gastrointestinal tract, thereby providing a sustained action over an extended period of time. Oral compositions can include standard vehicles such as mannitol, lactose, starch, magnesium stearate, sodium saccharine, cellulose, magnesium carbonate, etc. Such vehicles are generally of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines, and the like may be added.

When a compound of Formula (I) is acidic, it may be included in any of the above-described formulations as the free acid, a pharmaceutically acceptable salt, a solvate, or hydrate. Pharmaceutically acceptable salts substantially retain the activity of the free acid, may be prepared by reaction with bases, and tend to be more soluble in aqueous and other protic solvents than the corresponding free acid form. In certain embodiments, sodium salts of a compound of Formula (I) are used in the above described formulations.

Sustained Release Oral Dosage Forms

Compounds of Formula (I) can be used with a number of different dosage forms, which may be adapted to provide sustained release of a compound of Formula (I) upon oral administration.

In some embodiments, a dosage form can comprise beads that on dissolution or diffusion release a compound of the present disclosure over an extended period of hours, in certain embodiments, over a period of at least about 6 hours, in certain embodiments, over a period of at least about 8 hours, and in certain embodiments, over a period of at least about 12 hours. The beads may have a central composition or core comprising a compound of the present disclosure and pharmaceutically acceptable vehicles, including an optional lubricant, antioxidant and buffer. The beads may be medical preparations with a diameter of about 0.05 mm to about 2 mm. Individual beads may comprise doses of a compound of the present disclosure, for example, doses of up to about 40 mg of compound. The beads, in some embodiments, can be formed of non-cross-linked materials to enhance their discharge from the gastrointestinal tract. The beads may be coated with a release rate-controlling polymer that gives a timed release profile.

The time-release beads may be manufactured into a tablet for therapeutically effective administration. The beads can be made into matrix tablets by the direct compression of a plurality of beads coated with, for example, an acrylic resin and blended with excipients such as hydroxypropylmethyl cellulose. The manufacture of beads has been disclosed in the art (Lu, *Int. J. Pharm.* 1994, 112, 117-124; "Remington's Pharmaceutical Sciences," Lippincott Williams & Wilkins, 21st Edition, 2005; Fincher, *J. Pharm. Sci.* 1968, 57, 1825-1835; and U.S. Pat. No. 4,083,949) as has the manufacture of tablets ("Remington's Pharmaceutical Sciences," Lippincott Williams & Wilkins, 21 st Edition, 2005).

One type of sustained release oral dosage formulation that may be used with compounds of the present disclosure can comprise an inert core, such as a sugar sphere, coated with an inner drug-containing layer and an outer membrane layer controlling drug release from the inner layer. A "sealcoat" may be provided between the inert core and the layer containing the active ingredient. When the core is of a water-soluble or water-swellable inert material, the sealcoat is can be in the form of a relatively thick layer of a water-insoluble polymer. Such a controlled release beads may thus comprise: (i) a core unit of a substantially water-soluble or water-swellable inert material; (ii) a first layer on the core unit of a substantially water-insoluble polymer; (iii) a second layer covering the first layer and containing an active ingredient; and (iv) a third layer on the second layer of polymer effective for controlled release of the active ingredient, wherein the first layer is adapted to control water penetration into the core.

In certain embodiments, the first layer (ii) above usually constitutes more than about 2% (w/w) of the final bead composition, such as more than about 3% (w/w), e.g., from about 3% to about 80% (w/w). The amount of the second layer (ii) above usually constitutes from about 0.05% to about 60% (w/w), such as from about 0.1% to about 30% (w/w) of the final bead composition. The amount of the third layer (iv) above usually constitutes from about 1% to about 50% (w/w), such as from about 2% to about 25% (w/w) of the final bead composition. The core unit can have a size ranging from about 0.05 to about 2 mm. The controlled release beads may be provided in a multiple unit formulation, such as a capsule or a tablet.

The cores can comprise a water-soluble or swellable material and may be any such material that is conventionally used as cores or any other pharmaceutically acceptable water-soluble or water-swellable material made into beads or pellets. The cores may be spheres of materials such as sucrose/starch (Sugar Spheres NF), sucrose crystals, or extruded and dried spheres typically comprised of excipients such as microcrystalline cellulose and lactose. The substantially water-insoluble material in the first, or sealcoat layer is generally a "GI insoluble" or "GI partially insoluble" film forming polymer (dispersed or dissolved in a solvent). Examples include, but are not limited to, ethyl cellulose, cellulose acetate, cellulose acetate butyrate, polymethacrylates such as ethyl acrylate/methyl methacrylate copolymer (Eudragit® NE-30-D, Eudragit® S, and Eudragit® L) and ammonio methacrylate copolymer types A and B (Eudragit RL30D, Eudragit® RS30D, Eudragit® RL, and Eudragit® RS), and silicone elastomers. Usually, a plasticizer is used together with the polymer. Examples of plasticizers include, but are not limited to, dibutylsebacate, propylene glycol, triethylcitrate, tributylcitrate, castor oil, acetylated monoglycerides, acetyl triethylcitrate, acetyl butylcitrate, diethyl phthalate, dibutyl phthalate, triacetin, and fractionated coconut oil (medium-chain triglycerides). The second layer containing the active ingredient can comprise the active ingredient with or without a polymer as a binder. When used, the binder can be hydrophilic, and can be water-soluble or water-insoluble. Examples of polymers that may be used in the second layer containing the active drug are hydrophilic polymers such as, for example, polyvinylpyrrolidone (PVP), polyalkylene glycol such as polyethylene glycol, gelatine, polyvinyl alcohol, starch and derivatives thereof, cellulose derivatives such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, and carboxymethylhydroxyethyl cellulose, acrylic acid polymers, polymethacrylates, or any other pharmaceutically acceptable polymer. The ratio of drug to hydrophilic polymer in the second layer can be in the range of from 1:100 to 100:1 (w/w). Suitable polymers for use in the third layer, or membrane, for controlling the drug release may be selected from water-insoluble polymers or polymers with pH-dependent solubility, such as, for example, ethyl cellulose, hydroxypropylmethyl cellulose phthalate, cellulose acetate phthalate, cellulose acetate trimellitate, polymethacrylates, or mixtures thereof, optionally combined with plasticizers, such as those mentioned above. Optionally, the controlled release layer comprises, in addition to the polymers above, other substance(s) with different solubility characteristics, to adjust the permeability and thereby the release rate, of the controlled release layer. Examples of polymers that may be used as a modifier together with, for example, ethyl cellulose include, but are not limited to, HPMC, hydroxyethyl cellulose, hydroxypropyl cellulose, methylcellulose, carboxymethylcellulose, polyethylene glycol, polyvinylpyrrolidone (PVP), polyvinyl alcohol, polymers with pH-dependent solubility, such as cellulose acetate phthalate or ammonio methacrylate copolymer and methacrylic acid copolymer, and mixtures thereof. Additives such as sucrose, lactose and pharmaceutical grade surfactants may also be included in the controlled release layer, if desired.

The preparation of a multiple unit formulation can comprise the additional step of transforming the prepared beads into a pharmaceutical formulation, such as by filling a predetermined amount of the beads into a capsule, or compressing the beads into tablets. Examples of multi-particulate sustained release oral dosage forms are described in, for example, U.S. Pat. Nos. 6,627,223 and 5,229,135.

In certain embodiments, an oral sustained release pump may be used (see Langer, supra; Sefton, *CRC Crit Ref Biomed. Eng.* 1987, 14, 201; Saudek et al., *N. Engl. J Med.* 1989, 321, 574).

In certain embodiments, polymeric materials can be used (See "Medical Applications of Controlled Release," Langer and Wise (eds.), CRC Press., Boca Raton, Fla. (1974); "Controlled Drug Bioavailability," Drug Product Design and Performance, Smolen and Ball (eds.), Wiley, New York (1984); Langer et al., *J Macromol. Sci. Rev. Macromol Chem.* 1983, 23, 61; see also Levy et al., *Science* 1985, 228, 190; During et al., *Ann. Neurol.* 1989, 25, 351; Howard et al., 1989, *J. Neurosurg.* 71:105). In certain embodiments, polymeric materials are used for sustained release oral delivery. Polymers for sustained release oral delivery systems include, but are not limited to, sodium carboxymethylcellulose, hydroxypropylcellulose, hydroxypropylmethylcellulose and hydroxyethylcellulose (especially, hydroxypropylmethylcellulose). Other cellulose ethers have been described (Alderman, *Int. J. Pharm. Tech. & Prod. Mfr.* 1984, 5(3), 1-9). Factors affecting drug release are well known to the skilled artisan and have been described in the art (Bamba et al., *Int. J. Pharm.* 1979, 2, 307).

In certain embodiments, enteric-coated preparations can be used for sustained release oral administration. Examples of coating materials for enteric-coated preparations include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release), and polymers that form firm layers that are destroyed by an increase in pressure (i.e., pressure-controlled release).

In certain embodiments, drug-releasing lipid matrices can be used for sustained release oral administration. An example is when solid microparticles of a compound of the present disclosure are coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379,700. The lipid-coated particles can optionally be compressed to form a tablet. Another controlled release lipid-based matrix material, which is suitable for sustained release oral administration, comprises polyglycolized glycerides as disclosed in Roussin et al., U.S. Pat. No. 6,171,615.

In certain embodiments, waxes can be used for sustained release oral administration. Examples of suitable sustained compound-releasing waxes are disclosed in Cain et al., U.S. Pat. No. 3,402,240 (caranauba wax, candedilla wax, esparto wax and ouricury wax); Shtohryn et al., U.S. Pat. No. 4,820,523 (hydrogenated vegetable oil, bees wax, caranauba wax, paraffin, candelilla, ozokerite and mixtures thereof); and Walters, U.S. Pat. No. 4,421,736 (mixture of paraffin and castor wax).

In certain embodiments, osmotic delivery systems can be used for oral sustained release administration (Verma et al., *Drug Dev. Ind. Pharm.* 2000, 26, 695-708). In some embodiments, OROS® systems made by Alza Corporation, Mountain View, Calif. are used for oral sustained release delivery devices (Theeuwes et al., U.S. Pat. No. 3,845,770; Theeuwes et al., U.S. Pat. No. 3,916,899).

In certain embodiments, a controlled-release system can be placed in proximity of the target of at least one compound disclosed herein (e.g., within the spinal cord), thus requiring only a fraction of the systemic dose (See, e.g., Goodson, in "Medical Applications of Controlled Release," supra, vol. 2, pp. 115-138 (1984)). Other controlled-release systems discussed in Langer, *Science* 1990, 249, 1527-1533, may also be used.

In certain embodiments, the dosage form can comprise at least one compound of the present disclosure coated on a polymer substrate. The polymer can be an erodible or a non-erodible polymer. The coated substrate may be folded onto itself to provide a bilayer polymer drug dosage form. For example, a compound disclosed herein can be coated onto a polymer such as a polypeptide, collagen, gelatin, polyvinyl alcohol, polyorthoester, polyacetyl, or a polyorthocarbonate and the coated polymer folded onto itself to provide a bilaminated dosage form. In operation, the bioerodible dosage form erodes at a controlled rate to dispense a compound disclosed herein over a sustained release period. Examples of biodegradable polymers include biodegradable poly(amides), poly (amino acids), poly(esters), poly(lactic acid), poly(glycolic acid), poly(carbohydrate), poly(orthoester), poly (orthocarbonate), poly(acetyl), poly(anhydrides), biodegradable poly (dihydropyrans), and poly(dioxinones) which are known in the art (Rosoff, *Controlled Release of Drugs* Chap. 2, pp. 53-95 (1989); and in U.S. Pat. Nos. 3,811,444; 3,962,414; 4,066,747, 4,070,347; 4,079,038; and 4,093,709).

In certain embodiments, a dosage form can comprise at least one compound of the present disclosure loaded into a polymer that releases the compound by diffusion through a polymer, or by flux through pores, or by rupture of a polymer matrix. The drug delivery polymeric dosage form can comprise from about 2 mg to about 500 mg of at least one compound of the present disclosure homogenously contained in or on a polymer. A dosage form can comprise at least one exposed surface at the beginning of dose delivery. The non-exposed surface, when present, can be coated with a pharmaceutically acceptable material impermeable to the passage of a compound of the present disclosure. Such dosage forms can be manufactured by procedures known in the art. An example of providing a dosage form comprises blending a pharmaceutically acceptable carrier such as polyethylene glycol, with a known dose of a compound at an elevated temperature, (e.g., 37° C.), and adding it to a silastic medical grade elastomer with a cross-linking agent, for example, octanoate, followed by casting in a mold. The step is repeated for each optional successive layer. The system is allowed to set for about 1 hour, to provide the dosage form. Examples of polymers for manufacturing a dosage form include olefinic polymers, vinyl polymers, addition polymers, condensation polymers, carbohydrate polymers, and silicone polymers such as polyethylene, polypropylene, polyvinyl acetate, polymethylacrylate, polyisobutylmethacrylate, poly alginate, polyamide, and polysilicone. The polymers and procedures for manufacturing them are described in the art (Coleman et al., *Polymers* 1990, 31, 1187-1231; Roerdink et al., *Drug Carrier Systems* 1989, 9, 57-10; Leong et al., *Adv. Drug Delivery Rev.* 1987, 1, 199-233; Roff et al., *Handbook of Common Polymers* 1971, CRC Press; and U.S. Pat. No. 3,992,518).

In certain embodiments, the dosage form can comprise a plurality of pills. Time-release pills can provide a number of individual doses for providing various time doses for achieving a sustained-release prodrug delivery profile over an extended period of time up to about 24 hours. The matrix can comprise a hydrophilic polymer such as, for example, a polysaccharide, agar, agarose, natural gum, alkali alginate including sodium alginate, carrageenan, fucoidan, furcellaran, laminaran, hypnea, gum arabic, gum ghatti, gum karaya, grum tragacanth, locust bean gum, pectin, amylopectin, gelatin, or a hydrophilic colloid. The hydrophilic matrix can comprise a plurality of about 4 to about 50 pills, each pill comprises a dose population of about 10 ng, about 0.5 mg, about 1 mg, about 1.2 mg, about 1.4 mg, about 1.6 mg, about 5.0 mg, etc. The pills can comprise a release rate-controlling wall of from about 0.001 mm up to about 10 mm thickness to provide for the timed release of a compound. Examples of wall forming materials include triglyceryl esters such as glyceryl tristearate, glyceryl monostearate, glyceryl dipalmitate, glyceryl laureate, glyceryl didecenoate, and glyceryl tridenoate. Other wall forming materials comprise polyvinyl acetate, phthalate, methylcellulose phthalate, and microporous olefins. Procedures for manufacturing pills are disclosed in U.S. Pat. Nos. 4,434,153; 4,721,613; 4,853,229; 2,996,431; 3,139,383 and 4,752,470.

In certain embodiments, a dosage form comprises an osmotic dosage form, which comprises a semipermeable wall that surrounds a therapeutic composition comprising a compound of the present disclosure. In use within a patient, the osmotic dosage form comprising a homogenous composition, imbibes fluid through the semipermeable wall into the dosage form in response to the concentration gradient across the semipermeable wall. The therapeutic composition in the dosage form develops osmotic pressure differential that causes the therapeutic composition to be administered through an exit from the dosage form over a prolonged period of time up to about 24 hours (or even in some cases up to about 30 hours) to provide controlled and sustained compound release. These delivery platforms can provide an essentially zero order delivery profile as opposed to the spiked profiles of immediate release formulations.

In certain embodiments, a dosage form can comprise another osmotic dosage form comprising a wall surrounding a compartment, the wall comprising a semipermeable polymeric composition permeable to the passage of fluid and substantially impermeable to the passage of compound present in the compartment, a compound-containing layer composition in the compartment, a hydrogel push layer composition in the compartment comprising an osmotic formulation for imbibing and absorbing fluid for expanding in size for pushing the compound composition layer from the dosage form, and at least one passageway in the wall for releasing the prodrug composition. The dosage form can deliver a compound by imbibing fluid through the semipermeable wall at a fluid imbibing rate determined by the permeability of the semipermeable wall and the osmotic pressure across the semipermeable wall causing the push layer to expand, thereby delivering the compound from the dosage form through the exit passageway to a patient over a prolonged period of time (up to about 24 or even about 30 hours). The hydrogel layer composition may comprise from about 10 mg to about 1000 mg of a hydrogel such as a polyalkylene oxide of about 1,000,000 to about 8,000,000 weight-average molecular weight, for example, a polyethylene oxide of about 1,000,000 weight-average molecular weight, a polyethylene oxide of about 2,000,000 molecular weight, a polyethylene oxide of about 4,000,000 molecular weight, a polyethylene oxide of about 5,000,000 molecular weight, a polyethylene oxide of about 7,000,000 molecular weight, and a polypropylene oxide of the about 1,000,000 to about 8,000,000 weight-average molecular weight; or about 10 mg to about 1000 mg of an alkali carboxymethylcellulose of about 10,000 to about 6,000,000 weight average molecular weight, such as sodium carboxymethylcellulose or potassium carboxymethylcellulose. The hydrogel expansion layer comprises from about 0.0 mg to about 350 mg, in present manufacture; from about 0.1 mg to about 250 mg of a hydroxyalkylcellulose of about 7,500 to about 4,500,00 weight-average molecular weight (e.g., hydroxymethylcellulose, hydroxyethylcellulose, hydroxypropylcellulose, hydroxybutylcellulose, or hydroxypentylcellulose) in present manufacture; from about 1 mg to about 50 mg of an agent such as sodium chloride, potassium chloride, potassium acid phosphate, tartaric acid, citric acid, raffinose, magnesium sulfate, magnesium chloride, urea, inositol, sucrose, glucose, or sorbitol; from about 0 to about 5 mg of a colorant, such as ferric oxide; from about 0 mg to about 30 mg, in a present manufacture, from about 0.1 mg to about 30 mg of a hydroxypropylalkylcellulose of about 9,000 to about 225,000 average-number molecular weight, such as, for example, hydroxypropylethylcellulose, hydroxypropypentylcellulose, hydroxypropylmethylcellulose, and hydropropylbutylcellulose; from about 0.00 to about 1.5 mg of an antioxidant such as ascorbic acid, butylated hydroxyanisole, butylated hydroxyquinone, butylhydroxyanisol, hydroxycoumarin, butylated hydroxytoluene, cephalm, ethyl gallate, propyl gallate, octyl gallate, lauryl gallate, propylhydroxybenzoate, trihydroxybutylrophenone, dimethylphenol, dibutylphenol, vitamin E, lecithin, or ethanolamine; and from about 0.0 mg to about 7 mg of a lubricant such as calcium stearate, magnesium stearate, zinc stearate, magnesium oleate, calcium palmitate, sodium suberate, potassium laurate, salts of fatty acids, salts of alicyclic acids, salts of aromatic acids, stearic acid, oleic acid, palmitic acid, a mixture of a salt of a fatty, alicyclic or aromatic acid, and a fatty, alicyclic, or aromatic acid.

In the osmotic dosage forms, the semipermeable wall can comprise a composition that is permeable to the passage of fluid and impermeable to the passage of prodrug. The wall is nontoxic and comprises a polymer such as cellulose acylate, cellulose diacylate, cellulose triacylate, cellulose acetate, cellulose diacetate, or cellulose triacetate. The wall can comprise from about 75 wt % (weight percent) to about 100 wt % of the cellulosic wall-forming polymer or, the wall can comprise additionally from about 0.01 wt % to about 80 wt % of polyethylene glycol, or from about 1 wt % to about 25 wt % of a cellulose such as hydroxypropylcellulose or a hydroxypropylalkycellulose such as hydroxypropylmethylcellulose. The total weight percent of all components comprising the wall is equal to 100 wt %. The internal compartment can comprise the compound-containing composition alone or in layered position with an expandable hydrogel composition. The expandable hydrogel composition in the compartment can increase in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of prodrug to a patient over time. The dosage form can comprise a passageway in the wall that connects the exterior of the dosage form with the internal compartment. The osmotic powered dosage form can be made to deliver prodrug from the dosage form to the patient at a zero order rate of release over a period of up to about 24 hours.

The expression "passageway" as used herein can comprise means and methods suitable for the metered release of the compound from the compartment of the dosage form. The exit means can comprise at least one passageway, including orifice, bore, aperture, pore, porous element, hollow fiber, capillary tube, channel, porous overlay, or porous element that provides for the osmotic controlled release of compound. The passageway can include a material that erodes or is leached from the wall in a fluid environment of use to produce at least one controlled-release dimensioned passageway. Examples of materials suitable for forming a passageway, or a multiplicity of passageways include a leachable poly(glycolic) acid or poly(lactic) acid polymer in the wall, a gelatinous filament, poly(vinyl alcohol), leach-able polysaccharides, salts, and oxides. A pore passageway, or more than one pore passageway, can be formed by leaching a leachable compound, such as sorbitol, from the wall. The passageway can have controlled-release dimensions, such as round, triangular, square and elliptical, for the metered release of prodrug from the dosage form. The dosage form can be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in U.S. Pat. Nos. 3,845,770; 3,916,899; 4,063,064; 4,088,864; and 4,816,263. Passageways formed by leaching are disclosed in U.S. Pat. Nos. 4,200,098 and 4,285,987.

Regardless of the specific form of sustained release oral dosage form used, in certain embodiments, compounds can be released from the dosage form over a period of at least about 4 hours, at least about 8 hours, at least about 12 hours, at least about 16 hours, at least about 20 hours, and in certain embodiments, at least about 24 hours. In certain embodiments, a dosage form can release from about 0% to about 30% of the prodrug in 0 to about 2 hours, from about 20% to about 50% of the prodrug in about 2 to about 12 hours, from about 50% to about 85% of the prodrug in about 3 to about 20 hours and greater than about 75% of the prodrug in about 5 to about 18 hours. A sustained release oral dosage form of the present disclosure can further provide a concentration of the corresponding 3-aminopropylphosphonous acid, 3-aminopropylphosphinic acid, or analog thereof in the plasma and/or blood of a patient over time, which curve has an area under the curve (AUC) that is proportional to the dose of the prodrug of the corresponding 3-aminopropylphosphonous acid, 3-aminopropylphosphinic acid, or analog thereof administered, and a maximum concentration $C_{max}$. The $C_{max}$ is less than about 75%, for example less than about 60%, of the $C_{max}$ obtained from administering an equivalent dose of the compound from an immediate release oral dosage form and the AUC is substantially the same as the AUC obtained from administering an equivalent dose of the prodrug from an immediate release oral dosage form.

In certain embodiments, dosage forms can be administered once or twice per day, and in certain embodiments, once per day.

Therapeutic Uses of Compounds, Compositions and Dosage Forms

In certain embodiments, a therapeutically effective amount of one or more compounds of Formula (I) can be administered to a patient, such as a human, suffering from stiffness, involuntary movements and/or pain associated with spasticity. The underlying etiology of the spasticity being so treated may have a multiplicity of origins, including, e.g., cerebral palsy, multiple sclerosis, stroke and head and spinal cord injuries. In certain embodiments, a therapeutically effective amount of one or more compounds of Formula (I) can be administered to a patient, such as a human, suffering from gastroesophageal reflux disease. In certain embodiments, a therapeutically effective amount of one or more compounds of Formula (I) can be administered to a patient, such as a human, suffering from emesis. In still other embodiments, a therapeutically effective amount of one or more compounds of Formula (I) can be administered to a patient, such as, a human, suffering from cough. In certain embodiments, a therapeutically effective amount of one or more compounds of Formula (I) can be administered to a patient, such as a human, suffering from drug addiction. Addiction to stimulants such as cocaine or amphetamines, or narcotics such as morphine or heroin may be effectively treated by administration of one or more compounds of Formula (I). In certain embodiments, a therapeutically effective amount of one or more compounds of Formula (I) can be administered to a patient, such as a human, suffering from alcohol abuse or addiction, or nicotine abuse or addiction. In certain of these embodiments, sustained release oral dosage forms comprising a therapeutically effective amount of one or more compounds of Formula (I) can be administered to the patients.

Further, in certain embodiments, a therapeutically effective amount of one or more compounds of Formula (I) can be administered to a patient, such as a human, as a preventative measure against various diseases or disorders. Thus, a therapeutically effective amount of one or more compounds of Formula (I) can be administered as a preventative measure to a patient having a predisposition for spasticity, gastroesophageal reflux disease, emesis, cough, alcohol addiction or abuse, nicotine addiction or abuse, or other drug addiction or abuse.

When used to treat or prevent the above diseases or disorders a therapeutically effective amount of one or more compounds of Formula (I) can be administered or applied singly, or in combination with other agents including pharmaceutically acceptable vehicles and/or pharmaceutically active agents for treating a disease or disorder, which may be the same or different disease or disorder as the disease or disorder being treated by the one or more compounds of Formula (I). A therapeutically effective amount of one or more compounds of Formula (I) can be delivered together with a compound disclosed herein or combination with another pharmaceutically active agent. For example, in the treatment of a patient suffering from gastroesophageal reflux disease, a dosage form comprising a compound of Formula (I) may be administered in conjunction with a proton pump inhibitor, such as omeprazole, esomeprazole, pantoprazole, lansoprazole, or rabeprazole sodium, or with an $H_2$ antagonist such as rantidine, cimetidine, or famotidine.

Dosage forms, upon releasing a prodrug of 3-aminopropylphosphonous acid, 3-aminopropylphosphinic acid, or analog thereof, can provide the corresponding 3-aminopropylphosphonous acid, 3-aminopropylphosphinic acid, or analog thereof analogs upon in vivo administration to a patient. The promoiety or promoieties of the prodrug may be cleaved either chemically and/or enzymatically. One or more enzymes present in the stomach, intestinal lumen, intestinal tissue, blood, liver, brain or any other suitable tissue of a mammal may enzymatically cleave the promoiety or promoieties of the prodrug. If the promoiety or promoieties are cleaved after absorption by the gastrointestinal tract, the prodrugs of 3-aminopropylphosphonous acid, 3-aminopropylphosphinic acid, or analog thereof may have the opportunity to be absorbed into the systemic circulation from the large intestine. In certain embodiments, the promoiety or promoieties are cleaved after absorption by the gastrointestinal tract.

Prodrugs of 3-aminopropylphosphonous acid, 3-aminopropylphosphinic acid, or analogs thereof having Formula (I) or pharmaceutically acceptable salts, or solvates of any of the foregoing as disclosed herein, and/or pharmaceutical compositions thereof can provide therapeutic or prophylactic levels of the corresponding 3-aminopropylphosphonous acid, 3-aminopropylphosphinic acid, or analog thereof upon in vivo administration to a patient. The prodrug promoiety of the compounds of Formula (I) can be cleaved either chemically and/or enzymatically. One or more enzymes present in the stomach, intestinal lumen, intestinal tissue, blood, liver, brain, or any other suitable tissue of a mammal may enzymatically cleave the promoiety of the administered compounds.

The promoiety of a prodrug of 3-aminopropylphosphonous acid, 3-aminopropylphosphinic acid, or analogs thereof having Formula (I) may be cleaved prior to absorption by the gastrointestinal tract (e.g., within the stomach or intestinal lumen) and/or after absorption by the gastrointestinal tract (e.g., in intestinal tissue, blood, liver, or other suitable tissue of a mammal). In certain embodiments, 3-aminopropylphosphonous acid, 3-aminopropylphosphinic acid, or analog thereof remains conjugated to the prodrug promoiety during transit across the intestinal mucosal barrier to provide protection from presystemic metabolism. In certain embodiments, a prodrug of 3-aminopropylphosphonous acid, 3-aminopropylphosphinic acid, or analog thereof having Formula (I) is essentially not metabolized to the corresponding 3-aminopropylphosphonous acid, 3-aminopropylphosphinic acid, or analog thereof within enterocytes but is metabolized to the parent drug within the systemic circulation. Cleavage of the promoiety of the prodrug of 3-aminopropylphosphonous acid, 3-aminopropylphosphinic acid, or analog thereof having of Formula (I) after absorption by the gastrointestinal tract may allow these prodrugs to be absorbed into the systemic circulation either by active transport, passive diffusion, or by a mixture of both active and passive processes. Accordingly, in certain embodiments, a pharmaceutical composition or dosage form of the present disclosure is capable of maintaining a therapeutically effective concentration of prodrugs of 3-aminopropylphosphonous acid, 3-aminopropylphosphinic acid, or analogs thereof in the plasma of a patient for a time period of at least about 4 hours, at least about 8 hours, at least about 12 hours, at least about 16 hours, at least about 20 hours, and in certain embodiments for a period of at least about 24 hours, after the pharmaceutical composition or dosage form comprising a corresponding prodrug of 3-aminopropylphosphonous acid, 3-aminopropylphosphinic acid, or analog thereof having Formula (I) is orally administered to the patient.

In certain embodiments, a prodrug of 3-aminopropylphosphonous acid, 3-aminopropylphosphinic acid, or analog thereof having Formula (I) is selected from a prodrug of:
3-aminopropylphosphonous acid;
(3-amino-2-(4-chlorophenyl)propyl)phosphonous acid;
(3-amino-2-hydroxypropyl)phosphonous acid;
(2S)-(3-amino-2-hydroxypropyl)phosphonous acid;
(2R)-(3-amino-2-hydroxypropyl)phosphonous acid;
(3-amino-2-fluoropropyl)phosphonous acid;
(2S)-(3-amino-2-fluoropropyl)phosphonous acid;
(2R)-(3-amino-2-fluoropropyl)phosphonous acid;
(3-amino-2-oxopropyl)phosphonous acid;
(3-amino-(2S)-(4-chlorophenyl)propyl)phosphonous acid;
(3-amino-(2R)-(4-chlorophenyl)propyl)phosphonous acid;
3-aminopropylmethylphosphinic acid;
(3-amino-2-(4-chlorophenyl)propyl)methylphosphinic acid;
(3-amino-2-hydroxypropyl)methylphosphinic acid;
(2S)-(3-amino-2-hydroxypropyl)methylphosphinic acid;
(2R)-(3-amino-2-hydroxypropyl)methylphosphinic acid;
(3-amino-2-fluoropropyl)methylphosphinic acid;
(2S)-(3-amino-2-fluoropropyl)methylphosphinic acid;
(2R)-(3-amino-2-fluoropropyl)methylphosphinic acid;
(3-amino-2-oxopropyl)methylphosphinic acid;
(3-amino-(2S)-(4-chlorophenyl)propyl)methylphosphinic acid; and
(3-amino-(2R)-(4-chlorophenyl)propyl)methylphosphinic acid;
and pharmaceutically acceptable salts thereof, and pharmaceutically acceptable solvates of any of the foregoing.

Prodrugs of 3-aminopropylphosphonous acid, 3-aminopropylphosphinic acid, or analogs thereof having Formula (I) or pharmaceutically acceptable salts thereof, or pharmaceutically acceptable solvates of any of the foregoing as disclosed herein, and/or pharmaceutical compositions thereof can be administered orally. Prodrugs of 3-aminopropylphosphonous acid, 3-aminopropylphosphinic acid, or analogs thereof having Formula (I) and/or pharmaceutical compositions thereof can also be administered by any other convenient route, for example, by infusion or bolus injection, by absorption through epithelial or mucocutaneous linings (e.g., oral mucosa, rectal, and intestinal mucosa, etc.). Administration can be systemic or local. Various delivery systems are known, (e.g., encapsulation in liposomes, microparticles, microcapsules, capsules, etc.) that can be used to administer a compound and/or pharmaceutical composition. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, inhalation, or topically, particularly to the ears, nose, eyes, or skin.

In certain embodiments, it may be desirable to introduce prodrugs of 3-aminopropylphosphonous acid, 3-aminopropylphosphinic acid, or analogs thereof having Formula (I) and/or pharmaceutical compositions thereof into the central nervous system by any suitable route, including intraventricular, intrathecal, and epidural injection. Intraventricular injection can be facilitated using an intraventricular catheter attached to a reservoir such as an Ommaya reservoir.

In some embodiments, prodrugs of 3-aminopropylphosphonous acid, 3-aminopropylphosphinic acid, or analogs thereof having Formula (I) and/or pharmaceutical compositions thereof can be delivered via sustained release systems, such as oral sustained release systems. In certain embodiments, a pump may be used (Langer, supra; Sefton, *CRC Crit Ref Biomed Eng.* 1987, 14, 201; Saudek et al., *N. Engl. J Med.* 1989, 321, 574).

Doses

Prodrugs of 3-aminopropylphosphonous acid, 3-aminopropylphosphinic acid, or analogs thereof having Formula (I) can be administered to treat or prevent diseases or disorders such as spasticity, gastroesophageal reflux disease, emesis, cough, alcohol addiction or abuse, nicotine addiction or abuse, or other drug addiction or abuse.

The amount of a prodrug of 3-aminopropylphosphonous acid, 3-aminopropylphosphinic acid, or analog thereof that will be effective in the treatment of a particular disease or disorder disclosed herein will depend on the nature of the disease or disorder, and can be determined by standard clinical techniques known in the art. In addition, in vitro or in vivo assays may optionally be employed to help identify optimal dosage ranges. The amount of a compound administered will, of course, depend on, among other factors, the subject being treated, the weight of the subject, the severity of the disease or disorder, the manner of administration and the judgment of the prescribing physician.

In certain embodiments, dosage forms can be adapted to be administered to a patient no more than twice per day, and in certain embodiments, only once per day. Dosing may be provided alone or in combination with other drugs and may continue as long as required for effective treatment of the disease state or disorder.

Suitable dosage ranges for oral administration can depend on the potency of the parent 3-aminopropylphosphonous acid, 3-aminopropylphosphinic acid, or analog thereof. For 3-aminopropylphosphonous acid, 3-aminopropylphosphinic acid, or analogs thereof, doses can range from about 0.1 mg to about 20 mg per kilogram body weight. Certain 3-aminopropylphosphonous acid analogs or 3-aminopropylphosphinic acid analogs may be more potent and lower doses may be appropriate for both the parent drug and any prodrug (measured on an equivalent molar basis). Dosage ranges may be readily determined by methods known to the skilled artisan.

Combination Therapy

In certain embodiments, prodrugs of 3-aminopropylphosphonous acid, 3-aminopropylphosphinic acid, or analogs thereof having Formula (I) or pharmaceutically acceptable salts thereof, or solvates of any of the foregoing can be used in combination therapy with at least one other therapeutic agent. Prodrugs of 3-aminopropylphosphonous acid, 3-aminopropylphosphinic acid, or analogs thereof having Formula (I) and the at least one other therapeutic agent(s) can act additively or, in certain embodiments, synergistically. In certain embodiments, a prodrug of 3-aminopropylphosphonous acid, 3-aminopropylphosphinic acid, or analog thereof having Formula (I) can be administered concurrently with the administration of another therapeutic agent. In certain embodiments, a prodrug of 3-aminopropylphosphonous acid, 3-aminopropylphosphinic acid, or analog thereof having Formula (I) or pharmaceutically acceptable salt thereof, or solvate of any of the foregoing can be administered prior or subsequent to administration of another therapeutic agent. The at least one other therapeutic agent can be effective for treating the same or different disease or disorder.

Methods of the present disclosure include administration of one or more compounds or pharmaceutical compositions of the present disclosure and one or more other therapeutic agents provided that the combined administration does not inhibit the therapeutic efficacy of the one or more compounds of the present disclosure and/or does not produce adverse combination effects.

In certain embodiments, compositions of the present disclosure can be administered concurrently with the administration of another therapeutic agent, which can be part of the same pharmaceutical composition as, or in a different composition from, that containing the compounds of the present disclosure. In certain embodiments, compounds of the present disclosure can be administered prior or subsequent to administration of another therapeutic agent. In certain embodiments of combination therapy, the combination therapy comprises alternating between administering a composition of the present disclosure and a composition comprising another therapeutic agent, e.g., to minimize adverse side effects associated with a particular drug. When a compound of the present disclosure is administered concurrently with another therapeutic agent that potentially can produce adverse side effects including, but not limited to, toxicity, the therapeutic agent can advantageously be administered at a dose that falls below the threshold at which the adverse side effect is elicited.

In certain embodiments, a pharmaceutical composition can further comprise substances to enhance, modulate and/or control release, bioavailability, therapeutic efficacy, therapeutic potency, stability, and the like. For example, to enhance therapeutic efficacy a compound of the present disclosure can be co-administered with one or more active agents to increase the absorption or diffusion of the compound from the gastrointestinal tract, or to inhibit degradation of the drug in the systemic circulation. In certain embodiments, a compound of the present disclosure can be co-administered with active agents having a pharmacological effect that enhance the therapeutic efficacy of the drug.

In certain embodiments, compounds or pharmaceutical compositions of the present disclosure include, or can be administered to a patient together with, another compound for treating or preventing spasticity, drugs for treating or preventing gastroesophageal reflux disease, drugs for treating or preventing narcotic addiction or abuse, drugs for treating or preventing alcohol addiction or abuse, drugs for treating or preventing nicotine addiction or abuse, or drugs for treating or preventing emesis or cough.

Examples of drugs for treating or preventing movement disorders such as spasticity include levodopa, mild sedatives such as benzodiazepines including alprazolam, chlordiazepoxide, clonazepam, clorazepate, diazepam, lorazepam, and oxazepam; muscle relaxants such as baclofen, anticholinergic drugs such as trihexyphenidyl and diphenhydramine; antipsychotics such as chlorpromazine, fluphenazine, haloperidol, loxapine, mesoridazine, molindone, perphenazine, pimozide, thioridazine, thiothixene, trifluoperazine, aripiprazole, clozapine, olanzapine, quetiapine, risperidone, and ziprasidone; and antidepressants such as amitriptyline.

Examples of drugs for treating or preventing gastrointestinal disorders such as gastroesophageal reflux disease include H2 inhibitors such as cimetidine, famotidine, nizatidine, and ranitidine; proton pump inhibitors such as omeprazole, lansoprazole, pantoprazole, rabeprazole, and esomeprazole; and prokinetics such as cisparide, bethanechol, and metoclopramide.

Examples of drugs for treating or preventing emesis (nausea and vomiting) include benzamines such as metoclopramide; phenothiazines such as prochlorperazine, perphenazine, chlorpromazine, promethazine, and thiethylperazine; butyrophenones such as droperidol and haloperidol; dopamine 2 antagonists such as metoclorpamide; 5-HT3 antagonists such as ondansetron, granisetron, dolasetron, palonosetron; NK-1 receptor antagonists such as aprepitant, corticosteroids such as dexamethazone; antihistamines such as diphenhydramine and hydroxyzine; cannabinoids such as dronabinol; and benzodiazepines such as lorazepam, midazolam, alprazolam, and olanzapine Examples of drugs for treating or preventing alcohol addiction or abuse include disulfiram, naltrexone, acamprosate, clonidine, methadone, 1-alpha-acetylmethadol, buprenorphine, bupropion, and baclofen.

Examples of drugs for treating or preventing narcotic addiction or abuse include buprenorphine, tramadol, methadone, and naltrexone.

Examples of drugs for treating or preventing nicotine addiction or abuse include bupropion, clonidine, and nicotine.

Examples of drugs for treating or preventing cough include codeine, dextromethorphan, guaifenesin, hydrocodone, hydromorphone, benzonatate, diphenhydramine, pseudoephedrine, acetaminophen, and carbinoxamine.

EXAMPLES

The following examples describe in detail preparation of compounds and compositions of the present disclosure and protocols for using compounds and compositions of the present disclosure. It will be apparent to those of ordinary skill in the art that many modifications, both to materials and methods, may be practiced without departing from the scope of the disclosure.

In the examples below, the following abbreviations have the following meanings. If an abbreviation is not defined, it has its generally accepted meaning.

| | |
|---|---|
| DMF= | N,N-dimethylformamide |
| g = | gram |
| h = | hour |
| HPLC = | high pressure liquid chromatography |
| L = | liter |
| LC/MS = | liquid chromatography/mass spectroscopy |
| M = | molar |
| mg = | milligram |
| min = | minute |
| mL = | milliliter |

-continued

| | |
|---|---|
| mm = | millimeter |
| mmol = | millimoles |
| mol = | moles |
| THF = | tetrahydrofuran |
| µg = | microgram |
| µL = | microliter |
| µM = | micromolar |
| v/v = | volume to total volume |
| w/v = | weight to total volume |
| w/w = | weight to total weight |

In the examples below, Examples 2-8, 10-12, 14-102, 104, 105, 108-122, 124-182 and 190 are prophetic.

Example 1

O-(1-Isobutanoyloxyethyl) S-Methyl Thiocarbonate (2)

Step A: O-(1-Chloroethyl) S-Methyl Thiocarbonate (3)

A 21% (w/w) aqueous solution of sodium methylthiolate (580.7 g, 1.74 mol) was added to a solution of 1-chloroethyl chloroformate (250 g, 1.74 mol) and tetrabutylammonium hydrogensulfate (5.9 g, 17 mmol) in $CH_2Cl_2$ (450 mL) over 2 h. The reaction mixture was stirred for an additional hour, then worked-up by separating the aqueous phase and extracting the organic phase with brine (2×250 mL). The organic phase was dried over anhydrous sodium sulfate and concentrated in vacuo. The residue was purified by vacuum distillation to afford the title compound (3) as a colorless liquid (277.3 g, 97% yield). $^1$H NMR (CDCl$_3$, 400 MHz): δ 1.82 (d, J=5.6 Hz, 3H), 2.38 (s, 3H), 6.57 (q, J=5.2 Hz, 1H).

Step B: O-(1-Isobutanoyloxyethyl) S-Methyl Thiocarbonate (2)

Compound (3) (308 g, 2 mol) was dissolved in isobutyric acid (264 g, 3 mol). This mixture was slowly added to a pre-mixed solution of isobutyric acid (264 g, 3 mol) and diisopropylethylamine (387 g, 3 mol), and the reaction mixture heated to 55° C. for 16 h, diluted with ether (10 L), washed with water (4×5 L), saturated bicarbonate solution (2×5 L) and brine (5 L), then dried over anhydrous sodium sulfate, filtered, and concentrated in vacuo to give the title compound (2) as colorless liquid (400 g, 97% yield). The product was optionally further purified by vacuum distillation (135° C./20 Torr). $^1$H NMR (CDCl$_3$, 400 MHz): δ 1.17 (d, J=6.8 Hz, 6H), 1.49 (d, J=5.6 Hz, 3H), 2.33 (s, 3H), 2.54 (m, 1H), 6.91 (q, J=5.2 Hz, 1H).

Example 2

O-(1-Butanoyloxyethyl) S-Methyl Thiocarbonate (4)

Following the procedures of Example 1 and replacing isobutyric acid with n-butyric acid in Step B affords the title compound (4) as an oil.

Example 3

O-(1-Pivaloyloxyethyl) S-Methyl Thiocarbonate (5)

Following the procedures of Example 1 and replacing isobutyric acid with pivalic acid in Step B affords the title compound (5) as an oil.

Example 4

O-(1-Cyclohexanoyloxyethyl) S-Methyl Thiocarbonate (6)

Following the procedures of Example 1 and replacing isobutyric acid with cyclohexanecarboxylic acid in Step B afforded the title compound (6) as an oil.

Example 5

O-(Isobutanoyloxymethyl) S-Methyl Thiocarbonate (7)

Following the procedures of Example 1 and replacing 1-chloroethyl chloroformate with chloromethyl chloroformate in Step A afforded the title compound (7) as an oil.

Example 6

O-(Butanoyloxymethyl) S-Methyl Thiocarbonate (8)

Following the procedures of Example 2 and replacing 1-chloroethyl chloroformate with chloromethyl chloroformate in Step A affords the title compound (8) as an oil.

Example 7

O-(Pivaloyloxymethyl) S-Methyl Thiocarbonate (9)

Following the procedures of Example 3 and replacing 1-chloroethyl chloroformate with chloromethyl chloroformate in Step A affords the title compound (9) as an oil.

Example 8

O-(Cyclohexanoyloxymethyl) S-Methyl Thiocarbonate (10)

Following the procedures of Example 4 and replacing 1-chloroethyl chloroformate with chloromethyl chloroformate in Step A affords the title compound (10) as an oil.

Example 9

Synthesis of O-(1-Isobutanoyloxyisobutoxy) S-Methyl Thiocarbonate (11)

Step A: O-(1-Chloroisobutoxy) S-Methyl Thiocarbonate (12)

A solution of 1-chloro-2-methylpropyl chloroformate (1026 g, 6.0 mol) and tetrabutylammonium hydrogensulfate (20 g, 60 mmol) in dichloromethane (1500 mL) in a jacketed 10 L reactor equipped with a mechanical stirrer, temperature probe, and addition funnel was cooled to 10° C. To the reaction mixture was gradually added a 15% aqueous solution of sodium methylthiolate (3 L, 6.4 mol) over 4 h. The reaction was moderately exothermic and the internal temperature was maintained between 10° C. and 20° C. during the addition. The aqueous phase was separated and the organic phase was washed with brine (2×2 L) and water (2 L). The organic layer was dried over anhydrous $Na_2SO_4$, filtered, and concentrated under reduced pressure to afford the title compound (12) (1050 g, 5.76 mol, 96% yield) as a colorless liquid. $^1$H NMR (CDCl$_3$, 400 MHz): δ 1.1 (dd, 6H), 2.2 (m, 1H), 2.4 (s, 3H), 6.35 (d, 1H).

Step B: Tetramethylammonium Isobutyrate (13)

To a 20 L round bottom flask was added isobutyric acid (1300 mL, 14 mol), and an aqueous solution of 25% tetramethylammonium hydroxide (5 L, 14 mol). The water was removed under reduced pressure, and azeotroped with toluene (2×2 L) to leave the title compound (13) as an amber liquid, which was used without further purification.

Step C: O-(1-Isobutanoyloxyisobutoxy) S-Methyl Thiocarbonate (11)

To a 3 L three neck round bottom flask equipped with a mechanical stirrer and Teflon-coated thermocouple was added (13) (1672 g, 9 mol), isobutyric acid (264 g, 1.5 mol), and (12) (1050 g, 5.76 mol). The reaction mixture was heated to 80° C. for 12 h, monitoring the reaction progress by $^1$H NMR. The reaction mixture was cooled to 20° C., diluted with EtOAc (1 L) and washed with water (2×1 L), saturated NaHCO$_3$ (1×2 L) and water (1 L). The organic phase was separated and concentrated under reduced pressure to afford the title compound (11) (905 g, 3.9 mol, 65% yield) as a colorless liquid. $^1$H NMR (CDCl$_3$, 400 MHz): δ 1.0 (d, 6H), 1.2 (dd, 6H), 2.05 (m, 1H), 2.35 (s, 3H), 2.6 (m, 1H), 6.7 (d, 1H).

Example 10

O-(1-Butanoyloxyisobutoxy) S-Methyl Thiocarbonate (14)

Following the procedures of Example 9 and replacing isobutyric acid with n-butyric acid affords the title compound (14) as an oil.

Example 11

O-(1-Pivaloyloxyisobutoxy) S-Methyl Thiocarbonate (15)

Following the procedures of Example 9 and replacing isobutyric acid with pivalic acid affords the title compound (15) as an oil.

Example 12

O-(1-Cyclohexanoyloxyisobutoxy) S-Methyl Thiocarbonate (16)

Following the procedures of Example 9 and replacing isobutyric acid with cyclohexanecarboxylic acid affords the title compound (16) as an oil.

Example 13

[(1-Isobutanoyloxyethoxy)carbonyloxy] Succinimide (17)

To a solution of compound (2) (1 g, 4.8 mmol) in CH$_2$Cl$_2$ (10 mL) was added N-hydroxysuccinimide (1.1 g, 9.5 mmol) and the reaction mixture cooled to 0° C. A solution of 32% (v/v) peracetic acid in acetic acid (3.4 mL, 1.1 g, 14.4 mmol) was added dropwise over a period of 10 min, then the solution allowed to stir at room temperature for 3 h. The reaction mixture was diluted with ether (50 mL) and washed with water (2×10 mL), saturated sodium bicarbonate solution (10 mL) and brine (10 nm), then dried over anhydrous sodium sulfate, filtered, and concentrated in vacuo to give the title compound (17) as a as colorless oil (1 g, 77% yield). After trituration with hexane (20 mL) the product solidified to a white solid. m.p: 50-54° C. $^1$H NMR (CDCl$_3$, 400 MHz): δ 1.17 (d, J=6.8 Hz, 6H), 1.56 (d, J=5.6 Hz, 3H), 2.55 (m, 1H), 2.82 (s, 4H), 6.80 (q, J=5.2 Hz, 1H). MS (ESI) m/z 296.4 (M+Na)$^+$.

Example 14

[(1-Butanoyloxyethoxy)carbonyloxy] Succinimide (18)

Following the procedures of Example 13 and replacing compound (2) with compound (4) affords the title compound (18).

Example 15

[(1-Pivaloyloxyethoxy)carbonyloxy] Succinimide (19)

Following the procedures of Example 13 and replacing compound (2) with compound (5) affords the title compound (19).

Example 16

[(1-Cyclohexanoyloxyethoxy)carbonyloxy] Succinimide (20)

Following the procedures of Example 13 and replacing compound (2) with compound (6) affords the title compound (20).

Example 17

[(Isobutanoyloxymethoxy)carbonyloxy] Succinimide (21)

Following the procedures of Example 13 and replacing compound (2) with compound (7) affords the title compound (21).

Example 18

[(Butanoyloxymethoxy)carbonyloxy] Succinimide (22)

Following the procedures of Example 13 and replacing compound (2) with compound (8) affords the title compound (22).

Example 19

[(Pivaloyloxymethoxy)carbonyloxy] Succinimide (23)

Following the procedures of Example 13 and replacing compound (2) with compound (9) affords the title compound (23).

Example 20

[(Cyclohexanoyloxymethoxy)carbonyloxy] Succinimide (24)

Following the procedures of Example 13 and replacing compound (2) with compound (10) affords the title compound (24).

Example 21

Synthesis of (1R)-1-[((3S,4S)-2,5-Dioxo-3,4-dibenzoyloxypyrrolidinyl)-oxycarbonyloxy]-2-methylpropyl 2-methylpropanoate (25)

Step A: (3S,4S)-2,5-Dioxo-3,4-dibenzoyloxy-3,4-dihydrofuran (26)

A suspension of 2,3-dibenzoyl-D-tartaric acid (100 g, 279 mmol) in acetic anhydride (300 mL) was stirred at 85° C. for 2 h then the reaction mixture allowed to cool to room temperature. The crystalline product was collected by filtration, washed with a mixture of ether and hexane (1:1) and dried under vacuum to afford the title compound (26) (80 g, 84% yield). $^1$H NMR (CDCl$_3$, 400 MHz): δ 5.99 (s, 2H), 7.50 (m, 4H), 7.66 (m, 2H), 8.07 (m, 4H).

Step B: 1-Hydroxy-(3S,4S)-2,5-Dioxo-3,4-dibenzoyloxypyrrolidine (27)

To a suspension of (26) (60 g, 176 mmol) in a mixture of acetonitrile and water (8:1, 400 mL) at 0° C. was added a 50% aqueous solution of hydroxylamine (13.0 mL, 211 mmol). The resulting suspension was stirred overnight at room temperature to obtain a clear solution. The bulk of the acetonitrile was removed by rotary evaporation and the residue was portioned between ethyl acetate and water. The organic phase was washed successively with water and brine, dried over anhydrous Na$_2$SO$_4$ and concentrated in vacuo to afford the intermediate, 2,3-dibenzoyloxy D-tartaric acid mono-hydroxamate. This compound was suspended in toluene heated under reflux for 2 h, then cooled to room temperature to form a crystalline solid. The product was collected by filtration, washed with a mixture of ether and hexane (1:1), and dried under vacuum to afford the title compound (27) (58 g, 93% yield). $^1$H NMR (CDCl$_3$, 400 MHz): δ 6.06 (s, 2H), 7.50 (t, 4H), 7.65 (dt, 2H), 8.06 (m, 4H). MS (ESI) m/z 354.00 (M–H)$^-$.

Step C: (1R)-1-[((3S,4S)-2,5-Dioxo-3,4-dibenzoyloxypyrrolidinyl)-oxycarbonyloxy]-2-methylpropyl 2-methylpropanoate (25)

To a stirred solution of compound (27) (35 g, 98.6 mmol) and thiocarbonate (11) (34.6 g, 148 mmol) in dichloromethane at 0° C. was dropwise added a 32% solution of peracetic acid (300 mmol) in acetic acid over 2 h. The reaction temperature was kept below 35° C. during the addition of peracetic acid. After the addition was complete, the reaction mixture was stirred overnight at room temperature. The resulting white precipitate was filtered and washed successively with water, and a mixture of ether and hexane (1:2), then dried under vacuum to afford the crude title compound. This product was crystallized once from a mixture of ethyl acetate and hexane (1:1) to afford the title compound (25) (13.7 g, 25% yield). The diastereomeric purity of the product was determined to be 98.4% d.e. by HPLC using a chiral column. $^1$H NMR (CDCl$_3$, 400 MHz): δ 1.06 (d, 6H), 1.22 (d, 3H), 1.22 (d, 3H), 2.20 (m, 1H), 2.64 (hept. 1H), 6.01 (br. s, 2H), 6.64 (d, 1H), 7.47 (m, 4H), 7.63 (m, 2H), 8.07 (m, 4H).

Example 22

Synthesis of (1S)-1-[((3R,4R)-2,5-Dioxo-3,4-dibenzoyloxypyrrolidinyl)-oxycarbonyloxy]-2-methylpropyl 2-methylpropanoate (28)

Step A: (3R,4R)-2,5-Dioxo-3,4-dibenzoyloxy-3,4-dihydrofuran (29)

To a 3-necked 5 L round bottom flask fitted with a mechanical stirrer and a Teflon coated thermocouple was added (–)-2,3-dibenzoyl-L-tartaric acid (1000 g, 2.79 mol) followed by acetic anhydride (2 L). The suspension was stirred and heated to 85° C. for 2 h during which time the starting material gradually dissolved. A short time thereafter, the product began to crystallize in the reaction mixture and the suspension was then cooled to 25° C. The product was collected by filtration, washed with 10% acetone in hexane (2×1 L), and dried in a vacuum oven at 50° C. overnight to afford the title compound (29) as a white solid. $^1$H NMR (CDCl$_3$, 400 MHz): δ 6.0 (s, 2H), 7.45 (app. t, 4H), 7.65 (app. t, 2H), 8.05 (d, 4H).

Step B: 1-Hydroxy-(3R,4R)-2,5-Dioxo-3,4-dibenzoyloxypyrrolidine (30)

To a 3-neck 5 L round bottom flask fitted with a mechanical stirrer and a Teflon coated temperature probe was added (29) (2.79 mol) followed by acetonitrile (2 L). The suspension was cooled in an ice bath to 4° C., followed by the addition of 50% aqueous hydroxylamine (180 mL, 2.93 mol) over 1 h. The starting material gradually dissolved during the addition and the reaction mixture was warmed to 20° C. and stirred for 1 h. The reaction mixture was concentrated in vacuo, diluted with EtOAc (1 L) and washed with 1 N HCl (2×1 L). The organic phase was separated and concentrated in vacuo to afford a viscous red syrup. The syrup was then heated for two hours in toluene (2.5 L) at 100° C. with azeotropic removal of water. The syrup gradually dissolved and then the product crystallized. After cooling to room temperature the solid was collected by filtration, washed with 10% acetone in hexane (2×1 L) and dried in a vacuum oven to afford the title compound (30) (862 g, 2.43 mol, 87% yield) as a white solid. $^1$H NMR (CDCl$_3$, 400 MHz): δ 5.85 (s, 2H), 7.45 (app. t, 4H), 7.65 (app t, 2H), 8.05 (m, 4H).

Step C: (1S)-1-[((3R,4R)-2,5-Dioxo-3,4-dibenzoyloxypyrrolidinyl)-oxycarbonyloxy]-2-methylpropyl 2-methylpropanoate (28)

A 3 L three necked round bottom flask fitted with a mechanical stirrer, Teflon coated temperature probe and an addition funnel was charged with (11) (234 g, 1 mol), (30) (330 g, 0.95 mol), and 1,2-dichloroethane (2200 mL). The reaction mixture was cooled under a nitrogen atmosphere in an ice water bath to 15° C. To the stirred reaction mixture was added a 39% solution of peracetic acid in dilute acetic acid (500 mL, 2.94 mol) over 2 h, maintaining the temperature between 15 and 22° C. This temperature was maintained for an additional 12 h during which time a white precipitate was formed. The reaction mixture was further cooled to 3-4° C., the product collected by filtration, and washed with hexane (2×1 L). The product was dried in vacuo, yielding the title compound (28) (128 g, 0.24 mol, 25% yield). The diastereomeric purity of the product was determined to be >99% d.e. by HPLC using a chiral column. $^1$H NMR (CDCl$_3$, 400 MHz): δ 1.0 (d, 6H), 1.2 (dd, 6H), 2.1 (m, 1H), 2.65 (m, 1H), 6.0 (br. s, 2H), 6.6 (d, 1H), 7.45 (app. t, 4H), 7.65 (app. t, 2H), 8.05 (d, 4H).

Example 23

Synthesis of 3-{[1-Isobutanoyloxyethoxy] carbonylamino}propyl Phosphonous Acid (31)

To a solution of 3-aminopropylphosphonous acid (10 mmol) and sodium bicarbonate (20 mmol) in water (40 mL) is added a solution of compound (17) (10 mmol) in acetonitrile (20 mL) over 1 min. The reaction is stirred at ambient temperature for 16 h. The reaction mixture is diluted with diethyl ether (100 mL) and washed with 0.1 M aqueous potassium bisulfate (3×100 mL). The organic phase is separated, dried over anhydrous magnesium sulfate, filtered, and concentrated in vacuo to afford the title compound (31) as a white solid.

Example 24

Synthesis of 3-{[1-Butanoyloxyethoxy] carbonylamino}propyl Phosphonous Acid (32)

Following the procedure of Example 23 and replacing compound (17) with compound (18) affords the title compound (32) as a white solid.

Example 25

Synthesis of 3-{[1-Pivaloyloxyethoxy] carbonylamino}propyl Phosphonous Acid (33)

Following the procedure of Example 23 and replacing compound (17) with compound (19) affords the title compound (33) as a white solid.

Example 26

Synthesis of 3-{[1-Cyclohexanoyloxyethoxy] carbonylamino}propyl Phosphonous Acid (34)

Following the procedure of Example 23 and replacing compound (17) with compound (20) affords the title compound (34) as a white solid.

Example 27

Synthesis of 3-{[Isobutanoyloxymethoxy] carbonylamino}propyl Phosphonous Acid (35)

Following the procedure of Example 23 and replacing compound (17) with compound (21) affords the title compound (35) as a white solid.

Example 28

Synthesis of 3-{[Butanoyloxymethoxy] carbonylamino}propyl Phosphonous Acid (36)

Following the procedure of Example 23 and replacing compound (17) with compound (22) affords the title compound (36) as a white solid.

Example 29

Synthesis of 3-{[Pivaloyloxymethoxy] carbonylamino}propyl Phosphonous Acid 37)

Following the procedure of Example 23 and replacing compound (17) with compound (23) affords the title compound (37) as a white solid.

Example 30

Synthesis of 3-{[Cyclohexanoyloxymethoxy] carbonylamino}propyl Phosphonous Acid (38)

Following the procedure of Example 23 and replacing compound (17) with compound (24) affords the title compound (38) as a white solid.

Example 31

Synthesis of 3-{[(1R)-Isobutanoyloxyisobutoxy] carbonylamino}propyl Phosphonous Acid (39)

To a 3 L three necked round bottom flask fitted with a mechanical stirrer, temperature probe, and nitrogen inlet is added (25) (100 mmol), 3-aminopropylphosphonous acid (100 mmol), THF (1 L), and water (100 mL). The suspension is stirred under a nitrogen atmosphere at 18-20° C. for 4 h during which time the reaction mixture becomes homogeneous. The THF is removed in vacuo and the reaction mixture is diluted with methyl tert-butyl ether (250 mL) and washed with 1N HCl (1×500 mL) and water (2×200 mL). The organic phase is separated and concentrated in vacuo to leave a white solid. The solid is purified by flash chromatography to afford the title compound (39) as a white solid.

Example 32

Synthesis of 3-{[(1S)-Isobutanoyloxyisobutoxy] carbonylamino}propyl Phosphonous Acid (40)

Following the procedure of Example 31 and replacing compound (25) with compound (28) affords the title compound (40) as a white solid.

Example 33

Synthesis of 3-{[1-Isobutanoyloxyethoxy]carbonylamino}-(2R)-hydroxypropyl Phosphonous Acid (41)

Following the procedure of Example 23 and replacing 3-aminopropylphosphonous acid with 3-amino-(2R)-hydroxypropylphosphonous acid affords the title compound (41) as a white solid.

Example 34

Synthesis of 3-{[1-Butanoyloxyethoxy]carbonylamino}-(2R)-hydroxypropyl Phosphonous Acid (42)

Following the procedure of Example 24 and replacing 3-aminopropylphosphonous acid with 3-amino-(2R)-hydroxypropylphosphonous acid affords the title compound (42) as a white solid.

Example 35

Synthesis of 3-{[1-Pivaloyloxyethoxy]carbonylamino}-(2R)-hydroxypropyl Phosphonous Acid (43)

Following the procedure of Example 25 and replacing 3-aminopropylphosphonous acid with 3-amino-(2R)-hydroxypropylphosphonous acid affords the title compound (43) as a white solid.

Example 36

Synthesis of 3-{[1-Cyclohexanoyloxyethoxy]carbonylamino}-(2R)-hydroxypropyl Phosphonous Acid (44)

Following the procedure of Example 26 and replacing 3-aminopropylphosphonous acid with 3-amino-(2R)-hydroxypropylphosphonous acid affords the title compound (44) as a white solid.

Example 37

Synthesis of 3-{[Isobutanoyloxymethoxy]carbonylamino}-(2R)-hydroxypropyl Phosphonous Acid (45)

Following the procedure of Example 27 and replacing 3-aminopropylphosphonous acid with 3-amino-(2R)-hydroxypropylphosphonous acid affords the title compound (45) as a white solid.

Example 38

Synthesis of 3-{[Butanoyloxymethoxy]carbonylamino}-(2R)-hydroxypropyl Phosphonous Acid (46)

Following the procedure of Example 28 and replacing 3-aminopropylphosphonous acid with 3-amino-(2R)-hydroxypropylphosphonous acid affords the title compound (46) as a white solid.

Example 39

Synthesis of 3-{[Pivaloyloxymethoxy]carbonylamino}-(2R)-hydroxypropyl Phosphonous Acid (47)

Following the procedure of Example 29 and replacing 3-aminopropylphosphonous acid with 3-amino-(2R)-hydroxypropylphosphonous acid affords the title compound (47) as a white solid.

Example 40

Synthesis of 3-{[Cyclohexanoyloxymethoxy]carbonylamino}-(2R)-hydroxypropyl Phosphonous Acid (48)

Following the procedure of Example 30 and replacing 3-aminopropylphosphonous acid with 3-amino-(2R)-hydroxypropylphosphonous acid affords the title compound (48) as a white solid.

Example 41

Synthesis of 3-{[(1R)-Isobutanoyloxyisobutoxy]carbonylamino}-(2R)-hydroxypropyl Phosphonous Acid (49)

Following the procedure of Example 31 and replacing 3-aminopropylphosphonous acid with 3-amino-(2R)-hydroxypropylphosphonous acid affords the title compound (49) as a white solid.

Example 42

Synthesis of 3-{[(1S)-Isobutanoyloxyisobutoxy]carbonylamino}-(2R)-hydroxypropyl Phosphonous Acid (50)

Following the procedure of Example 32 and replacing 3-aminopropylphosphonous acid with 3-amino-(2R)-hydroxypropylphosphonous acid affords the title compound (50) as a white solid.

Example 43

Synthesis of 3-{[1-Isobutanoyloxyethoxy]carbonylamino}-(2S)-hydroxypropyl Phosphonous Acid (51)

Following the procedure of Example 23 and replacing 3-aminopropylphosphonous acid with 3-amino-(2S)-hydroxypropylphosphonous acid affords the title compound (51) as a white solid.

Example 44

Synthesis of 3-{[1-Butanoyloxyethoxy]carbonylamino}-(2S)-hydroxypropyl Phosphonous Acid (52)

Following the procedure of Example 24 and replacing 3-aminopropylphosphonous acid with 3-amino-(2S)-hydroxypropylphosphonous acid affords the title compound (52) as a white solid.

Example 45

Synthesis of 3-{[1-Pivaloyloxyethoxy]carbonylamino}-(2S)-hydroxypropyl Phosphonous Acid (50

Following the procedure of Example 25 and replacing 3-aminopropylphosphonous acid with 3-amino-(2S)-hydroxypropylphosphonous acid affords the title compound (53) as a white solid.

Example 46

Synthesis of 3-{[1-Cyclohexanoyloxyethoxy]carbonylamino}-(2S)-hydroxypropyl Phosphonous Acid (54)

Following the procedure of Example 26 and replacing 3-aminopropylphosphonous acid with 3-amino-(2S)-hydroxypropylphosphonous acid affords the title compound (54) as a white solid.

Example 47

Synthesis of 3-{[Isobutanoyloxymethoxy]carbonylamino}-(2S)-hydroxypropyl Phosphonous Acid (55)

Following the procedure of Example 27 and replacing 3-aminopropylphosphonous acid with 3-amino-(2S)-hydroxypropylphosphonous acid affords the title compound (55) as a white solid.

Example 48

Synthesis of 3-{[Butanoyloxymethoxy]carbonylamino}-(2S) hydroxypropyl Phosphonous Acid (56)

Following the procedure of Example 28 and replacing 3-aminopropylphosphonous acid with 3-amino-(2S)-hydroxypropylphosphonous acid affords the title compound (56) as a white solid.

Example 49

Synthesis of 3-{[Pivaloyloxymethoxy]carbonylamino}-(2S)-hydroxypropyl Phosphonous Acid (57)

Following the procedure of Example 29 and replacing 3-aminopropylphosphonous acid with 3-amino-(2S)-hydroxypropylphosphonous acid affords the title compound (57) as a white solid.

Example 50

Synthesis of 3-{[Cyclohexanoyloxymethoxy]carbonylamino}-(2S)-hydroxypropyl Phosphonous Acid (58)

Following the procedure of Example 30 and replacing 3-aminopropylphosphonous acid with 3-amino-(2S)-hydroxypropylphosphonous acid affords the title compound (58) as a white solid.

Example 51

Synthesis of 3-{[(1R)-Isobutanoyloxyisobutoxy]carbonylamino}-(2S)-hydroxypropyl Phosphonous Acid (59)

Following the procedure of Example 31 and replacing 3-aminopropylphosphonous acid with 3-amino-(2S)-hydroxypropylphosphonous acid affords the title compound (59) as a white solid.

Example 52

Synthesis of 3-{[(1S)-Isobutanoyloxyisobutoxy]carbonylamino}-(2S)-hydroxypropyl Phosphonous Acid (60)

Following the procedure of Example 32 and replacing 3-aminopropylphosphonous acid with 3-amino-(2S)-hydroxypropylphosphonous acid affords the title compound (60) as a white solid.

Example 53

Synthesis of 3-{[1-Isobutanoyloxyethoxy]carbonylamino}-(2R)-fluoropropyl Phosphonous Acid (61)

Following the procedure of Example 23 and replacing 3-aminopropylphosphonous acid with 3-amino-(2R)-fluoropropylphosphonous acid affords the title compound (61) as a white solid.

Example 54

Synthesis of 3-{[1-Butanoyloxyethoxy]carbonylamino}-(2R)-fluoropropyl Phosphonous Acid (62)

Following the procedure of Example 24 and replacing 3-aminopropylphosphonous acid with 3-amino-(2R)-fluoropropylphosphonous acid affords the title compound (62) as a white solid.

Example 55

Synthesis of 3-{[1-Pivaloyloxyethoxy]carbonylamino}-(2R)-fluoropropyl Phosphonous Acid (63)

Following the procedure of Example 25 and replacing 3-aminopropylphosphonous acid with 3-amino-(2R)-fluoropropylphosphonous acid affords the title compound (63) as a white solid.

Example 56

Synthesis of 3-{[1-Cyclohexanoyloxyethoxy]carbonylamino}-(2R)-fluoropropyl Phosphonous Acid (64)

Following the procedure of Example 26 and replacing 3-aminopropylphosphonous acid with 3-amino-(2R)-fluoropropylphosphonous acid affords the title compound (64) as a white solid.

Example 57

Synthesis of 3-{[Isobutanoyloxymethoxy]carbonylamino}-(2R)-fluoropropyl Phosphonous Acid (65)

Following the procedure of Example 27 and replacing 3-aminopropylphosphonous acid with 3-amino-(2R)-fluoropropylphosphonous acid affords the title compound (65) as a white solid.

Example 58

Synthesis of 3-{[Butanoyloxymethoxy]carbonylamino}-(2R)-fluoropropyl Phosphonous Acid (66)

Following the procedure of Example 28 and replacing 3-aminopropylphosphonous acid with 3-amino-(2R)-fluoropropylphosphonous acid affords the title compound (66) as a white solid.

Example 59

Synthesis of 3-{[Pivaloyloxymethoxy]carbonylamino}-(2R)-fluoropropyl Phosphonous Acid (67)

Following the procedure of Example 29 and replacing 3-aminopropylphosphonous acid with 3-amino-(2R)-fluoropropylphosphonous acid affords the title compound (67) as a white solid.

Example 60

Synthesis of 3-{[Cyclohexanoyloxymethoxy]carbonylamino}-(2R)-fluoropropyl Phosphonous Acid (68)

Following the procedure of Example 30 and replacing 3-aminopropylphosphonous acid with 3-amino-(2R)-fluoropropylphosphonous acid affords the title compound (68) as a white solid.

Example 61

Synthesis of 3-{[(1R)-Isobutanoyloxyisobutoxy]carbonylamino}-(2R)-fluoropropyl Phosphonous Acid (69)

Following the procedure of Example 31 and replacing 3-aminopropylphosphonous acid with 3-amino-(2R)-fluoropropylphosphonous acid affords the title compound (69) as a white solid.

Example 62

Synthesis of 3-{[(1S)-Isobutanoyloxyisobutoxy]carbonylamino}-(2R)-fluoropropyl Phosphonous Acid (70)

Following the procedure of Example 32 and replacing 3-aminopropylphosphonous acid with 3-amino-(2R)-fluoropropylphosphonous acid affords the title compound (70) as a white solid.

Example 63

Synthesis of 3-{[1-Isobutanoyloxyethoxy]carbonylamino}-(2S) fluoropropyl Phosphonous Acid (71)

Following the procedure of Example 23 and replacing 3-aminopropylphosphonous acid with 3-amino-(2S)-fluoropropylphosphonous acid affords the title compound (71) as a white solid.

Example 64

Synthesis of 3-{[1-Butanoyloxyethoxy]carbonylamino}-(2S)-fluoropropyl Phosphonous Acid (72)

Following the procedure of Example 24 and replacing 3-aminopropylphosphonous acid with 3-amino-(2S)-fluoropropylphosphonous acid affords the title compound (72) as a white solid.

Example 65

Synthesis of 3-{[1-Pivaloyloxyethoxy]carbonylamino}-(2S)-fluoropropyl Phosphonous Acid (73)

Following the procedure of Example 25 and replacing 3-aminopropylphosphonous acid with 3-amino-(2S)-fluoropropylphosphonous acid affords the title compound (73) as a white solid.

Example 66

Synthesis of 3-{[1-Cyclohexanoyloxyethoxy]carbonylamino}-(2S)-fluoropropyl Phosphonous Acid (74)

Following the procedure of Example 26 and replacing 3-aminopropylphosphonous acid with 3-amino-(2S)-fluoropropylphosphonous acid affords the title compound (74) as a white solid.

Example 67

Synthesis of 3-{[Isobutanoyloxymethoxy]carbonylamino}-(2S)-fluoropropyl Phosphonous Acid (75)

Following the procedure of Example 27 and replacing 3-aminopropylphosphonous acid with 3-amino-(2S)-fluoropropylphosphonous acid affords the title compound (75) as a white solid.

Example 68

Synthesis of 3-{[Butanoyloxymethoxy]carbonylamino}-(2S)-fluoropropyl Phosphonous Acid (76)

Following the procedure of Example 28 and replacing 3-aminopropylphosphonous acid with 3-amino-(2S)-fluoropropylphosphonous acid affords the title compound (76) as a white solid.

Example 69

Synthesis of 3-{[Pivaloyloxymethoxy]carbonylamino}-(2S)-fluoropropyl Phosphonous Acid (77)

Following the procedure of Example 29 and replacing 3-aminopropylphosphonous acid with 3-amino-(2S)-fluoropropylphosphonous acid affords the title compound (77) as a white solid.

Example 70

Synthesis of 3-{[Cyclohexanoyloxymethoxy]carbonylamino}-(2S)-fluoropropyl Phosphonous Acid (78)

Following the procedure of Example 30 and replacing 3-aminopropylphosphonous acid with 3-amino-(2S)-fluoropropylphosphonous acid affords the title compound (78) as a white solid.

Example 71

Synthesis of 3-{[(1R)-Isobutanoyloxyisobutoxy]carbonylamino}-(2S)-fluoropropyl Phosphonous Acid (79)

Following the procedure of Example 31 and replacing 3-aminopropylphosphonous acid with 3-amino-(2S)-fluoropropylphosphonous acid affords the title compound (79) as a white solid.

Example 72

Synthesis of 3-{[(1S)-Isobutanoyloxyisobutoxy]carbonylamino}-(2S)-fluoropropyl Phosphonous Acid (80)

Following the procedure of Example 32 and replacing 3-aminopropylphosphonous acid with 3-amino-(2S)-fluoropropylphosphonous acid affords the title compound (80) as a white solid.

Example 73

Synthesis of 3-{[1-Isobutanoyloxyethoxy]carbonylamino}-2-oxopropyl Phosphonous Acid (81)

Following the procedure of Example 23 and replacing 3-aminopropylphosphonous acid with 3-amino-2-oxopropylphosphonous acid affords the title compound (81) as a white solid.

Example 74

Synthesis of 3-{[1-Butanoyloxyethoxy]carbonylamino}-2-oxopropyl Phosphonous Acid (82)

Following the procedure of Example 24 and replacing 3-aminopropylphosphonous acid with 3-amino-2-oxopropylphosphonous acid affords the title compound (82) as a white solid.

Example 75

Synthesis of 3-{[1-Pivaloyloxyethoxy]carbonylamino}-2-oxopropyl Phosphonous Acid (83)

Following the procedure of Example 25 and replacing 3-aminopropylphosphonous acid with 3-amino-2-oxopropylphosphonous acid affords the title compound (83) as a white solid.

Example 76

Synthesis of 3-{[1-Cyclohexanoyloxyethoxy]carbonylamino}-2-oxopropyl Phosphonous Acid (84)

Following the procedure of Example 26 and replacing 3-aminopropylphosphonous acid with 3-amino-2-oxopropylphosphonous acid affords the title compound (84) as a white solid.

Example 77

Synthesis of 3-{[Isobutanoyloxymethoxy]carbonylamino}-2-oxopropyl Phosphonous Acid (85)

Following the procedure of Example 27 and replacing 3-aminopropylphosphonous acid with 3-amino-2-oxopropylphosphonous acid affords the title compound (85) as a white solid.

Example 78

Synthesis of 3-{[Butanoyloxymethoxy]carbonylamino}-2-oxopropyl Phosphonous Acid (86)

Following the procedure of Example 28 and replacing 3-aminopropylphosphonous acid with 3-amino-2-oxopropylphosphonous acid affords the title compound (86) as a white solid.

Example 79

Synthesis of 3-{[Pivaloyloxymethoxy]carbonylamino}-2-oxopropyl Phosphonous Acid (87)

Following the procedure of Example 29 and replacing 3-aminopropylphosphonous acid with 3-amino-2-oxopropylphosphonous acid affords the title compound (87) as a white-solid.

Example 80

Synthesis of 3-{[Cyclohexanoyloxymethoxy]carbonylamino}-2-oxopropyl Phosphonous Acid (88)

Following the procedure of Example 30 and replacing 3-aminopropylphosphonous acid with 3-amino-2-oxopropylphosphonous acid affords the title compound (88) as a white solid.

Example 81

Synthesis of 3-{[(1R)-Isobutanoyloxyisobutoxy]carbonylamino}-2-oxopropyl Phosphonous Acid (89)

Following the procedure of Example 31 and replacing 3-aminopropylphosphonous acid with 3-amino-2-oxopropylphosphonous acid affords the title compound (89) as a white solid.

Example 82

Synthesis of 3-{[(1S)-Isobutanoyloxyisobutoxy]carbonylamino}-2-oxopropyl Phosphonous Acid (90)

Following the procedure of Example 32 and replacing 3-aminopropylphosphonous acid with 3-amino-2-oxopropylphosphonous acid affords the title compound (90) as a white solid.

Example 83

Synthesis of 3-{[1-Isobutanoyloxyethoxy]carbonylamino}-(2R)-(4-chlorophenyl)propyl Phosphonous Acid (91)

Following the procedure of Example 23 and replacing 3-aminopropylphosphonous acid with 3-amino-(2R)-(4-chlorophenyl)propylphosphonous acid affords the title compound (91) as a white solid.

Example 84

Synthesis of 3-{[1-Butanoyloxyethoxy]carbonylamino}-(2R)-(4-chlorophenyl)propyl Phosphonous Acid (92)

Following the procedure of Example 24 and replacing 3-aminopropylphosphonous acid with 3-amino-(2R)-(4-chlorophenyl)propylphosphonous acid affords the title compound (92) as a white solid.

Example 85

Synthesis of 3-{[1-Pivaloyloxyethoxy]carbonylamino}-(2R)-(4-chlorophenyl)propyl Phosphonous Acid (93)

Following the procedure of Example 25 and replacing 3-aminopropylphosphonous acid with 3-amino-(2R)-(4-chlorophenyl)propylphosphonous acid affords the title compound (93) as a white solid.

Example 86

Synthesis of 3-{[1-Cyclohexanoyloxyethoxy]carbonylamino}-(2R)-(4-chlorophenyl)propyl Phosphonous Acid (94)

Following the procedure of Example 26 and replacing 3-aminopropylphosphonous acid with 3-amino-(2R)-(4-chlorophenyl)propylphosphonous acid affords the title compound (94) as a white solid.

Example 87

Synthesis of 3-{[Isobutanoyloxymethoxy]carbonylamino}-(2R)-(4-chlorophenyl)propyl Phosphonous Acid (95)

Following the procedure of Example 27 and replacing 3-aminopropylphosphonous acid with 3-amino-(2R)-(4-chlorophenyl)propylphosphonous acid affords the title compound (95) as a white solid.

Example 88

Synthesis of 3-{[Butanoyloxymethoxy]carbonylamino}-(2R)-(4-chlorophenyl)propyl Phosphonous Acid (96)

Following the procedure of Example 28 and replacing 3-aminopropylphosphonous acid with 3-amino-(2R)-(4-chlorophenyl)propylphosphonous acid affords the title compound (96) as a white solid.

Example 89

Synthesis of 3-{[Pivaloyloxymethoxy]carbonylamino}-(2R)-(4-chlorophenyl)propyl Phosphonous Acid (97)

Following the procedure of Example 29 and replacing 3-aminopropylphosphonous acid with 3-amino-(2R)-(4-chlorophenyl)propylphosphonous acid affords the title compound (97) as a white solid.

Example 90

Synthesis of 3-{[Cyclohexanoyloxymethoxy]carbonylamino}-(2R)-(4-chlorophenyl)propyl Phosphonous Acid (98)

Following the procedure of Example 30 and replacing 3-aminopropylphosphonous acid with 3-amino-(2R)-(4-chlorophenyl)propylphosphonous acid affords the title compound (98) as a white solid.

Example 91

Synthesis of 3-{[(1R)-Isobutanoyloxyisobutoxy]carbonylamino}-(2R)-(4-chlorophenyl)propyl Phosphonous Acid (99)

Following the procedure of Example 31 and replacing 3-aminopropylphosphonous acid with 3-amino-(2R)-(4-chlorophenyl)propylphosphonous acid affords the title compound (99) as a white solid.

Example 92

Synthesis of 3-{[(1S)-Isobutanoyloxyisobutoxy]carbonylamino}-(2R)-(4-chlorophenyl)propyl Phosphonous Acid (100)

Following the procedure of Example 32 and replacing 3-aminopropylphosphonous acid with 3-amino-(2R)-(4-chlorophenyl)propylphosphonous acid affords the title compound (100) as a white solid.

Example 93

Synthesis of 3-{[1-Isobutanoyloxyethoxy]carbonylamino}-(2S)-(4-chlorophenyl)propyl Phosphonous Acid (101)

Following the procedure of Example 23 and replacing 3-aminopropylphosphonous acid with 3-amino-(2S)-(4-chlorophenyl)propylphosphonous acid affords the title compound (101) as a white solid.

Example 94

Synthesis of 3-{[1-Butanoyloxyethoxy]carbonylamino}-(2S)-(4-chlorophenyl)propyl Phosphonous Acid (102)

Following the procedure of Example 24 and replacing 3-aminopropylphosphonous acid with 3-amino-(2S)-(4-chlorophenyl)propylphosphonous acid affords the title compound (102) as a white solid.

Example 95

Synthesis of 3-{[1-Pivaloyloxyethoxy]carbonylamino}-(2S)-(4-chlorophenyl)propyl Phosphonous Acid (103)

Following the procedure of Example 25 and replacing 3-aminopropylphosphonous acid with 3-amino-(2S)-(4-chlorophenyl)propylphosphonous acid affords the title compound (103) as a white solid.

Example 96

Synthesis of 3-{[1-Cyclohexanoyloxyethoxy]carbonylamino}-(2S)-(4-chlorophenyl)propyl Phosphonous Acid (104)

Following the procedure of Example 26 and replacing 3-aminopropylphosphonous acid with 3-amino-(2S)-(4-chlorophenyl)propylphosphonous acid affords the title compound (104) as a white solid.

Example 97

Synthesis of 3-{[Isobutanoyloxymethoxy]carbonylamino}-(2S)-(4 chlorophenyl)propyl Phosphonous Acid (105)

Following the procedure of Example 27 and replacing 3-aminopropylphosphonous acid with 3-amino-(2S)-(4-chlorophenyl)propylphosphonous acid affords the title compound (105) as a white solid.

Example 98

Synthesis of 3-{[Butanoyloxymethoxy]carbonylamino}-(2S)-(4-chlorophenyl)propyl Phosphonous Acid (106)

Following the procedure of Example 28 and replacing 3-aminopropylphosphonous acid with 3-amino-(2S)-(4-chlorophenyl)propylphosphonous acid affords the title compound (106) as a white solid.

Example 99

Synthesis of 3-{[Pivaloyloxymethoxy]carbonylamino}-(2S)-(4-chlorophenyl)propyl Phosphonous Acid (107)

Following the procedure of Example 29 and replacing 3-aminopropylphosphonous acid with 3-amino-(2S)-(4-chlorophenyl)propylphosphonous acid affords the title compound (107) as a white solid.

Example 100

Synthesis of 3-{[Cyclohexanoyloxymethoxy]carbonylamino}-(2S)-(4-chlorophenyl)propyl Phosphonous Acid (108)

Following the procedure of Example 30 and replacing 3-aminopropylphosphonous acid with 3-amino-(2S)-(4-chlorophenyl)propylphosphonous acid affords the title compound (108) as a white solid.

Example 101

Synthesis of 3-{[(1R)-Isobutanoyloxyisobutoxy]carbonylamino}-(2S)-(4-chlorophenyl)propyl Phosphonous Acid (109)

Following the procedure of Example 31 and replacing 3-aminopropylphosphonous acid with 3-amino-(2S)-(4-chlorophenyl)propylphosphonous acid affords the title compound (109) as a white solid.

Example 102

Synthesis of 3-{[(1S)-Isobutanoyloxyisobutoxy]carbonylamino}-(2S)-(4-chlorophenyl)propyl Phosphonous Acid (110)

Following the procedure of Example 32 and replacing 3-aminopropylphosphonous acid with 3-amino-(2S)-(4-chlorophenyl)propylphosphonous acid affords the title compound (110) as a white solid.

Example 103

Synthesis of 3-{[1-Isobutanoyloxyethoxy]carbonylamino}propyl Methylphosphinic Acid (111)

A solution of 3-aminopropylmethylphosphinic acid (137 mg, 1 mmol) and compound (17) (301 mg, 1 mmol) in acetonitrile (5 mL) and water (0.5 mL) was stirred at ambient temperature for 16 h. The solvent was removed under reduced pressure and the residue was purified by preparative HPLC to afford the title compound (111) as a white solid. $^1$H NMR (CDCl$_3$, 400 MHz): δ 7.69 (br, 1H), 6.77 (q, 1H, J=5.2 Hz), 3.27 (t, 2H, J=6 Hz), 2.53 (m, 1H), 1.83-1.73 (m, 4H), 1.45 (m, 6H), 1.15 (d, 6H, J=7.2 Hz). MS (ESI) m/z 296.1 (M+H)$^+$, 294.1 (M–H)$^-$.

Example 104

Synthesis of 3-{[1-Butanoyloxyethoxy]carbonylamino}propyl Methylphosphinic Acid (112)

Following the procedure of Example 103 and replacing compound (17) with compound (18) affords the title compound (112) as a white solid.

Example 105

Synthesis of 3-{[1-Pivaloyloxyethoxy]carbonylamino}propyl Methylphosphinic Acid (113)

Following the procedure of Example 103 and replacing compound (17) with compound (19) affords the title compound (113) as a white solid.

Example 106

Synthesis of 3-{[1-Cyclohexanoyloxyethoxy]carbonylamino}propyl Methylphosphinic Acid (114)

Following the procedure of Example 103 and replacing compound (17) with compound (20) afforded the title compound (114) as a white solid. $^1$H NMR (CDCl$_3$, 400 MHz): δ 7.42 (br, 1H), 6.77 (q, 1H, J=5.6 Hz), 3.25 (m, 2H), 2.27 (m, 1H), 1.90-1.59 (m, 9H), 1.43 (m, 8H), 1.31-1.18 (m, 3H). MS (ESI) m/z 336.1 (M+H)$^+$, 334.1 (M–H)$^-$.

Example 107

Synthesis of 3-{[Isobutanoyloxymethoxy]carbonylamino}propyl Methylphosphinic Acid (115)

Following the procedure of Example 103 and replacing compound (17) with compound (21) afforded the title compound (115) as a white solid. $^1$H NMR (CDCl$_3$, 400 MHz): δ 6.71 (br, 1H), 5.70 (s, 2H), 3.29 (t, 2H, J=6.4 Hz), 2.58 (m, 1H), 1.85-1.71 (m, 4H), 1.44 (d, 3H, J=14 Hz), 1.15 (d, 6H, J=6.8 Hz). MS (ESI) m/z 282.1 (M+H)$^+$, 280.0 (M−H)$^−$.

Example 108

Synthesis of 3-{[Butanoyloxymethoxy]carbonylamino}propyl Methylphosphinic Acid (116)

Following the procedure of Example 103 and replacing compound (17) with compound (22) affords the title compound (116) as a white solid.

Example 109

Synthesis of 3-{[Pivaloyloxymethoxy]carbonylamino}propyl Methylphosphinic Acid (117)

Following the procedure of Example 103 and replacing compound (17) with compound (23) affords the title compound (117) as a white solid.

Example 110

Synthesis of 3-{[Cyclohexanoyloxymethoxy]carbonylamino}propyl Methylphosphinic Acid (118)

Following the procedure of Example 103 and replacing compound (17) with compound (24) affords the title compound (118) as a white solid.

Example 111

Synthesis of 3-{[(1R)-Isobutanoyloxyisobutoxy]carbonylamino}propyl Methylphosphinic Acid (119)

To a 3 L three necked round bottom flask fitted with a mechanical stirrer, temperature probe, and nitrogen inlet is added (25) (100 mmol), 3-aminopropylmethylphosphinic acid (100 mmol), THF (1 L), and water (100 mL). The suspension is stirred under a nitrogen atmosphere at 18-20° C. for 4 h during which time the reaction mixture becomes homogeneous. The THF is removed in vacuo and the reaction mixture is diluted with methyl tert-butyl ether (250 mL) and washed with 1N HCl (1×500 mL) and water (2×200 mL). The organic phase is separated and concentrated in vacuo to leave a white solid. The solid is purified by flash chromatography to afford the title compound (119) as a white solid.

Example 112

Synthesis of 3-{[(1S)-Isobutanoyloxyisobutoxy]carbonylamino}propyl Methylphosphinic Acid (120)

Following the procedure of Example 111 and replacing compound (25) with compound (28) affords the title compound (120) as a white solid.

Example 113

Synthesis of 3-{[1-Isobutanoyloxyethoxy]carbonylamino}-(2R)-hydroxypropyl Methylphosphinic Acid (121)

Following the procedure of Example 103 and replacing 3-aminopropylmethylphosphinic acid with 3-amino-(2R)-hydroxypropylmethylphosphinic acid affords the title compound (121) as a white solid.

Example 114

Synthesis of 3-{[1-Butanoyloxyethoxy]carbonylamino}-(2R)-hydroxypropyl Methylphosphinic Acid (122)

Following the procedure of Example 104 and replacing 3-aminopropylmethylphosphinic acid with 3-amino-(2R)-hydroxypropylmethylphosphinic acid affords the title compound (122) as a white solid.

Example 115

Synthesis of 3-{[1-Pivaloyloxyethoxy]carbonylamino}-(2R)-hydroxypropyl Methylphosphinic Acid (123)

Following the procedure of Example 105 and replacing 3-aminopropylmethylphosphinic acid with 3-amino-(2R)-hydroxypropylmethylphosphinic acid affords the title compound (123) as a white solid.

Example 116

Synthesis of 3-{[1-Cyclohexanoyloxyethoxy]carbonylamino}-(2R)-hydroxypropyl Methylphosphinic Acid (124)

Following the procedure of Example 106 and replacing 3-aminopropylmethylphosphinic acid with 3-amino-(2R)-hydroxypropylmethylphosphinic acid affords the title compound (124) as a white solid, Example 117

Synthesis of 3-{[Isobutanoyloxymethoxy]carbonylamino}-(2R)-hydroxypropyl Methylphosphinic Acid (125)

Following the procedure of Example 107 and replacing 3-aminopropylmethylphosphinic acid with 3-amino-(2R)-hydroxypropylmethylphosphinic acid affords the title compound (125) as a white solid.

Example 118

Synthesis of 3-{[Butanoyloxymethoxy]carbonylamino}-(2R)-hydroxypropyl Methylphosphinic Acid (126)

Following the procedure of Example 108 and replacing 3-aminopropylmethylphosphinic acid with 3-amino-(2R)-hydroxypropylmethylphosphinic acid affords the title compound (126) as a white solid.

Example 119

Synthesis of 3-{[Pivaloyloxymethoxy]carbonylamino}-(2R)-hydroxypropyl Methylphosphinic Acid (127)

Following the procedure of Example 109 and replacing 3-aminopropylmethylphosphinic acid with 3-amino-(2R)-hydroxypropylmethylphosphinic acid affords the title compound (127) as a white solid.

Example 120

Synthesis of 3-{[Cyclohexanoyloxymethoxy]carbonylamino}-(2R)-hydroxypropyl Methylphosphinic Acid (128)

Following the procedure of Example 110 and replacing 3-aminopropylmethylphosphinic acid with 3-amino-(2R)-hydroxypropylmethylphosphinic acid affords the title compound (128) as a white solid.

Example 121

Synthesis of 3-{[(1R)-Isobutanoyloxyisobutoxy]carbonylamino}-(2R)-hydroxypropyl Methylphosphinic Acid (129)

Following the procedure of Example 111 and replacing 3-aminopropylmethylphosphinic acid with 3-amino-(2R)-hydroxypropylmethylphosphinic acid affords the title compound (129) as a white solid.

Example 122

Synthesis of 3-{[(1S)-Isobutanoyloxyisobutoxy]carbonylamino}-(2R)-hydroxypropyl Methylphosphinic Acid (130)

Following the procedure of Example 112 and replacing 3-aminopropylmethylphosphinic acid with 3-amino-(2R)-hydroxypropylmethylphosphinic acid affords the title compound (130) as a white solid.

Example 123

Synthesis of 3-{[1-Isobutanoyloxyethoxy]carbonylamino}-(2S)-hydroxypropyl Methylphosphinic Acid (131)

Following the procedure of Example 103 and replacing 3-aminopropylmethylphosphinic acid with 3-amino-(2S)-hydroxypropylmethylphosphinic acid afforded the title compound (131) as a white solid. $^1$H NMR (400 MHZ, $CD_3OD$): δ 6.71-6.73 (q, J=5.2 Hz, 1H), 4.01-4.09 (m, 1H), 3.12-3.22 (m, 2H), 2.47-2.54 (m, 1H), 1.85-1.91 (m, 2H), 1.48-1.52 (d, J=32.4 Hz, 3H), 1.42-1.44 (d, J=5.6 Hz, 3H), 1.12-1.14 (dd, J=7.2, 1.2 Hz, 6H). $^{31}$P NMR (162 MHz, $CD_3OD$): δ2.8 ppm. MS (ESI) m/z 312.36 $(M+H)^+$.

Example 124

Synthesis of 3-{[1-Butanoyloxyethoxy]carbonylamino}-(2S)-hydroxypropyl Methylphosphinic Acid (132)

Following the procedure of Example 104 and replacing 3-aminopropylmethylphosphinic acid with 3-amino-(2S)-hydroxypropylmethylphosphinic acid affords the title compound (132) as a white solid.

Example 125

Synthesis of 3-{[1-Pivaloyloxyethoxy]carbonylamino}-(2S)-hydroxypropyl Methylphosphinic Acid (133)

Following the procedure of Example 105 and replacing 3-aminopropylmethylphosphinic acid with 3-amino-(2S)-hydroxypropylmethylphosphinic acid affords the title compound (133) as a white solid.

Example 126

Synthesis of 3-{[1-Cyclohexanoyloxyethoxy]carbonylamino}-(2S)-hydroxypropyl Methylphosphinic Acid (134)

Following the procedure of Example 106 and replacing 3-aminopropylmethylphosphinic acid with 3-amino-(2S)-hydroxypropylmethylphosphinic acid affords the title compound (134) as a white solid.

Example 127

Synthesis of 3-{[Isobutanoyloxymethoxy]carbonylamino}-(2S)-hydroxypropyl Methylphosphinic Acid (135)

Following the procedure of Example 107 and replacing 3-aminopropylmethylphosphinic acid with 3-amino-(2S)-hydroxypropylmethylphosphinic acid affords the title compound (135) as a white solid.

Example 128

Synthesis of 3-{[Butanoyloxymethoxy]carbonylamino}-(2S)-hydroxypropyl Methylphosphinic Acid (136)

Following the procedure of Example 108 and replacing 3-aminopropylmethylphosphinic acid with 3-amino-(2S)-hydroxypropylmethylphosphinic acid affords the title compound (136) as a white solid.

Example 129

Synthesis of 3-{[Pivaloyloxymethoxy]carbonylamino}-(2S)-hydroxypropyl Methylphosphinic Acid (137)

Following the procedure of Example 109 and replacing 3-aminopropylmethylphosphinic acid with 3-amino-(2S)-hydroxypropylmethylphosphinic acid affords the title compound (137) as a white solid.

Example 130

Synthesis of 3-{[Cyclohexanoyloxymethoxy]carbonylamino}-(2S)-hydroxypropyl Methylphosphinic Acid (138)

Following the procedure of Example 110 and replacing 3-aminopropylmethylphosphinic acid with 3-amino-(2S)-hydroxypropylmethylphosphinic acid affords the title compound (138) as a white solid.

Example 131

Synthesis of 3-{[(1R)-Isobutanoyloxyisobutoxy]carbonylamino}-(2S)-hydroxypropyl Methylphosphinic Acid (139)

Following the procedure of Example 111 and replacing 3-aminopropylmethylphosphinic acid with 3-amino-(2S)-hydroxypropylmethylphosphinic acid affords the title compound (139) as a white solid.

Example 132

Synthesis of 3-{[(1S)-Isobutanoyloxyisobutoxy]carbonylamino}-(2S)-hydroxypropyl Methylphosphinic Acid (140)

Following the procedure of Example 112 and replacing 3-aminopropylmethylphosphinic acid with 3-amino-(2S)-hydroxypropylmethylphosphinic acid affords the title compound (140) as a white solid.

Example 133

Synthesis of 3-{[1-Isobutanoyloxyethoxy]carbonylamino}-(2R)-fluoropropyl Methylphosphinic Acid (141)

Following the procedure of Example 103 and replacing 3-aminopropylmethylphosphinic acid with 3-amino-(2R)-fluoropropylmethylphosphinic acid affords the title compound (141) as a white solid.

Example 134

Synthesis of 3-{[1-Butanoyloxyethoxy]carbonylamino}-(2R)-fluoropropyl Methylphosphinic Acid (142)

Following the procedure of Example 104 and replacing 3-aminopropylmethylphosphinic acid with 3-amino-(2R)-fluoropropylmethylphosphinic acid affords the title compound (142) as a white solid.

Example 135

Synthesis of 3-{[1-Pivaloyloxyethoxy]carbonylamino}-(2R)-fluoropropyl Methylphosphinic Acid (143)

Following the procedure of Example 105 and replacing 3-aminopropylmethylphosphinic acid with 3-amino-(2R)-fluoropropylmethylphosphinic acid affords the title compound (143) as a white solid.

Example 136

Synthesis of 3-{[1-Cyclohexanoyloxyethoxy]carbonylamino}-(2R)-fluoropropyl Methylphosphinic Acid (144)

Following the procedure of Example 106 and replacing 3-aminopropylmethylphosphinic acid with 3-amino-(2R)-fluoropropylmethylphosphinic acid affords the title compound (144) as a white solid.

Example 137

Synthesis of 3-{[Isobutanoyloxymethoxy]carbonylamino}-(2R)-fluoropropyl Methylphosphinic Acid (145)

Following the procedure of Example 107 and replacing 3-aminopropylmethylphosphinic acid with 3-amino-(2R)-fluoropropylmethylphosphinic acid affords the title compound (145) as a white solid.

Example 138

Synthesis of 3-{[Butanoyloxymethoxy]carbonylamino}-(2R)-fluoropropyl Methylphosphinic Acid (146)

Following the procedure of Example 108 and replacing 3-aminopropylmethylphosphinic acid with 3-amino-(2R)-fluoropropylmethylphosphinic acid affords the title compound (146) as a white solid.

Example 139

Synthesis of 3-{[Pivaloyloxymethoxy]carbonylamino}-(2R)-fluoropropyl Methylphosphinic Acid (147)

Following the procedure of Example 109 and replacing 3-aminopropylmethylphosphinic acid with 3-amino-(2R)-fluoropropylmethylphosphinic acid affords the title compound (147) as a white solid.

Example 140

Synthesis of 3-{[Cyclohexanoyloxymethoxy]carbonylamino}-(2R)-fluoropropyl Methylphosphinic Acid (148)

Following the procedure of Example 110 and replacing 3-aminopropylmethylphosphinic acid with 3-amino-(2R)-fluoropropylmethylphosphinic acid affords the title compound (148) as a white solid.

Example 141

Synthesis of 3-{[(1R)-Isobutanoyloxyisobutoxy]carbonylamino}-(2R)-fluoropropyl Methylphosphinic Acid (149)

Following the procedure of Example 111 and replacing 3-aminopropylmethylphosphinic acid with 3-amino-(2R)-fluoropropylmethylphosphinic acid affords the title compound (149) as a white solid.

Example 142

Synthesis of 3-{[(1S)-Isobutanoyloxyisobutoxy]carbonylamino}-(2R)-fluoropropyl Methylphosphinic Acid (150)

Following the procedure of Example 112 and replacing 3-aminopropylmethylphosphinic acid with 3-amino-(2R)-fluoropropylmethylphosphinic acid affords the title compound (150) as a white solid.

Example 143

Synthesis of 3-{[1-Isobutanoyloxyethoxy]carbonylamino}-(2S)-fluoropropyl Methylphosphinic Acid (151)

Following the procedure of Example 103 and replacing 3-aminopropylmethylphosphinic acid with 3-amino-(2S)-fluoropropylmethylphosphinic acid affords the title compound (151) as a white solid.

Example 144

Synthesis of 3-{[1-Butanoyloxyethoxy]carbonylamino}-(2S)-fluoropropyl Methylphosphinic Acid (152)

Following the procedure of Example 104 and replacing 3-aminopropylmethylphosphinic acid with 3-amino-(2S)-fluoropropylmethylphosphinic acid affords the title compound (152) as a white solid.

Example 145

Synthesis of 3-{[1-Pivaloyloxyethoxy]carbonylamino}-(2S)-fluoropropyl Methylphosphinic Acid (153)

Following the procedure of Example 105 and replacing 3-aminopropylmethylphosphinic acid with 3-amino-(2S)-fluoropropylmethylphosphinic acid affords the title compound (153) as a white solid.

Example 146

Synthesis of 3-{[1-Cyclohexanoyloxyethoxy]carbonylamino}-(2S)-fluoropropyl Methylphosphinic Acid (154)

Following the procedure of Example 106 and replacing 3-aminopropylmethylphosphinic acid with 3-amino-(2S)-fluoropropylmethylphosphinic acid affords the title compound (154) as a white solid.

Example 147

Synthesis of 3-{[Isobutanoyloxymethoxy]carbonylamino}-(2S)-fluoropropyl Methylphosphinic Acid (155)

Following the procedure of Example 107 and replacing 3-aminopropylmethylphosphinic acid with 3-amino-(2S)-fluoropropylmethylphosphinic acid affords the title compound (155) as a white solid.

Example 148

Synthesis of 3-{[Butanoyloxymethoxy]carbonylamino}-(2S)-fluoropropyl Methylphosphinic Acid (156)

Following the procedure of Example 108 and replacing 3-aminopropylmethylphosphinic acid with 3-amino-(2S)-fluoropropylmethylphosphinic acid affords the title compound (156) as a white solid.

Example 149

Synthesis of 3-{[Pivaloyloxymethoxy]carbonylamino}-(2S)-fluoropropyl Methylphosphinic Acid (157)

Following the procedure of Example 109 and replacing 3-aminopropylmethylphosphinic acid with 3-amino-(2S)-fluoropropylmethylphosphinic acid affords the title compound (157) as a white solid.

Example 150

Synthesis of 3-{[Cyclohexanoyloxymethoxy]carbonylamino}-(2)-fluoropropyl Methylphosphinic Acid (158)

Following the procedure of Example 110 and replacing 3-aminopropylmethylphosphinic acid with 3-amino-(2S)-fluoropropylmethylphosphinic acid affords the title compound (158) as a white solid.

Example 151

Synthesis of 3-{[(1R)-Isobutanoyloxyisobutoxy]carbonylamino}-(2S)-fluoropropyl Methylphosphinic Acid (159)

Following the procedure of Example 111 and replacing 3-aminopropylmethylphosphinic acid with 3-amino-(2S)-fluoropropylmethylphosphinic acid affords the title compound (159) as a white solid.

Example 152

Synthesis of 3-{[(1S)-Isobutanoyloxyisobutoxy]carbonylamino}-(2S)-fluoropropyl Methylphosphinic Acid (160)

Following the procedure of Example 112 and replacing 3-aminopropylmethylphosphinic acid with 3-amino-(2S)-fluoropropylmethylphosphinic acid affords the title compound (160) as a white solid.

Example 153

Synthesis of 3-{[1-Isobutanoyloxyethoxy]carbonylamino}-2-oxopropyl Methylphosphinic Acid (161)

Following the procedure of Example 103 and replacing 3-aminopropylmethylphosphinic acid with 3-amino-2-oxopropylmethylphosphinic acid affords the title compound (161) as a white solid.

Example 154

Synthesis of 3-{[1-Butanoyloxyethoxy]carbonylamino}-2-oxopropyl Methylphosphinic Acid (162)

Following the procedure of Example 104 and replacing 3-aminopropylmethylphosphinic acid with 3-amino-2-oxopropylmethylphosphinic acid affords the title compound (162) as a white solid.

Example 155

Synthesis of 3-{[1-Pivaloyloxyethoxy]carbonylamino}-2-oxopropyl Methylphosphinic Acid (163)

Following the procedure of Example 105 and replacing 3-aminopropylmethylphosphinic acid with 3-amino-2-oxopropylmethylphosphinic acid affords the title compound (163) as a white solid.

Example 156

Synthesis of 3-{[1-Cyclohexanoyloxyethoxy]carbonylamino}-2-oxopropyl Methylphosphinic Acid (164)

Following the procedure of Example 106 and replacing 3-aminopropylmethylphosphinic acid with 3-amino-2-oxopropylmethylphosphinic acid affords the title compound (164) as a white solid.

Example 157

Synthesis of 3-{[Isobutanoyloxymethoxy]carbonylamino}-2-oxopropyl Methylphosphinic Acid (165)

Following the procedure of Example 107 and replacing 3-aminopropylmethylphosphinic acid with 3-amino-2-oxopropylmethylphosphinic acid affords the title compound (165) as a white solid.

Example 158

Synthesis of 3-{[Butanoyloxymethoxy]carbonylamino}-2-oxopropyl Methylphosphinic Acid (166)

Following the procedure of Example 108 and replacing 3-aminopropylmethylphosphinic acid with 3-amino-2-oxopropylmethylphosphinic acid affords the title compound (166) as a white solid.

Example 159

Synthesis of 3-{[Pivaloyloxymethoxy]carbonylamino}-2-oxopropyl Methylphosphinic Acid (167)

Following the procedure of Example 109 and replacing 3-aminopropylmethylphosphinic acid with 3-amino-2-oxopropylmethylphosphinic acid affords the title compound (167) as a white solid.

Example 160

Synthesis of 3-{[Cyclohexanoyloxymethoxy]carbonylamino}-2-oxopropyl Methylphosphinic Acid (168)

Following the procedure of Example 110 and replacing 3-aminopropylmethylphosphinic acid with 3-amino-2-oxopropylmethylphosphinic acid affords the title compound (168) as a white solid.

Example 161

Synthesis of 3-{[[1R)-Isobutanoyloxyisobutoxy]carbonylamino}-2-oxopropyl Methylphosphinic Acid (169)

Following the procedure of Example 111 and replacing 3-aminopropylmethylphosphinic acid with 3-amino-2-oxopropylmethylphosphinic acid affords the title compound (169) as a white solid.

Example 162

Synthesis of 3-{[(1S)-Isobutanoyloxyisobutoxy]carbonylamino}-2-oxopropyl Methylphosphinic Acid (170)

Following the procedure of Example 112 and replacing 3-aminopropylmethylphosphinic acid with 3-amino-2-oxopropylmethylphosphinic acid affords the title compound (170) as a white solid.

Example 163

Synthesis of 3-{[1-Isobutanoyloxyethoxy]carbonylamino}-(2R)-(4-chlorophenyl)propyl Methylphosphinic Acid (171)

Following the procedure of Example 103 and replacing 3-aminopropylmethylphosphinic acid with 3-amino-(2R)-(4-chlorophenyl)propylmethylphosphinic acid affords the title compound (171) as a white solid.

Example 164

Synthesis of 3-{[1-Butanoyloxyethoxy]carbonylamino}-(2R)-(4-chlorophenyl)propyl Methylphosphinic Acid (172)

Following the procedure of Example 104 and replacing 3-aminopropylmethylphosphinic acid with 3-amino-(2R)-(4-chlorophenyl)propylmethylphosphinic acid affords the title compound (172) as a white solid.

Example 165

Synthesis of 3-{[1-Pivaloyloxyethoxy]carbonylamino}-(2R)-(4-chlorophenyl)propyl Methylphosphinic Acid (173)

Following the procedure of Example 105 and replacing 3-aminopropylmethylphosphinic acid with 3-amino-(2R)-(4-chlorophenyl)propylmethylphosphinic acid affords the title compound (173) as a white solid.

Example 166

Synthesis of 3-{[1-Cyclohexanoyloxyethoxy]carbonylamino}-(2R)-(4-chlorophenyl)propyl Methylphosphinic Acid (174)

Following the procedure of Example 106 and replacing 3-aminopropylmethylphosphinic acid with 3-amino-(2R)-(4-chlorophenyl)propylmethylphosphinic acid affords the title compound (174) as a white solid.

Example 167

Synthesis of 3-{[Isobutanoyloxymethoxy]carbonylamino}-(2R)-(4-chlorophenyl)propyl Methylphosphinic Acid (175)

Following the procedure of Example 107 and replacing 3-aminopropylmethylphosphinic acid with 3-amino-(2R)-(4-chlorophenyl)propylmethylphosphinic acid affords the title compound (175) as a white solid.

Example 168

Synthesis of 3-{[Butanoyloxymethoxy]carbonylamino}-(2R)-(4-chlorophenyl)propyl Methylphosphinic Acid (176)

Following the procedure of Example 108 and replacing 3-aminopropylmethylphosphinic acid with 3-amino-(2R)-(4-chlorophenyl)propylmethylphosphinic acid affords the title compound (176) as a white solid.

Example 169

Synthesis of 3-{[Pivaloyloxymethoxy]carbonylamino}-(2R)-(4-chlorophenyl)propyl Methylphosphinic Acid (177)

Following the procedure of Example 109 and replacing 3-aminopropylmethylphosphinic acid with 3-amino-(2R)-(4-chlorophenyl)propylmethylphosphinic acid affords the title compound (177) as a white solid.

Example 170

Synthesis of 3-{[Cyclohexanoyloxymethoxy]carbonylamino}-(2R)-(4-chlorophenyl)propyl Methylphosphinic Acid (178)

Following the procedure of Example 110 and replacing 3-aminopropylmethylphosphinic acid with 3-amino-(2R)-(4-chlorophenyl)propylmethylphosphinic acid affords the title compound (178) as a white solid.

Example 171

Synthesis of 3-{[(1R)-Isobutanoyloxyisobutoxy]carbonylamino}-(2R)-(4-chlorophenyl)propyl Methylphosphinic Acid (179)

Following the procedure of Example 111 and replacing 3-aminopropylmethylphosphinic acid with 3-amino-(2R)-(4-chlorophenyl)propylmethylphosphinic acid affords the title compound (179) as a white solid.

Example 172

Synthesis of 3-{[(1S)-Isobutanoyloxyisobutoxy]carbonylamino}-(2R)-(4-chlorophenyl)propyl Methylphosphinic Acid (180)

Following the procedure of Example 112 and replacing 3-aminopropylmethylphosphinic acid with 3-amino-(2R)-(4-chlorophenyl)propylmethylphosphinic acid affords the title compound (180) as a white solid.

Example 173

Synthesis of 3-{[1-Isobutanoyloxyethoxy]carbonylamino}-(2S)-(4-chlorophenyl)propyl Methylphosphinic Acid (181)

Following the procedure of Example 103 and replacing 3-aminopropylmethylphosphinic acid with 3-amino-(2S)-(4-chlorophenyl)propylmethylphosphinic acid affords the title compound (181) as a white solid.

Example 174

Synthesis of 3-{[1-Butanoyloxyethoxy]carbonylamino}-(2S)-(4-chlorophenyl)propyl Methylphosphinic Acid (182)

Following the procedure of Example 104 and replacing 3-aminopropylmethylphosphinic acid with 3-amino-(2S)-(4-chlorophenyl)propylmethylphosphinic acid affords the title compound (182) as a white solid.

Example 175

Synthesis of 3-{[1-Pivaloyloxyethoxy]carbonylamino}-(2S)-(4-chlorophenyl)propyl Methylphosphinic Acid (183)

Following the procedure of Example 105 and replacing 3-aminopropylmethylphosphinic acid with 3-amino-(2S)-(4-chlorophenyl)propylmethylphosphinic acid affords the title compound (183) as a white solid.

Example 176

Synthesis of 3-{[1-Cyclohexanoyloxyethoxy]carbonylamino}-(2S)-(4-chlorophenyl)propyl Methylphosphinic Acid (184)

Following the procedure of Example 106 and replacing 3-aminopropylmethylphosphinic acid with 3-amino-(2S)-(4-chlorophenyl)propylmethylphosphinic acid affords the title compound (184) as a white solid.

Example 177

Synthesis of 3-{[Isobutanoyloxymethoxy]carbonylamino}-(2S)-(4-chlorophenyl)propyl Methylphosphinic Acid (185)

Following the procedure of Example 107 and replacing 3-aminopropylmethylphosphinic acid with 3-amino-(2S)-(4-chlorophenyl)propylmethylphosphinic acid affords the title compound (185) as a white solid.

Example 178

Synthesis of 3-{[Butanoyloxymethoxy]carbonylamino}-(2S)-(4-chlorophenyl)propyl Methylphosphinic Acid (186)

Following the procedure of Example 108 and replacing 3-aminopropylmethylphosphinic acid with 3-amino-(2S)-(4-chlorophenyl)propylmethylphosphinic acid affords the title compound (186) as a white solid.

Example 179

Synthesis of 3-{[Pivaloyloxymethoxy]carbonylamino}-(2S)-(4-chlorophenyl)propyl Methylphosphinic Acid (187)

Following the procedure of Example 109 and replacing 3-aminopropylmethylphosphinic acid with 3-amino-(2S)-(4-chlorophenyl)propylmethylphosphinic acid affords the title compound (187) as a white solid.

Example 180

Synthesis of 3-{[Cyclohexanoyloxymethoxy]carbonylamino}-(2S)-(4-chlorophenyl)propyl Methylphosphinic Acid (188)

Following the procedure of Example 110 and replacing 3-aminopropylmethylphosphinic acid with 3-amino-(2S)-(4-chlorophenyl)propylmethylphosphinic acid affords the title compound (188) as a white solid.

Example 181

Synthesis of 3-{[(1R)-Isobutanoyloxyisobutoxy]carbonylamino}-(2S)-(4-chlorophenyl)propyl Methylphosphinic Acid (189)

Following the procedure of Example 111 and replacing 3-aminopropylmethylphosphinic acid with 3-amino-(2S)-(4-chlorophenyl)propylmethylphosphinic acid affords the title compound (189) as a white solid.

Example 182

Synthesis of 3-{[(1S)-Isobutanoyloxyisobutoxy]carbonylamino}-(2S)-(4-chlorophenyl)propyl Methylphosphinic Acid (190)

Following the procedure of Example 112 and replacing 3-aminopropylmethylphosphinic acid with 3-amino-(2S)-(4-chlorophenyl)propylmethylphosphinic acid affords the title compound (190) as a white solid.

Example 183

O-(Benzoyloxymethyl) S-Methyl Thiocarbonate (191)

Following the procedures of Example 1 and replacing 1-chloroethyl chloroformate with chloromethyl chloroformate in Step A and isobutyric acid with a solution of benzoic in DMF afforded the title compound (191) as an oil.

Example 184

[(1-Isobutanoyloxyisobutoxy)carbonyloxy] Succinimide (192)

Following the procedures of Example 13 and replacing compound (2) with compound (11) afforded the title compound (192) as a white solid.

Example 185

[(Benzoyloxymethoxy)carbonyloxy] Succinimide (193)

Following the procedures of Example 13 and replacing compound (2) with compound (191) afforded the title compound (193) as a white solid.

Example 186

Synthesis of 3-{[1-Isobutanoyloxyisobutoxy]carbonylamino}propyl Methylphosphinic Acid (194)

Following the procedure of Example 103 and replacing compound (17) with compound (192) afforded the title compound (194) as a white solid. $^1$H NMR (CDCl$_3$, 400 MHz): δ 6.75 (br, 1H), 6.54 (d, 1H, J=5.2 Hz), 3.27 (m, 2H), 2.55 (m, 1H), 2.00 (m, 1H), 1.81-1.70 (m, 4H), 1.43 (d, 3H, J=14.4 Hz), 1.16 (m, 6H), 0.95 (d, 6H, J=6.8 Hz). MS (ESI) m/z 324.2 (M+H)$^+$, 322.1 (M−H)$^−$.

Example 187

Synthesis of 3-{[Benzoyloxymethoxy]carbonylamino}propyl Methylphosphinic Acid (195)

Following the procedure of Example 103 and replacing compound (17) with compound (193) afforded the title compound (195) as a white solid. $^1$H NMR (CDCl$_3$, 400 MHz): δ 10.2 (br, 1H), 8.02 (d, 2H, J=7.2 Hz), 7.54 (m, 1H), 7.40 (t, 2H, J=7.6 Hz), 5.93 (s, 2H), 3.27 (m, 2H), 1.84-1.72 (m, 4H), 1.42 (d, 3H, J=14 Hz). MS (ESI) m/z 316.0 (M+H)$^+$, 314.0 (M−H)$^−$.

Example 188

Synthesis of 3-{[1-Isobutanoyloxyisobutoxy]carbonylamino}-(2S)-hydroxypropyl Methylphosphinic Acid (196)

Following the procedure of Example 103 and replacing compound (17) with compound (192) and 3-aminopropylmethylphosphinic acid with 3-amino-(2S)-hydroxypropylmethylphosphinic acid afforded the title compound (196) as a white solid. $^1$H-NMR (400 MHZ, CD$_3$OD): δ 6.49-6.5 (dd, J=4.8, 1.2 Hz, 1H), 3.97-4.01 (m, 1H), 3.13-3.21 (m, 2H), 2.51-2.55 (m, 1H), 1.95-2.03 (m, 1H), 1.80-1.88 (m, 2H), 1.45-1.48 (d, J=14.8, 3H), 1.33-1.15 (dd, J=6.8, 3.2 Hz, 6H), 0.95-0.99 (dd, J=6.8, 2.8 Hz, 6H). $^{31}$P NMR (162 MHz, CD$_3$OD): δ1.01 ppm. MS (ESI) m/z: 340.18 (M+H)$^+$.

Example 189

Standard Methods for Determination of Enzymatic Cleavage of Prodrugs in Vitro

For orally administered prodrugs it is generally desirable that the prodrug remain intact (i.e., not cleaved) while in the gastrointestinal tract and be cleaved (i.e., to release the parent drug) while in the systemic circulation. A useful level of stability can at least in part be determined by the mechanism and kinetics of absorption of the prodrug by the gastrointestinal tract. A useful level of lability can at least in part be determined by the pharmacokinetics of the prodrug and parent drug in the systemic circulation. In general, prodrugs that are more stable in a Caco-2 S9 and/or pancreatin assay and are more labile in a rat plasma, human plasma, rat liver S9, and/or human liver S9 preparation can be useful as an orally administered prodrug. The results of tests, such as those described in this example, for determining the enzymatic cleavage of prodrugs in vitro can be used to select prodrugs for in vivo testing.

The stabilities of prodrugs were evaluated in one or more in vitro systems using a variety of preparations following methods known in the art. Tissues and/or preparations were obtained from commercial sources (e.g., Pel-Freez Biologicals, Rogers, Ark., or GenTest Corporation, Woburn, Mass.). Experimental conditions used for the in vitro studies are described in Table 1. Each preparation was incubated with test compound at 37° C. for one hour. Aliquots (50 μL) were removed at 0, 30, and 60 min and quenched with 0.1% trifluoroacetic acid in acetonitrile. Samples were then centrifuged and analyzed by LC/MS/MS. Stability of prodrugs towards specific enzymes (e.g., peptidases, etc.) were also assessed in vitro by incubation with the purified enzyme:

Pancreatin Stability: Stability studies were conducted by incubating prodrug (5 μM) with 1% (w/v) pancreatin (Sigma, P-1625, from porcine pancreas) in 0.025 M Tris buffer containing 0.5 M NaCl (pH 7.5) at 37° C. for 60 min. The reaction was stopped by addition of 2 volumes of methanol. After centrifugation at 14,000 rpm for 10 min, the supernatant was removed and analyzed by LC/MS/MS.

Caco-2 Homogenate S9 Stability: Caco-2 cells were grown for 21 days prior to harvesting. Culture medium was removed and cell monolayers were rinsed and scraped off into ice-cold 10 mM sodium phosphate/0.15 M potassium chloride, pH 7.4. Cells were lysed by sonication at 4° C. using a probe sonicator. Lysed cells were then transferred into 1.5 mL centrifuge vials and centrifuged at 9000 g for 20 min at 4° C. The resulting supernatant (Caco-2 cell homogenate S9 fraction) was aliquoted into 0.5 mL vials and stored at −80° C. until used.

For stability studies, prodrug (5 μM) was incubated in Caco-2 homogenate S9 fraction (0.5 mg protein per mL) for 60 min at 37° C. Concentrations of intact prodrug and released parent drug were determined at zero time and 60 minutes using LC/MS/MS. Data from these studies is summarized in Table 2.

TABLE 1

Standard Conditions for Prodrug In Vitro Metabolism Studies

| Preparation | Substrate Concentration | Cofactors |
|---|---|---|
| Rat Plasma | 2.0 μM | None |
| Human Plasma | 2.0 μM | None |
| Rat Liver S9 (0.5 mg/mL) | 2.0 μM | NADPH* |
| Human Liver S9 (0.5 mg/mL) | 2.0 μM | NADPH* |
| Human Intestine S9 (0.5 mg/mL) | 2.0 μM | NADPH* |
| Caco-2 Homogenate | 5.0 μM | None |
| Pancreatin | 5.0 μM | None |

*NADPH generating system, e.g., 1.3 mM NADP+, 3.3 mM glucose-6-phosphate, 0.4 U/mL glucose-6-phosphate dehydrogenase, 3.3 mM magnesium chloride and 0.95 mg/mL potassium phosphate, pH 7.4.

TABLE 2

Percent of Prodrug Remaining/Percent of Parent Drug Released from Aminopropylphosphinic Acid Prodrugs after 60 min. in Various Preparations

|  | (111) | (114) | (115) | (194) | (195) |
|---|---|---|---|---|---|
| Rat Plasma | 40/48 | 98/4 | 7/74 | 38/51 | 100/8 |
| Human Plasma | 84/15 | 97/8 | 30/62 | 77/20 | 78/14 |
| Rat Liver S9 (0.5 mg/mL) | 82/17 | 51/44 | 67/27 | 63/24 | 85/12 |
| Human Liver S9 (0.5 mg/mL) | 81/17 | 43/55 | 57/31 | 66/25 | 64/32 |
| Caco-2 S9 | 82/18 | 82/19 | 20/73 | 71/28 | 91/4 |
| Pancreatin | 79/19 | 24/66 | 20/60 | 91/10 | 62/28 |

Example 190

Bioavailability of Prodrugs and Metabolites Thereof Following Intracolonic Administration in Rats Step A: Administration Protocol Rats are obtained commercially and are pre-cannulated in the both the ascending colon and the jugular vein. Animals are conscious at the time of the experiment. All animals are fasted overnight and until 4 hours post-dosing of a prodrug of 3-aminopropylphosphonous acid, 3-aminopropylphosphinic acid, or analog thereof. A 3-aminopropylphosphonous acid, 3-aminopropylphosphinic acid, or analog thereof or the corresponding prodrug is administered as a solution (in water) directly into the colon via the cannula at a dose equivalent to about 75 mg or other appropriate dose of 3-aminopropylphosphonous acid, 3-aminopropylphosphinic acid, or analog thereof per kg body weight. Blood samples (0.3 mL) are obtained from the jugular cannula at intervals over 8 hours and are quenched immediately by addition of sodium metabisulfite to prevent oxidation of the 3-aminopropylphosphonous acid, 3-aminopropylphosphinic acid, or analog thereof. Blood is then further quenched with methanol/perchloric acid to prevent hydrolysis of the prodrug. Blood samples are analyzed as described in Steps B and C.

Step B: Sample Preparation for Colonically Absorbed Drug

300 μL of methanol is added to 1.5 mL tubes. Rat blood (100 μL) is collected at different times into the tubes and vortexed to mix. 90 μL of rat blood is quenched with 300 μL methanol. 10 μL of a standard stock solution containing 3-aminopropylsulfinic acid or analog thereof (0.04, 0.2, 1, 5, 25, and 100 μg/mL) and 20 μL of p-chlorophenylalanine is added to 90 μL of rat blood to make up a final calibration standard (0.004, 0.02, 0.1, 0.5, 2.5, and 10 μg/mL). Samples are vortexed and centrifuged at 3400 rpm for 20 min. The supernatant is analyzed by LC/MS/MS.

Step C: LC/MS/MS Analysis

An API 4000 LC/MS/MS spectrometer equipped with Agilent 1100 binary pumps and a CTC HTS-PAL autosampler are used in the analysis. A ThermoHypersil-Keystone Betasil C18 100×4.6 mm, 5 μM column is used during the analysis. The mobile phase is 0.1% formic acid in water (A) and 0.1% formic acid in acetonitrile (B). The flow rate is 1.2 mL/min. The gradient condition is: 5% B for 1.0 min, then to 95% B for 2.0 min, and maintained at 95% B for 1.0 min. Then the mobile phase is returned to 5% B for 1.0 min. A TurboIon-Spray source is used on the API 4000. The analysis is done in positive ion mode for 3-aminopropylphosphonous acid and 3-aminopropylphosphinic acid and the MRM transition for each analyte is optimized using standard solution. 20 μL of the samples are injected. Non-compartmental analysis is performed using WinNonlin software (v.3.1 Professional Version, Pharsight Corporation, Mountain View, Calif.) on individual animal profiles. Summary statistics on major parameter estimates is performed for $C_{max}$ (peak observed concentration following dosing), $T_{max}$ (time to maximum concentration is the time at which the peak concentration was observed), $AUC_{(0-t)}$ (area under the plasma concentration-time curve from time zero to last collection time, estimated using the log-linear trapezoidal method), $AUC_{(0-\infty)}$, (area under the plasma concentration time curve from time zero to infinity, estimated using the log-linear trapezoidal method to the last collection time with extrapolation to infinity), and $t_{1/2,z}$ (terminal half-life).

Prodrugs that provide a bioavailability of the corresponding parent drug that is greater than the bioavailability provided by an equimolar dose of the parent drug administered to a patient by the same route, e.g., oral administration, can be useful as therapeutic agents.

Finally, it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

What is claimed is:

1. A method of treating spasticity or a symptom of spasticity in a patient, comprising administering to a patient in need of such treatment a therapeutically effective amount of at least one compound of Formula (I):

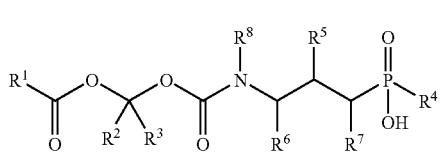

stereoisomers thereof, pharmaceutically acceptable salts thereof, a pharmaceutically acceptable solvate thereof, and combinations thereof wherein:

$R^1$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^2$ and $R^3$ are independently selected from hydrogen, alkyl, substituted alkyl, alkoxycarbonyl, substituted alkoxycarbonyl, aryl, substituted aryl, arylalkyl, substituted arylalkyl, cycloalkyl, substituted cycloalkyl, heteroaryl, substituted heteroaryl, heteroarylalkyl, and substituted heteroarylalkyl, or $R^2$ and $R^3$ together with the carbon atom to which they are bonded form a cycloalkyl, substituted cycloalkyl, cycloheteroalkyl, or substituted cycloheteroalkyl ring;

$R^4$ is selected from hydrogen, methyl, fluoromethyl, difluoromethyl, and trifluoromethyl;

$R^5$ is selected from hydrogen, hydroxy, mercapto, fluoro, oxo, $C_{1-4}$ alkyl, substituted $C_{1-4}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl;

$R^6$ and $R^7$ are independently selected from hydrogen, $C_{1-6}$ alkyl, substituted $C_{1-6}$ alkyl, $C_{1-6}$ alkoxy, substituted $C_{1-6}$ alkoxy, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl; and $R^8$ is selected from hydrogen, $C_{1-6}$ alkyl, substituted $C_{1-6}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl.

2. The method of claim 1, wherein $R^1$ is selected from methyl, ethyl, n-propyl, isopropyl, n-butyl, isobutyl, sec-butyl, tert-butyl, phenyl, cyclohexyl, and 3-pyridyl; $R^2$ is selected from hydrogen, methyl, n-propyl, and isopropyl; $R^3$ is hydrogen; $R^4$ is methyl; $R^5$ is selected from hydrogen, hydroxy, fluoro, oxo, and 4-chlorophenyl; and each of $R^6$, $R^7$, and $R^8$ is hydrogen.

3. The method of claim 1, wherein $R^1$ is isopropyl; $R^2$ is isopropyl; $R^3$ is hydrogen; $R^4$ is methyl; $R^5$ is selected from hydrogen, hydroxy, fluoro, oxo, and 4-chlorophenyl; and each of $R^6$, $R^7$, and $R^8$ is hydrogen.

4. The method of claim 1, wherein the compound of Formula (I) is selected from:
3-{[1-isobutanoyloxyethoxy]carbonylamino}propyl methylphosphinic acid;
3-{[1-cyclohexanoyloxyethoxy]carbonylamino}propyl methylphosphinic acid;
3-{[isobutanoyloxymethoxy]carbonylamino}propyl methylphosphinic acid;
3-{[1-isobutanoyloxyethoxy]carbonylamino}-(2S)-hydroxypropyl methylphosphinic acid;
3-{[1-isobutanoyloxyisobutoxy]carbonylamino}propyl methylphosphinic acid;
3-{[benzoyloxymethoxy]carbonylamino}propyl methylphosphinic acid;
3-{[1-isobutanoyloxyisobutoxy]carbonylamino}-(2S)-hydroxypropyl methylphosphinic acid;
pharmaceutically acceptable salts thereof, and pharmaceutically acceptable solvates of any of the foregoing.

5. The method of claim 1, wherein administering comprises orally administering a sustained release oral dosage form.

6. A method of treating gastroesophageal reflux disease in a patient, comprising administering to a patient in need of such treatment a therapeutically effective amount of at least one compound of Formula (I):

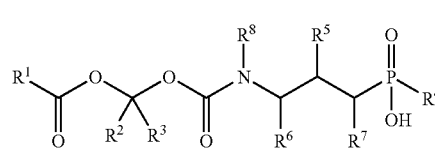

stereoisomers thereof, pharmaceutically acceptable salts thereof, a pharmaceutically acceptable solvate thereof, and combinations thereof wherein:

$R^1$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^2$ and $R^3$ are independently selected from hydrogen, alkyl, substituted alkyl, alkoxycarbonyl, substituted alkoxycarbonyl, aryl, substituted aryl, arylalkyl, substituted arylalkyl, cycloalkyl, substituted cycloalkyl, heteroaryl, substituted heteroaryl, heteroarylalkyl, and substituted heteroarylalkyl, or, $R^2$ and $R^3$ together with the carbon atom to which they are bonded form a cycloalkyl, substituted cycloalkyl, cycloheteroalkyl, or substituted cycloheteroalkyl ring;

$R^4$ is selected from hydrogen, methyl, fluoromethyl, difluoromethyl, and trifluoromethyl;

$R^5$ is selected from hydrogen, hydroxy, mercapto, fluoro, oxo, $C_{1-4}$ alkyl, substituted $C_{1-4}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl;

$R^6$ and $R^7$ are independently selected from hydrogen, $C_{1-6}$ alkyl, substituted $C_{1-6}$ alkyl, $C_{1-6}$ alkoxy, substituted $C_{1-6}$ alkoxy, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl; and $R^8$ is selected from hydrogen, $C_{1-6}$ alkyl, substituted $C_{1-6}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl.

7. The method of claim 6, wherein $R^1$ is selected from methyl, ethyl, n-propyl, isopropyl, n-butyl, isobutyl, sec-butyl, tert-butyl, phenyl, cyclohexyl, and 3-pyridyl; $R^2$ is selected from hydrogen, methyl, n-propyl, and isopropyl; $R^3$ is hydrogen; $R^4$ is methyl; $R^5$ is selected from hydrogen, hydroxy, fluoro, oxo, and 4-chlorophenyl; and each of $R^6$, $R^7$, and $R^8$ is hydrogen.

8. The method of claim 6, wherein $R^1$ is isopropyl; $R^2$ is isopropyl; $R^3$ is hydrogen; $R^4$ is methyl; $R^5$ is selected from hydrogen, hydroxy, fluoro, oxo, and 4-chlorophenyl; and each of $R^6$, $R^7$, and $R^8$ is hydrogen.

9. The method of claim 6, wherein the compound of Formula (I) is selected from:
3-{[1-isobutanoyloxyethoxy]carbonylamino}propyl methylphosphinic acid;
3-{[1-cyclohexanoyloxyethoxy]carbonylamino}propyl methylphosphinic acid;
3-{[isobutanoyloxymethoxy]carbonylamino}propyl methylphosphinic acid;
3-{[1-isobutanoyloxyethoxy]carbonylamino}-(2S)-hydroxypropyl methylphosphinic acid;
3-{[1-isobutanoyloxyisobutoxy]carbonylamino}propyl methylphosphinic acid;
3-{[benzoyloxymethoxy]carbonylamino}propyl methylphosphinic acid;
3-{[1-isobutanoyloxyisobutoxy]carbonylamino}-(2S)-hydroxypropyl methylphosphinic acid;
pharmaceutically acceptable salts thereof, and pharmaceutically acceptable solvates of any of the foregoing.

10. The method of claim 6, wherein administering comprises orally administering a sustained release oral dosage form.

11. A method of treating drug addiction or abuse, alcohol addiction or abuse, or nicotine addiction or abuse in a patient, comprising administering to a patient in need of such treatment a therapeutically effective amount of at least one compound of Formula (I):

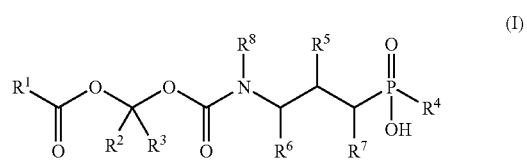

stereoisomers thereof, pharmaceutically acceptable salts thereof, a pharmaceutically acceptable solvate thereof, and combinations thereof wherein:

$R^1$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^2$ and $R^3$ are independently selected from hydrogen, alkyl, substituted alkyl, alkoxycarbonyl, substituted alkoxycarbonyl, aryl, substituted aryl, arylalkyl, substituted arylalkyl, cycloalkyl, substituted cycloalkyl, heteroaryl, substituted heteroaryl, heteroarylalkyl, and substituted heteroarylalkyl, or, $R^2$ and $R^3$ together with the carbon atom to which they are bonded form a cycloalkyl, substituted cycloalkyl, cycloheteroalkyl, or substituted cycloheteroalkyl ring;

$R^4$ is selected from hydrogen, methyl, fluoromethyl, difluoromethyl, and trifluoromethyl;

$R^5$ is selected from hydrogen, hydroxy, mercapto, fluoro, oxo, $C_{1-4}$ alkyl, substituted $C_{1-4}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl;

$R^6$ and $R^7$ are independently selected from hydrogen, $C_{1-6}$ alkyl, substituted $C_{1-6}$ alkyl, 6 alkoxy, substituted $C_{1-6}$ alkoxy, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl; and $R^8$ is selected from hydrogen, $C_{1-6}$ alkyl, substituted $C_{1-6}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl.

12. The method of claim 11, wherein $R^1$ is selected from methyl, ethyl, n-propyl, isopropyl, n-butyl, isobutyl, sec-butyl, tert-butyl, phenyl, cyclohexyl, and 3-pyridyl; $R^2$ is selected from hydrogen, methyl, n-propyl, and isopropyl; $R^3$ is hydrogen; $R^4$ is methyl; $R^5$ is selected from hydrogen, hydroxy, fluoro, oxo, and 4-chlorophenyl; and each of $R^6$, $R^7$, and $R^8$ is hydrogen.

13. The method of claim 11, wherein $R^1$ is isopropyl; $R^2$ is isopropyl; $R^3$ is hydrogen; $R^4$ is methyl; $R^5$ is selected from hydrogen, hydroxy, fluoro, oxo, and 4-chlorophenyl; and each of $R^6$, $R^7$, and $R^8$ is hydrogen.

14. The method of claim 11, wherein the compound of Formula (I) is selected from:
3-{[1-isobutanoyloxyethoxy]carbonylamino}propyl methylphosphinic acid;
3-{[1-cyclohexanoyloxyethoxy]carbonylamino}propyl methylphosphinic acid;
3-{[isobutanoyloxymethoxy]carbonylamino}propyl methylphosphinic acid;
3-{[1-isobutanoyloxyethoxy]carbonylamino}-(2S)-hydroxypropyl methylphosphinic acid;
3-{[1-isobutanoyloxyisobutoxy]carbonylamino}propyl methylphosphinic acid;

3-{[benzoyloxymethoxy]carbonylamino}propyl methylphosphinic acid;

3-{[1-isobutanoyloxyisobutoxy]carbonylamino}-(2S)-hydroxypropyl methylphosphinic acid;

pharmaceutically acceptable salts thereof, and pharmaceutically acceptable solvates of any of the foregoing.

15. The method of claim 11, wherein administering comprises orally administering a sustained release oral dosage form.

16. A method of treating cough or emesis in a patient, comprising administering to a patient in need of such treatment a therapeutically effective amount of at least one compound of Formula (I):

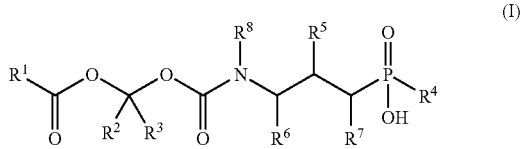

stereoisomers thereof, pharmaceutically acceptable salts thereof, a pharmaceutically acceptable solvate thereof, and combinations thereof wherein:

$R^1$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^2$ and $R^3$ are independently selected from hydrogen, alkyl, substituted alkyl, alkoxycarbonyl, substituted alkoxycarbonyl, aryl, substituted aryl, arylalkyl, substituted arylalkyl, cycloalkyl, substituted cycloalkyl, heteroaryl, substituted heteroaryl, heteroarylalkyl, and substituted heteroarylalkyl, or, $R^2$ and $R^3$ together with the carbon atom to which they are bonded form a cycloalkyl, substituted cycloalkyl, cycloheteroalkyl, or substituted cycloheteroalkyl ring;

$R^4$ is selected from hydrogen, methyl, fluoromethyl, difluoromethyl, and trifluoromethyl;

$R^5$ is selected from hydrogen, hydroxy, mercapto, fluoro, oxo, $C_{1-4}$ alkyl, substituted $C_{1-4}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl;

$R^6$ and $R^7$ are independently selected from hydrogen, $C_{1-6}$ alkyl, substituted $C_{1-6}$ alkyl, $C_{1-6}$ alkoxy, substituted $C_{1-6}$ alkoxy, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl; and $R^8$ is selected from hydrogen, $C_{1-6}$ alkyl, substituted $C_{1-6}$ alkyl, aryl, substituted aryl, $C_{3-6}$ cycloalkyl, substituted $C_{3-6}$ cycloalkyl, heteroaryl, substituted heteroaryl, $C_{7-9}$ phenylalkyl, and substituted $C_{7-9}$ phenylalkyl.

17. The method of claim 16, wherein $R^1$ is selected from methyl, ethyl, n-propyl, isopropyl, n-butyl, isobutyl, sec-butyl, tert-butyl, phenyl, cyclohexyl, and 3-pyridyl; $R^2$ is selected from hydrogen, methyl, n-propyl, and isopropyl; $R^3$ is hydrogen; $R^4$ is methyl; $R^5$ is selected from hydrogen, hydroxy, fluoro, oxo, and 4-chlorophenyl; and each of $R^6$, $R^7$, and $R^8$ is hydrogen.

18. The method of claim 16, wherein $R^1$ is isopropyl; $R^2$ is isopropyl; $R^3$ is hydrogen; $R^4$ is methyl; $R^5$ is selected from hydrogen, hydroxy, fluoro, oxo, and 4-chlorophenyl; and each of $R^6$, $R^7$, and $R^8$ is hydrogen.

19. The method of claim 16, wherein the compound of Formula (I) is selected from:

3-{[1-isobutanoyloxyethoxy]carbonylamino}propyl methylphosphinic acid;

3-{[1-cyclohexanoyloxyethoxy]carbonylamino}propyl methylphosphinic acid;

3-{[isobutanoyloxymethoxy]carbonylamino}propyl methylphosphinic acid;

3-{[1-isobutanoyloxyethoxy]carbonylamino}-(2S)-hydroxypropyl methylphosphinic acid;

3-{[1-isobutanoyloxyisobutoxy]carbonylamino}propyl methylphosphinic acid;

3-{[benzoyloxymethoxy]carbonylamino}propyl methylphosphinic acid;

3-{[1-isobutanoyloxyisobutoxy]carbonylamino}-(2S)-hydroxypropyl methylphosphinic acid;

pharmaceutically acceptable salts thereof, and pharmaceutically acceptable solvates of any of the foregoing.

20. The method of claim 16, wherein administering comprises orally administering a sustained release oral dosage form.

* * * * *